US012703860B2

(12) United States Patent
Soskine et al.

(10) Patent No.: US 12,703,860 B2
(45) Date of Patent: Aug. 11, 2026

(54) TERMINAL DEOXYNUCLEOTIDYL TRANSFERASE VARIANTS AND USES THEREOF

(71) Applicant: DNA Script, Le Kremlin-Bicêtre (FR)

(72) Inventors: Mikhael Soskine, Franconville (FR); Elise Champion, Paris (FR)

(73) Assignee: DNA Script, Le Kremlin Bicêtre (FR)

( * ) Notice: Subject to any disclaimer, the term of this patent is extended or adjusted under 35 U.S.C. 154(b) by 769 days.

(21) Appl. No.: 17/919,649

(22) PCT Filed: Apr. 16, 2021

(86) PCT No.: PCT/EP2021/059861
§ 371 (c)(1),
(2) Date: Oct. 18, 2022

(87) PCT Pub. No.: WO2021/213903
PCT Pub. Date: Oct. 28, 2021

(65) Prior Publication Data
US 2023/0159903 A1 May 25, 2023

(30) Foreign Application Priority Data
Apr. 20, 2020 (EP) .................................... 20170405

(51) Int. Cl.
*C12N 9/12* (2006.01)

(52) U.S. Cl.
CPC .... *C12N 9/1264* (2013.01); *C12Y 207/07031* (2013.01); *C12N 2310/321* (2013.01)

(58) Field of Classification Search
None
See application file for complete search history.

(56) References Cited

U.S. PATENT DOCUMENTS 5,367,066 A 11/1994 Urdea et al.
5,436,143 A 7/1995 Hyman
5,700,642 A 12/1997 Monforte et al.
5,739,386 A 4/1998 Holmes
5,744,595 A 4/1998 Srivastava et al.
5,763,594 A 6/1998 Hiatt et al.
5,808,045 A 9/1998 Hiatt et al.
5,830,655 A 11/1998 Monforte et al.
6,664,097 B2 12/2003 Russell et al.
7,057,026 B2 6/2006 Barnes et al.
7,544,794 B1 6/2009 Benner
8,034,923 B1 10/2011 Benner et al.
8,212,020 B2 7/2012 Benner et al.
8,808,988 B2 8/2014 Zhao et al.
9,410,197 B2 8/2016 Bergmann et al.
10,435,676 B2 * 10/2019 Champion .............. C12P 19/34
10,472,383 B2 11/2019 Benner
10,752,887 B2 * 8/2020 Champion ........... C12N 9/1264
10,837,040 B2 11/2020 Ybert et al.
10,913,964 B2 2/2021 Ybert et al.
11,059,849 B2 7/2021 Ybert et al.
11,208,637 B2 * 12/2021 Champion ..... C12Y 207/07031
11,268,091 B2 * 3/2022 Godron ................... C40B 50/14
11,359,221 B2 * 6/2022 Creton .................... C12P 19/34
11,390,856 B2 7/2022 Ybert et al.
11,685,941 B2 6/2023 Ybert et al.
11,859,217 B2 * 1/2024 Champion ........... C12N 9/1264
11,905,541 B2 * 2/2024 Creton .................... C12P 19/14
11,993,773 B2 * 5/2024 Godron ................... C40B 50/14
12,065,461 B2 8/2024 Sarac et al.
12,071,638 B2 * 8/2024 Champion ........... C12N 9/1264
12,286,652 B2 * 4/2025 Champion ............. C12N 15/70
2003/0186226 A1 10/2003 Brennan et al.
2004/0106728 A1 6/2004 McGall et al.
2005/0037991 A1 2/2005 Bodepudi et al.
2019/0078065 A1 3/2019 Baiga et al.
2019/0078126 A1 3/2019 Baiga et al.
2019/0211315 A1 7/2019 Champion et al.
2019/0264248 A1 * 8/2019 Ybert ..................... C12N 15/66
2019/0300923 A1 10/2019 Ybert et al.
2019/0390178 A1 12/2019 Champion et al.
2020/0002690 A1 1/2020 Ybert et al.
2020/0231619 A1 7/2020 Ybert et al.
2020/0370027 A1 11/2020 Ybert et al.
2021/0009970 A1 1/2021 Champion et al.
2021/0130863 A1 5/2021 Ybert et al.
2021/0214382 A1 7/2021 Sarac et al.
2021/0332351 A1 10/2021 Horgan et al.
(Continued)

FOREIGN PATENT DOCUMENTS

CN 107567501 A 1/2018
CN 110997907 A 4/2020
WO WO1991/006678 5/1991
WO WO2004/005667 1/2004
WO WO2015/159023 10/2015
WO 2016/034807 A1 3/2016
WO WO2017/216472 12/2017
WO 2018/215803 A1 11/2018
WO 2019/030149 A1 2/2019
WO WO2019/135007 7/2019
WO 2020/020608 A1 1/2020
WO 2020/043846 A1 3/2020
WO 2020/099451 A1 5/2020
WO 2020/120442 A2 6/2020
(Continued)

OTHER PUBLICATIONS

Bornscheuer et al. Curr Protoc Protein Sci. Nov. 2011;Chapter 26:Unit26.7 (Year: 2011).*
(Continued)

*Primary Examiner* — Christian L Fronda
(74) *Attorney, Agent, or Firm* — MORRISON & FOERSTER LLP

(57) ABSTRACT

The present invention is directed to terminal deoxynucleotidyl transferase (TdT) variants from a variety of species which display enhanced efficiency in incorporating reversibly blocked nucleoside triphosphates into a polynucleotide, and to the use of such TdTs in synthesizing polynucleotides of any predetermined sequence.

9 Claims, 1 Drawing Sheet

Specification includes a Sequence Listing.

(56) References Cited

U.S. PATENT DOCUMENTS

| | | | |
|---|---|---|---|
| 2022/0002687 A1 | 1/2022 | Champion et al. |
| 2022/0315970 A1 | 10/2022 | Horgan |
| 2022/0356510 A1 | 11/2022 | Godron et al. |
| 2022/0403354 A1 | 12/2022 | Champion et al. |
| 2022/0403434 A1 | 12/2022 | Heinisch et al. |
| 2022/0403435 A1 | 12/2022 | Horgan et al. |
| 2022/0403436 A1 | 12/2022 | Horgan et al. |
| 2022/0411840 A1 | 12/2022 | Champion et al. |
| 2023/0062303 A1 | 3/2023 | Champion et al. |
| 2023/0089448 A1 | 3/2023 | Horgan et al. |
| 2023/0167421 A1 | 6/2023 | Ybert et al. |
| 2023/0193222 A1 | 6/2023 | Ybert et al. |
| 2023/0203553 A1 | 6/2023 | Ybert |
| 2023/0241571 A1 | 8/2023 | Martin et al. |
| 2023/0313255 A1 | 10/2023 | Horgan et al. |
| 2023/0416708 A1 | 12/2023 | Loftie-Eaton et al. |
| 2024/0052391 A1 | 2/2024 | Godron et al. |
| 2024/0093165 A1 | 3/2024 | Champion et al. |
| 2024/0093256 A1 | 3/2024 | Soskine et al. |
| 2024/0124855 A1 | 4/2024 | Ybert et al. |
| 2024/0254459 A1 | 8/2024 | Champion et al. |
| 2024/0279700 A1 | 8/2024 | Horgan |

FOREIGN PATENT DOCUMENTS

| | | |
|---|---|---|
| WO | 2020/141143 A1 | 7/2020 |
| WO | 2021/018919 A1 | 2/2021 |
| WO | 2021/018921 A1 | 2/2021 |
| WO | 2021/048142 A1 | 3/2021 |
| WO | 2021/058438 A1 | 4/2021 |
| WO | 2021/094251 A1 | 5/2021 |
| WO | 2021/116270 A1 | 6/2021 |
| WO | 2021/122539 A1 | 6/2021 |
| WO | 2021/170524 A1 | 9/2021 |
| WO | 2021/254934 A1 | 12/2021 |
| WO | 2022/013094 A1 | 1/2022 |
| WO | 2022/063835 A1 | 3/2022 |
| WO | 2022/090057 A1 | 5/2022 |
| WO | 2022/090323 A1 | 5/2022 |
| WO | 2022/207934 A1 | 10/2022 |
| WO | 2022/258809 A1 | 12/2022 |
| WO | 2023/025488 A1 | 3/2023 |
| WO | 2023/083997 A2 | 5/2023 |
| WO | 2023/083999 A2 | 5/2023 |
| WO | 2023/170266 A1 | 9/2023 |

OTHER PUBLICATIONS

Accession BDD30476. Sep. 22, 2016. (Year: 2016).*

Becker et al. (1967) "The Enzymatic Cleavage of Phosphate Termini from Polynucleotides", The Journal of Biological Chemistry, 242(5): 936-950.

Bentolila et al (1995) "The Two Isoforms of Mouse Terminal Deoxynucleotidyl Transferase Differ in Both the Ability to Add N Regions and Subcellular Localization", The EMBO Journal, 14(17): 4221-4229.

Boule et al (1998) "High-Level Expression of Murine Terminal Deoxynucleotidyl Transferase in *Escherichia coli* Grown at Low Temperature and Overexpressing argU tRNA", Molecular Biotechnology, 10: 199-208.

Cameron et al. (1977) "3'-Phosphatase Activity in T4 Polynucleotide Kinase", Biochemistry, 16(23): 5120-5126.

Canard et al. (1994) "DNA Polymerase Fluorescent Substrates with Reversible 3'-Tags", Gene., 148(1): 1-6.

Canard et al. (1995) "Catalytic Editing Properties of DNA Polymerases", Proc Natl. Acad. Sci, 92(24): 10859-10863.

Corpet (1988) "Multiple sequence alignment with hierarchical clustering", Nucleic Acids Research, 16(22): 10881-10890.

Ferrero et al. (2000) "Chemoenzymatic Transformations in Nucleoside Chemistry", Monatshefte fur Chemie 131: 585-616.

Grantham, R. (1974) "Amino Acid Difference Formula to Help Explain Protein Evolution", Science, 185: 862-864.

Guo et al. (2008) "Four-color DNA Sequencing with 3'-O-Modified Nucleotide Reversible Terminators and Chemically Cleavable Fluorescent Dideoxynucleotides", Proc. Natl. Acad. Sci., 105(27): 9145-9150.

Jensen et al (2018) "Template-Independent Enzymatic Oligonucleotide Synthesis (TiEOS)", Biochemistry, 57(12): 1821-1832.

Kodumal et al (2004) "Total synthesis of long DNA sequences: Synthesis of acontiguous 32-kb polyketide synthase gene cluster", The National Academy of Sciences of the USA, 101(44): 15573-15578.

Mathews et al. (2016) "Photo-Cleavable Nucleotides for Primer Free Enzyme Mediated DNA Synthesis", Organic & Biomolecular Chemistry, 14(35): 8278-8288.

Meng et al. (2006) "Design and Synthesis of a Photocleavable Fluorescent Nucleotide 3'-O-Allyl-dGTP-PC-Bodipy-FL-510 as a Reversible Terminator for DNA Sequencing by Synthesis", J. Org. Chem., 71(8): 3248-3252.

Metzker et al. (1994) "Termination of DNA Synthesis by Novel 3'-Modifieddeoxyribonucleoside 5'-Triphosphates", Nucleic Acids Research, 22(20): 4259-4267.

Rasolonjatovo et al. (1999) "Development of a New DNA Sequencing Method: 3'-Ester Cleavage Catalyzed by Taq DNA Polymerase", Nucleosides & Nucleotides, 18(4&5): 1021-1022.

Schmitz et al. (1999) "Solid-Phase Enzymatic Synthesis of Oligonucleotides", Organic Letters, 1(11): 1729-1731.

Stemmer et al (1995) "Single-step assembly of a gene and entire plasmid from large numbers of oligodeoxyribonucleotides", Gene, 164: 49-53.

Taunton-Rigby, Alison (1973) "Oligonucleotide Synthesis. III. Enzymatically Removable Acyl Protecting Groups", J. Org. Chem., 38(5): 977-985.

Uemura et al. (1989) "Regioselective Deprotection of 3',5'-O-Acylated Pyrimidine Nucleosides by Lipase and Esterase", Tetrahedron Letters, 30(29): 3819-3820.

Altschul, S. F. et al. (2005). "Protein Database Searches Using Compositionally Adjusted," FEBS J. 272:5101-5109.

Altschul, S.F. et al. (1997). "Gapped BLAST and PSI-BLAST: A new Generation of Protein Database Search Programs," Nucleic Acids Research 25(17):3389-3402.

Repasky, J.A.E. et al. (2004). "Mutational Analysis of Terminal Deoxynucleotidyltransferase-Mediated N-Nucleotide Addition in V(D)J Recombination," The Journal of Immunology 172(9):5478-5488, 12 pages.

Smith, T.F. et al. (1981). "Identification of Common Molecular Subsequence," J. Mol. Biol. 147:195-197.

GenBank Accession No. XP_003133204.1, last updated May 13, 2017, located at <http://www.ncbi.nlm.nih.gov/protein/XP_003133204.1>, last visited on Sep. 4, 2025, two pages.

* cited by examiner

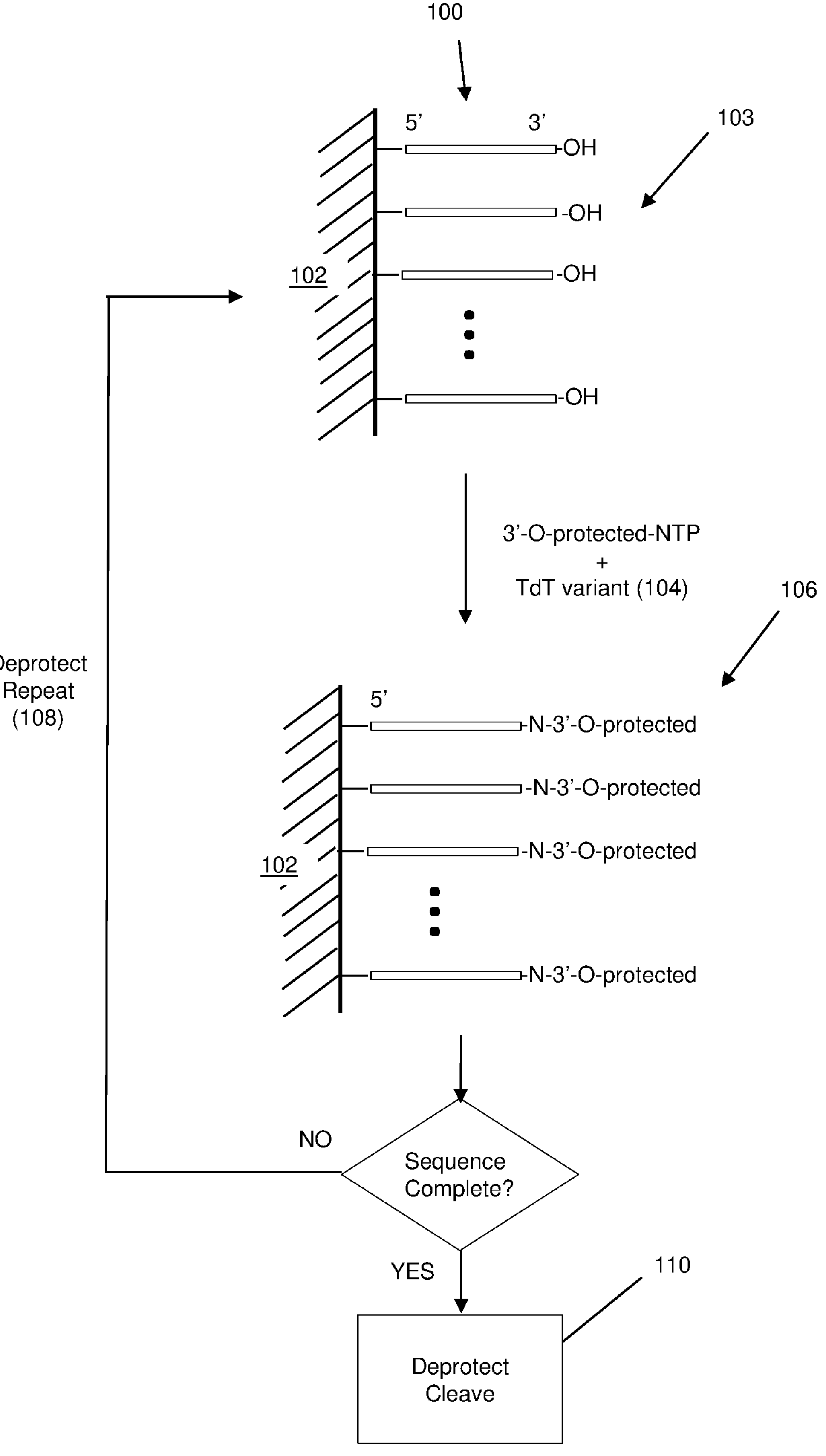
100
103
5'
3'
-OH
-OH
-OH
-OH
102
3'-O-protected-NTP
+
TdT variant (104)
106
Deprotect
Repeat
(108)
5'
-N-3'-O-protected
-N-3'-O-protected
-N-3'-O-protected
-N-3'-O-protected
102
NO
Sequence
Complete?
YES
110
Deprotect
Cleave

TERMINAL DEOXYNUCLEOTIDYL TRANSFERASE VARIANTS AND USES THEREOF

BACKGROUND

Synthetic polynucleotides of predetermined sequences are central to a host of technologies, including molecular diagnostics, genomic and diagnostic sequencing, nucleic acid amplification, therapeutic antibody development, synthetic biology, nucleic acid-based therapeutics, DNA origami, DNA-based data storage, and the like. Recently, interest has arisen in supplementing or replacing chemically-based synthesis methods by enzymatically-based methods using template-free polymerases, such as, terminal deoxynucleotidyl transferase (TdT), because of the proven efficiency of such enzymes and the benefit of mild non-toxic reaction conditions, e.g. Ybert et al, International patent publication WO2015/159023; Hiatt et al, U.S. Pat. No. 5,763,594; Jensen et al, Biochemistry, 57: 1821-1832 (2018); and the like. Most approaches in enzyme-based synthesis require the use of reversibly blocked nucleoside triphosphates in order to obtain a desired sequence in the polynucleotide product. Unfortunately, however, natural TdTs incorporate such modified nucleoside triphosphates with greatly reduced efficiency as compared to unmodified nucleoside triphosphates.

In view of the above, the field of template-free enzymatically-based polynucleotide synthesis would be advanced if new template-free polymerases, such as variant TdTs, were available that could incorporate reversibly blocked nucleoside triphosphates with greater efficiency.

SUMMARY OF THE INVENTION

The present invention is directed to terminal deoxynucleotidyl transferase (TdT) variants from a variety of species which display enhanced efficiency in incorporating reversibly blocked nucleoside triphosphates into a polynucleotide, and to their use in synthesizing polynucleotides of any predetermined sequence.

In some embodiments, the invention is directed to a terminal deoxynucleotidyl transferase (TdT) variant comprising an amino acid sequence at least sixty percent identical to an amino acid sequence selected from SEQ ID NO: 2, 5, 8, 11, 14, 17, 20, 23, 26, 29, 32, 35, 38, 41, 44 or 47, wherein with respect to SEQ ID NO: 2 leucine at position 61 is substituted, cysteine at position 170 is substituted, arginine at position 204 is substituted, arginine at position 326 is substituted and glycine at position 329 is substituted;

with respect to SEQ ID NO: 5 leucine at position 48 is substituted, cysteine at position 158 is substituted, arginine at position 192 is substituted, arginine at position 314 is substituted and glycine at position 317 is substituted;

with respect to SEQ ID NO: 8 leucine at position 61 is substituted, tyrosine at position 171 is substituted, arginine at position 205 is substituted, arginine at position 327 is substituted and glutamic acid at position 329 is substituted;

with respect to SEQ ID NO: 11 leucine at position 61 is substituted, tyrosine at position 171 is substituted, arginine at position 205 is substituted, arginine at position 324 is substituted and glutamic acid at position 327 is substituted;

with respect to SEQ ID NO: 14 glycine at position 61 is substituted, arginine at position 205 is substituted, arginine at position 327 is substituted and glutamic acid at position 330 is substituted;

with respect to SEQ ID NO: 17 arginine at position 61 may or may not be substituted, alanine at position 158 is substituted, arginine at position 192 is substituted, arginine at position 311 is substituted and glutamic acid at position 314 is substituted;

with respect to SEQ ID NO: 20 arginine at position 61 may or may not be substituted, proline at position 171 may or may not be substituted, arginine at position 205 is substituted, threonine at position 321 is substituted and glutamic acid at position 324 is substituted;

with respect to SEQ ID NO: 23 arginine at position 61 may or may not be substituted, alanine at position 171 may or may not be substituted, arginine at position 205 is substituted, alanine at position 322 may or may not be substituted and glutamic acid at position 325 is substituted;

with respect to SEQ ID NO: 26 arginine at position 61 may or may not be substituted, alanine at position 171 may or may not be substituted, arginine at position 205 is substituted, arginine at position 322 is substituted and glutamic acid at position 325 is substituted;

with respect to SEQ ID NO: 29 methionine at position 48 is substituted, cysteine at position 158 is substituted, arginine at position 192 is substituted, arginine at position 310 is substituted and glutamic acid at position 313 is substituted;

with respect to SEQ ID NO: 32 methionine at position 61 is substituted, cysteine at position 171 is substituted, arginine at position 205 is substituted, arginine at position 323 is substituted and glutamic acid at position 326 is substituted;

with respect to SEQ ID NO: 35 methionine at position 61 is substituted, cysteine at position 171 is substituted, arginine at position 205 is substituted, arginine at position 323 is substituted and glutamic acid at position 326 is substituted;

with respect to SEQ ID NO: 38 methionine at position 61 is substituted, cysteine at position 171 is substituted, arginine at position 205 is substituted, arginine at position 323 is substituted and glutamic acid at position 326 is substituted;

with respect to SEQ ID NO: 41 methionine at position 61 is substituted, cysteine at position 171 is substituted, arginine at position 205 is substituted, arginine at position 323 is substituted and glutamic acid at position 326 is substituted;

with respect to SEQ ID NO: 44 methionine at position 48 is substituted, cysteine at position 158 is substituted, arginine at position 192 is substituted, arginine at position 309 is substituted and glutamic acid at position 312 is substituted; and with respect to SEQ ID NO: 47 methionine at position 61 is substituted, cysteine at position 171 is substituted, arginine at position 205 is substituted, arginine at position 323 is substituted and glutamic acid at position 326 is substituted; and wherein the TdT variant (i) is capable of synthesizing a nucleic acid fragment without a template and (ii) is capable of incorporating a 3'-O-modified nucleotide onto a free 3'-hydroxyl of a nucleic acid fragment.

In some embodiments, the above substitution for leucine at position 61 in SEQ ID NO: 2, 8 or 11 or position 48 in SEQ ID NO: 5 is selected from the group consisting of R or Q. In some embodiments, the above substitution for cysteine at position 170 in SEQ ID NO: 2 or position 158 in SEQ ID NO: 5, 29 or 44 or position 171 in SEQ ID NO: 32, 35, 38, 41 or 47 is selected from the group consisting of G, R, P, A, V, S, N, Q or D; and in other embodiments, the substitution for cysteine at the foregoing positions is selected from the group consisting of G or R. In some embodiments, the above substitution for tyrosine at position 171 of SEQ ID NO: 8 or 11 is selected from the group consisting of G, R, P, A, V, S, N, Q or D; and in other embodiments, the substitution for tyrosine at the foregoing positions is selected from the group consisting of G or R. In some embodiments, the above substitution for alanine at position 158 of SEQ ID NO: 17 or position 171 of SEQ ID NO: 23 or 26 is selected from the group consisting of G, R, P, V, S, N, Q or D; and in other embodiments, the substitution for alanine at the foregoing positions is selected from the group consisting of G or R. In some embodiments, the above substitution for proline at position 171 of SEQ ID NO: 20 is selected from the group consisting of G, R, A, V, S, N, Q or D; and in other embodiments, the substitution for tyrosine at the foregoing positions is selected from the group consisting of G or R. In some embodiments, the above substitution for arginine at position 204 of SEQ ID NO: 2 or position 192 of SEQ ID NO: 5, 17, 29 or 44 or position 205 of SEQ ID NO: 8, 11, 14, 20, 23, 26, 32, 35, 38, 41 or 47 is selected from the group consisting of L or N. In some embodiments, the above substitution for arginine at position 326 of SEQ ID NO: 2 or position 314 of SEQ ID NO: 5 or position 327 of SEQ ID NO: 8 or 14 or position 324 of SEQ ID NO: 11 or position 311 of SEQ ID NO: 17 or position 321 of SEQ ID NO: 20 or position 322 of SEQ ID NO: 23 or 26 or position 310 of SEQ ID NO: 29 or position 323 of SEQ ID NO: 32, 35, 38, 41 or 47 or position 309 of SEQ ID NO: 44 is selected from the group consisting of P, N or A. In some embodiments, the above substitution for threonine at position 321 of SEQ ID NO: 20 is selected from the group consisting of P, N or A. In some embodiments, the above substitution for glycine at position 329 of SEQ ID NO: 2 or 5 is selected from the group consisting of N, L, T or S. In some embodiments, the above substitution for glutamic acid at position 330 of SEQ ID NO: 8 or 14 or position 327 of SEQ ID NO: 11 or position 311 of SEQ ID NO: 17 or position 324 of SEQ ID NO: 20 or position 325 of SEQ ID NO: 23 or 26 or position 313 of SEQ ID NO: 29 position 326 of SEQ ID NO: 32, 35, 38, 41 or 47 or position 312 of SEQ ID NO: 44 is selected from the group consisting of N, L, T or S.

In further embodiments, the invention is directed to a terminal deoxynucleotidyl transferase (TdT) variant comprising an amino acid sequence at least sixty percent identical to an amino acid sequence selected from SEQ ID NO: 2, 5, 8, 11, 14, 17, 20, 23, 26, 29, 32, 35, 38, 41, 44 or 47, substituted as described above and further substituted as follows:

- with respect to SEQ ID NO: 2 glutamine at position 327 is substituted;
- with respect to SEQ ID NO: 5 glutamic acid at position 315 is substituted;
- with respect to SEQ ID NO: 8 glutamine at position 328 is substituted;
- with respect to SEQ ID NO: 11 glutamine at position 325 is substituted;
- with respect to SEQ ID NO: 14 glutamine at position 328 is substituted;
- with respect to SEQ ID NO: 17 glutamine at position 312 is substituted;

- with respect to SEQ ID NO: 20 glutamine at position 322 is substituted;
- with respect to SEQ ID NO: 23 glutamine at position 323 is substituted;
- with respect to SEQ ID NO: 26 methionine at position 323 is substituted;
- with respect to SEQ ID NO: 29 glutamine at position 311 is substituted;
- with respect to SEQ ID NO: 32 glutamine at position 324 is substituted;
- with respect to SEQ ID NO: 35 glutamine at position 324 is substituted;
- with respect to SEQ ID NO: 38 glutamine at position 324 is substituted;
- with respect to SEQ ID NO: 41 glutamine at position 324 is substituted;
- with respect to SEQ ID NO: 44 glutamine at position 310 is substituted; and
- with respect to SEQ ID NO: 47 glutamine at position 324 is substituted;
- and wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the foregoing substitutions of glutamine and glutamic acid are T, F, L or M.

In some embodiments, the invention is directed to a terminal deoxynucleotidyl transferase (TdT) variant comprising an amino acid sequence at least ninety percent identical to an amino acid sequence selected from SEQ ID NO: 3, 6, 9, 12, 15, 18, 21, 24, 27, 30, 33, 36, 39, 42, 45 or 48, wherein:

- with respect to SEQ ID NO: 3 amino acid position 61 is R, amino acid position 171 is R, amino acid position 205 is L, amino acid position 327 is A, and amino acid position 330 is N;
- with respect to SEQ ID NO: 6 amino acid position 48 is R, amino acid position 158 is R, amino acid position 192 is L, amino acid position 314 is P, and amino acid position 317 is N;
- with respect to SEQ ID NO: 9 amino acid position 61 is R, amino acid position 171 is R, amino acid position 205 is L, amino acid position 327 is A, and amino acid position 330 is N;
- with respect to SEQ ID NO: 12 amino acid position 61 is R, amino acid position 171 is A, amino acid position 205 is L, amino acid position 324 is P, and amino acid position 327 is N;
- with respect to SEQ ID NO: 15 amino acid position 61 is R, amino acid position 171 is R, amino acid position 205 is L, amino acid position 328 is P, and amino acid position 331 is N;
- with respect to SEQ ID NO: 18 amino acid position 48 is R, amino acid position 158 is R, amino acid position 192 is L, amino acid position 311 is P, and amino acid position 314 is N;
- with respect to SEQ ID NO: 21 amino acid position 61 is R, amino acid position 171 is P, amino acid position 205 is L, amino acid position 321 is A, and amino acid position 324 is N;
- with respect to SEQ ID NO: 24 amino acid position 61 is R, amino acid position 171 is A, amino acid position 205 is L, amino acid position 322 is A, and amino acid position 325 is N;

with respect to SEQ ID NO: 27 amino acid position 61 is R, amino acid position 171 is R, amino acid position 205 is L, amino acid position 327 is A, and amino acid position 330 is N;

with respect to SEQ ID NO: 30 amino acid position 48 is R, amino acid position 158 is R, amino acid position 192 is L, amino acid position 310 is P, and amino acid position 313 is N;

with respect to SEQ ID NO: 33 amino acid position 61 is R, amino acid position 171 is R, amino acid position 205 is L, amino acid position 323 is P, and amino acid position 326 is N;

with respect to SEQ ID NO: 36 amino acid position 61 is R, amino acid position 171 is R, amino acid position 205 is L, amino acid position 323 is A, and amino acid position 326 is N;

with respect to SEQ ID NO: 39 amino acid position 61 is R, amino acid position 171 is R, amino acid position 205 is L, amino acid position 323 is P, and amino acid position 326 is N;

with respect to SEQ ID NO: 42 amino acid position 61 is R, amino acid position 171 is R, amino acid position 205 is L, amino acid position 323 is A, and amino acid position 326 is N;

with respect to SEQ ID NO: 45 amino acid position 48 is R, amino acid position 158 is R, amino acid position 192 is L, amino acid position 310 is A, and amino acid position 313 is N;

with respect to SEQ ID NO: 48 amino acid position 61 is R, amino acid position 171 is R, amino acid position 205 is L, amino acid position 323 is P, and amino acid position 326 is N;

and wherein the TdT variant (i) is capable of synthesizing a nucleic acid fragment without a template and (ii) is capable of incorporating a 3'-O-modified nucleotide onto a free 3'-hydroxyl of a nucleic acid fragment.

In some embodiments, in the foregoing TdT variants, with respect to SEQ ID NO: 3 amino acid position 328 is Q or is selected from the group consisting of T, F, L or M;

with respect to SEQ ID NO: 6 amino acid position 315 is Q or is selected from the group consisting of T, F, L or M;

with respect to SEQ ID NO: 9 amino acid position 328 is Q or is selected from the group consisting of T, F, L or M;

with respect to SEQ ID NO: 12 amino acid position 325 is Q or is selected from the group consisting of T, F, L or M;

with respect to SEQ ID NO: 15 amino acid position 329 is Q or is selected from the group consisting of T, F, L or M;

with respect to SEQ ID NO: 18 amino acid position 312 is Q or is selected from the group consisting of T, F, L or M;

with respect to SEQ ID NO: 21 amino acid position 322 is Q or is selected from the group consisting of T, F, L or M;

with respect to SEQ ID NO: 24 amino acid position 323 is Q or is selected from the group consisting of T, F, L or M;

with respect to SEQ ID NO: 27 amino acid position 328 is Q or is selected from the group consisting of T, F, L or M;

with respect to SEQ ID NO: 30 amino acid position 311 is Q or is selected from the group consisting of T, F, L or M;

with respect to SEQ ID NO: 33 amino acid position 324 is Q or is selected from the group consisting of T, F, L or M;

with respect to SEQ ID NO: 36 amino acid position 324 is Q or is selected from the group consisting of T, F, L or M;

with respect to SEQ ID NO: 39 amino acid position 324 is Q or is selected from the group consisting of T, F, L or M;

with respect to SEQ ID NO: 42 amino acid position 324 is Q or is selected from the group consisting of T, F, L or M;

with respect to SEQ ID NO: 45 amino acid position 311 is Q or is selected from the group consisting of T, F, L or M; and with respect to SEQ ID NO: 48 amino acid position 324 is Q or is selected from the group consisting of T, F, L or M.

In some embodiments, the invention is directed to a terminal deoxynucleotidyl transferase (TdT) variant comprising an amino acid sequence selected from SEQ ID NO: 3, 6, 9, 12, 15, 18, 21, 24, 27, 30, 33, 36, 39, 42, 45 or 48.

In some embodiments, the percent identity value with respect to each of the foregoing TdT variants is at least 80 percent identity with the indicated SEQ ID NOs; in some embodiments, the above percent identity value is at least 90 percent identity with the indicated SEQ ID NOs; in some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity. As used herein, the percent identity values used to compare a reference sequence to a variant sequence do not include the expressly specified amino acid positions containing substitutions of the variant sequence; that is, the percent identity relationship is between sequences of a reference protein and sequences of a variant protein outside of the expressly specified positions containing substitutions in the variant. Thus, for example, if the reference sequence and the variant sequence each comprised 100 amino acids and the variant sequence had mutations at positions 25 and 81, then the percent homology would be in regard to sequences 1-24, 26-80 and 82-100. In regard to (ii) above, in some embodiments, such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'-O-(2-nitrobenzyl)-nucleoside triphosphate, a 3'-O-nitro-nucleoside triphosphate or a 3'-O-propargyl-nucleoside triphosphate. In other embodiments, such 3'-O-modified nucleotide may comprise a 3'-O—NH2-nucleoside triphosphate or a 3'-O-azidomethyl-nucleoside triphosphate.

The invention further relates to the use of a TdT variant of the invention for synthesizing a nucleic acid molecule without template by the successive addition of one or more 3'-O-modified nucleotides to a nucleic acid fragment. In some embodiments, such methods comprise the steps of (a) providing an initiator comprising an oligonucleotide having a free 3'-hydroxyl; (b) reacting under enzymatic extension conditions a TdT variant of the invention with the initiator or an extended initiator in the presence of a 3'-O-reversibly blocked nucleoside triphosphate. In some embodiments, such method further includes steps of (c) deblocking the extended initiators to form extended initiators with free 3'-hydroxyls and (d) repeating steps (b) and (c) until a nucleic acid molecule of a predetermined sequence is synthesized.

In further embodiments, the invention includes nucleic acid molecules encoding a variant TdTs described above, expression vectors comprising such nucleic acid molecules, and host cells comprising the aforementioned nucleic acid molecules or the aforementioned expression vectors. In still further embodiments, the invention includes processes for producing a variant TdT of the invention, wherein a host cell is cultivated under culture conditions allowing the expression of the nucleic acid encoding said variant TdT, and wherein the variant TdT is optionally retrieved. The invention also includes kits for performing template-free polynucleotide elongations of any predetermine sequence, wherein the kits include a TdT variant of the invention. Such kits may further comprise 3'-O-blocked deoxyribonucleoside triphosphates (dNTPs) for A, C, G and T for DNA elongation, or 3'-O-blocked ribonucleoside triphosphates (rNTPs) for rA, rC, rG and U for RNA elongation.

The present invention advantageously overcomes problems in the field of template-free enzymatic nucleic acid synthesis related to the efficient incorporation of 3'-O-modified nucleoside triphosphates by providing new TdT variants with a capability of incorporating 3'-O-modified nucleotides with greater efficiency or at a higher rate than wild type TdTs or previously available TdT variants. In some embodiments, the present invention also advantageously overcomes problems in the above field by providing new TdT variants with increased stability in comparison with wild type TdTs.

BRIEF DESCRIPTION OF THE DRAWINGS

FIG. 1 illustrates diagrammatically the steps of a method of template-free enzymatic nucleic acid synthesis using TdT variants of the invention.

DETAILED DESCRIPTION OF THE INVENTION

While the invention is amenable to various modifications and alternative forms, specifics thereof have been shown by way of example in the drawings and will be described in detail. It should be understood that the intention is not to limit the invention to the particular embodiments described. It is the intention to cover all modifications, equivalents, and alternatives falling within the spirit and scope of the invention. Guidance for aspects of the invention is found in many available references and treatises well known to those with ordinary skill in the art, including, for example, Sambrook et al. (1989), Molecular cloning: A Laboratory Manual, Cold Spring Harbor Laboratory, and the like.

The present invention provides variants of the TdT polymerase that can be used for synthesizing polynucleotides, such as DNA or RNA, of predetermined sequences without the use of template strand. The TdT variants of the invention allow modified nucleotides, and more particularly 3'O-reversibly blocked nucleoside triphosphates, to be used in an enzyme-based method of polynucleotide synthesis. The variants of the present invention are described according to their mutations or substitutions at specific residues, whose positions are designated with respect to a specified SEQ ID NO.

TdT variants of the invention are derived from natural TdTs without their BRCT-like N-terminal amino acid sequences. Such truncated sequences are sometimes referred to herein as "truncated wild type" TdTs. More particularly, TdT variants of the invention are derived from the following natural TdTs:

TABLE 1

| Designation | Species | NCBI Accession No. | SEQ ID NO |
|---|---|---|---|
| B10 trunc wt | *Serinus canaria* | XP_030097130.1 | 2 |
| B10 variant | *Serinus canaria* | XP_030097130.1 | 3 |
| B10 tagged variant | *Serinus canaria* | XP_030097130.1 | 4 |
| B19 trunc wt | *Neopelma chrysocephalum* | XP_027527888.1 | 5 |
| B19 variant | *Neopelma chrysocephalum* | XP_027527888.1 | 6 |
| B19 tagged variant | *Neopelma chrysocephalum* | XP_027527888.1 | 7 |
| B57 trunc wt | *Alligator sinensis* | XP_025069068.1 | 8 |
| B57 variant | *Alligator sinensis* | XP_025069068.1 | 9 |
| B57 tagged variant | *Alligator sinensis* | XP_025069068.1 | 10 |
| B59 trunc wt | *Xenopus laevis* | AAI29712.1 | 11 |
| B59 variant | *Xenopus laevis* | AAI29712.1 | 12 |
| B59 tagged variant | *Xenopus laevis* | AAI29712.1 | 13 |
| B63 trunc wt | *Notechis scutatus* | XP_026526500.1 | 14 |
| B63 variant | *Notechis scutatus* | XP_026526500.1 | 15 |
| B63 tagged variant | *Notechis scutatus* | XP_026526500.1 | 16 |
| F15 trunc wt | *Salmo truttal* | XP_029608991.1 | 17 |
| F15 variant | *Salmo truttal* | XP_029608991.1 | 18 |
| F15 tagged variant | *Salmo truttal* | XP_029608991.1 | 19 |
| F24 trunc wt | *Electrophorus electricus* | XP_026869907.1 | 20 |
| F24 variant | *Electrophorus electricus* | XP_026869907.1 | 21 |
| F24 tagged variant | *Electrophorus electricus* | XP_026869907.1 | 22 |
| F32 trunc wt | *Anabas testudineus* | XP_026209749.1 | 23 |
| F32 variant | *Anabas testudineus* | XP_026209749.1 | 24 |
| F32 tagged variant | *Anabas testudineus* | XP_026209749.1 | 25 |
| F57 trunc wt | *Poecilia reticulata* | XP_008428203.1 | 26 |
| F57 variant | *Poecilia reticulata* | XP_008428203.1 | 27 |
| F57 tagged variant | *Poecilia reticulata* | XP_008428203.1 | 28 |
| N100 trunc wt | *Rattus norvegicus* | XP_001012479.1 | 29 |
| N100 variant | *Rattus norvegicus* | XP_001012479.1 | 30 |
| N100 tagged variant | *Rattus norvegicus* | XP_001012479.1 | 31 |
| N100or trunc wt | *Rattus norvegicus* | XP_001012479.1 | 32 |
| N100or variant | *Rattus norvegicus* | XP_001012479.1 | 33 |
| N100or tagged variant | *Rattus norvegicus* | XP_001012479.1 | 34 |
| N14 trunc wt | *Piliocolobus tephrosceles* | XP_023062037.1 | 35 |
| N14 variant | *Piliocolobus tephrosceles* | XP_023062037.1 | 36 |
| N14 tagged variant | *Piliocolobus tephrosceles* | XP_023062037.1 | 37 |
| N27 trunc wt | *Sus scrofa* | XP_003133204.1 | 38 |
| N27 variant | *Sus scrofa* | XP_003133204.1 | 39 |
| N27 tagged variant | *Sus scrofa* | XP_003133204.1 | 40 |
| N35 trunc wt | *Panthera tigris altaica* | XP_007080320.1 | 41 |
| N35 variant | *Panthera tigris altaica* | XP_007080320.1 | 42 |
| N35 tagged variant | *Panthera tigris altaica* | XP_007080320.1 | 43 |
| N72 trunc wt | *Bubalus bubalis* | XP_006061247.1 | 44 |
| N72 variant | *Bubalus bubalis* | XP_006061247.1 | 45 |
| N72 tagged variant | *Bubalus bubalis* | XP_006061247.1 | 46 |
| N93or trunc wt | *Marmota flaviventris* | XP_027786017.1 | 47 |
| N93or variant | *Marmota flaviventris* | XP_027786017.1 | 48 |

TABLE 1-continued

| Designation | Species | NCBI Accession No. | SEQ ID NO |
|---|---|---|---|
| N93or tagged variant | *Marmota flaviventris* | XP_027786017.1 | 49 |

In some embodiments, a TdT variant may be operably linked to a linker moiety including a covalent or non-covalent bond; amino acid tag (e.g., poly-amino acid tag, poly-His tag, 6His-tag); chemical compound (e.g., polyethylene glycol); protein-protein binding pair (e.g., biotin-avidin); affinity coupling; capture probes; or any combination of these. The linker moiety can be separate from or part of a TdT variant (e.g., recombinant His-tagged polymerase, such as exemplified by the following pairs of SEQ ID NOs: (3,4), (6,7), (9,10), (12,13), (15,16), (18,19), (21,22), (24, 25), (27,28), (30,31), (33,34), (36,37), (39,40), (42,43), (45,46) and (48,49)). Typically, the linker moiety does not interfere with the nucleotide binding activity, or catalytic activity of the TdT variant.

In some of the embodiments described above, the efficiency of a variant TdT in incorporating a 3'O-modified nucleoside triphosphate is at least 105 percent that of a previous available TdT wildtype or variant; in other embodiments, the efficiency of a variant TdT in incorporating a 3'O-modified nucleoside triphosphate is at least 110 percent that of a previous available TdT wildtype or variant; in other embodiments, the efficiency of a variant TdT in incorporating a 3'O-modified nucleoside triphosphate is at least 150 percent that of a previous available TdT wildtype or variant.

TdT variants of the invention as described above each comprise an amino acid sequence having a percent sequence identity with a specified SEQ ID NO, subject to the presence of indicated substitutions. In some embodiments, the number and type of sequence differences between a TdT variant of the invention described in this manner and the specified SEQ ID NO may be due to substitutions, deletion and/or insertions, and the amino acids substituted, deleted and/or inserted may comprise any amino acid. In some embodiments, such deletions, substitutions and/or insertions comprise only naturally occurring amino acids. In some embodiments, substitutions comprise only conservative, or synonymous, amino acid changes, as described in Grantham, Science, 185: 862-864 (1974). That is, a substitution of an amino acid can occur only among members of its set of synonymous amino acids. In some embodiments, sets of synonymous amino acids that may be employed are set forth in Table 2A.

TABLE 2A

Synonymous Sets of Amino Acids I

| Amino Acid | Synonymous Set |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Gly, Ala, Thr, Pro, Ser |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Cys, Ser, Thr |
| His | His, Glu, Lys, Gln, Thr, Arg |

TABLE 2A-continued

Synonymous Sets of Amino Acids I

| Amino Acid | Synonymous Set |
|---|---|
| Gln | Gln, Glu, Lys, Asn, His, Thr, Arg |
| Asn | Asn, Gln, Asp, Ser |
| Lys | Lys, Glu, Gln, His, Arg |
| Asp | Asp, Glu, Asn |
| Glu | Glu, Asp, Lys, Asn, Gln, His, Arg |
| Met | Met, Phe, Ile, Val, Leu |
| Trp | Trp |

In some embodiments, sets of synonymous amino acids that may be employed are set forth in Table 2B.

TABLE 2B

Synonymous Sets of Amino Acids II

| Amino Acid | Synonymous Set |
|---|---|
| Ser | Ser |
| Arg | Arg, Lys, His |
| Leu | Ile, Phe, Met, Leu |
| Pro | Ala, Pro |
| Thr | Thr |
| Ala | Pro, Ala |
| Val | Met, Ile Val |
| Gly | Gly |
| Ile | Met, Phe, Val, Leu, Ile |
| Phe | Met, Tyr, Ile, Leu, Phe |
| Tyr | Trp, Met |
| Cys | Cys, Ser |
| His | His, Gln, Arg |
| Gln | Gln, Glu, His |
| Asn | Asn, Asp |
| Lys | Lys, Arg |
| Asp | Asp, Asn |
| Glu | Glu, Gln |
| Met | Met, Phe, Ile, Val, Leu |
| Trp | Trp |

Measurement of Nucleotide Incorporation Activity

The efficiency of nucleotide incorporation by variants of the invention may be measured by an extension, or elongation, assay, e.g. as described in Boule et al (cited below); Bentolila et al (cited below); and Hiatt et al, U.S. Pat. No. 5,808,045, the latter of which is incorporated herein by reference. Briefly, in one form of such an assay, a fluorescently labeled oligonucleotide having a free 3'-hydroxyl is reacted under TdT extension conditions with a variant TdT to be tested for a predetermined duration in the presence of a reversibly blocked nucleoside triphosphate, after which the extension reaction is stopped and the amounts of extension products and unextended initiator oligonucleotide are quantified after separation by gel electrophoresis. By such assays, the incorporation efficiency of a variant TdT may be readily compared to the efficiencies of other variants or to that of wild type or reference TdTs, or other polymerases. In some embodiments, a measure of variant TdT efficiency may be a ratio (given as a percentage) of amount of extended product using the variant TdT over the amount of extended product using wild type TdT in an equivalent assay.

In some embodiments, the following particular extension assay may be used to measure incorporation efficiencies of TdTs: Primer used is the following:

(SEQ ID NO: 50)
5'-AAAAAAAAAAAAAAGGGG-3'

The primer has also an ATTO fluorescent dye on the 5' extremity. Representative modified nucleotides used (noted as dNTP in Table 3) include 3'-O-amino-2',3'-dideoxynucleotides-5'-triphosphates (ONH2, Firebird Biosciences), such as 3'-O-amino-2',3'-dideoxyadenosine-5'-triphosphate. For each different variant tested, one tube is used for the reaction. The reagents are added in the tube, starting from water, and then in the order of Table 3. After 30 min at 37° C. the reaction is stopped by addition of formamide (Sigma).

TABLE 3

Extension Activity Assay Reagents

| Reagent | Concentration | Volume |
| --- | --- | --- |
| $H_2O$ | — | 12 μL |
| Activity buffer | 10x | 2 μL |
| dNTP | 250 μM | 2 μL |
| Purified enzyme | 20 μM | 2 μL |
| Fluorescent primer | 500 nM | 2 μL |

The Activity buffer comprises, for example, TdT reaction buffer (available from New England Biolabs) supplemented with $CoCl_2$.

The product of the assay is analyzed by conventional polyacrylamide gel electrophoresis. For example, products of the above assay may be analyzed in a 16 percent polyacrylamide denaturing gel (Bio-Rad). Gels are made just before the analysis by pouring polyacrylamide inside glass plates and let it polymerize. The gel inside the glass plates is mounted on an adapted tank filed with TBE buffer (Sigma) for the electrophoresis step. The samples to be analyzed are loaded on the top of the gel. A voltage of 500 to 2,000V is applied between the top and bottom of the gel for 3 to 6 h at room temperature. After separation, gel fluorescence is scanned using, for example, a Typhoon scanner (GE Life Sciences). The gel image is analyzed using ImageJ software (imagej.nih.gov/ij/), or its equivalent, to calculate the percentage of incorporation of the modified nucleotides.

Hairpin completion assay. In one aspect, the invention includes methods of measuring the capability of a polymerase, such as a TdT variant, to incorporate a dNTP onto a 3' end of a polynucleotide (i.e. a "test polynucleotide"). One such method comprises providing a test polynucleotide with a free 3' hydroxyl under reaction conditions in which it is substantially only single stranded, but that upon extension with a polymerase, such as a TdT variant, forms a stable hairpin structure comprising a single stranded loop and a double stranded stem, thereby allowing detection of an extension of the 3' end by the presence of the double stranded polynucleotide. The double stranded structure may be detected in a variety of ways including, but not limited to, fluorescent dyes that preferentially fluoresce upon intercalation into the double stranded structure, fluorescent resonance energy transfer (FRET) between an acceptor (or donor) on the extended polynucleotide and a donor (or acceptor) on an oligonucleotide that forms a triplex with the newly formed hairpin stem, FRET acceptors and donors that are both attached to the test polynucleotide and that are brought into FRET proximity upon formation of a hairpin, or the like. In some embodiments, a stem portion of a test polynucleotide after extension by a single nucleotide is in the range of 4 to 6 basepairs in length; in other embodiments, such stem portion is 4 to 5 basepairs in length; and in still other embodiments, such stem portion is 4 basepairs in length. In some embodiments, a test polynucleotide has a length in the range of from 10 to 20 nucleotides; in other embodiments, a test polynucleotide has a length in the range of from 12 to 15 nucleotides. In some embodiments, it is advantageous or convenient to extend the test polynucleotide with a nucleotide that maximizes the difference between the melting temperatures of the stem without extension and the stem with extension; thus, in some embodiments, a test polynucleotide is extended with a dC or dG (and accordingly the test polynucleotide is selected to have an appropriate complementary nucleotide for stem formation).

Exemplary test polynucleotides for hairpin completion assays include p875 (5'-CAGTTAAAACT) (SEQ ID NO: 51) which is completed by extending with a dGTP; p876 (5'-GAGTTAAAACT) (SEQ ID NO: 52) which is completed by extending with a dCTP; and p877 (5'-CAGCAAGGCT) (SEQ ID NO: 53) which is completed by extending with a dGTP. Exemplary reaction conditions for such test polynucleotides may comprise: 2.5-5 μM of test polynucleotide, 1:4000 dilution of GelRed® (intercalating dye from Biotium, Inc., Fremont, CA), 200 mM Cacodylate KOH pH 6.8, 1 mM $CoCl_2$, 0-20% of DMSO and 3' $ONH_2$ dGTP and TdT at desired concentrations. Completion of the hairpin may be monitored by an increase in fluorescence of GelRed® dye using a conventional fluorimeter, such as a TECAN reader at a reaction temperature of 28-38° C., using an excitation filter set to 360 nm and an emission filter set to 635 nm. In some embodiments of this aspect of the invention, TdT variants may be tested for their capacity for template-free incorporate of nucleoside triphosphates by the following steps: (a) combining a test polynucleotide having a free 3'-hydroxyl, a TdT variant and a nucleoside triphosphate under conditions wherein the test polynucleotide is single stranded but upon incorporation of the nucleoside triphosphate forms a hairpin having a double stranded stem region, and (b) detecting the amount of double stranded stem regions formed as a measure of the capacity of the TdT variant to incorporate the nucleoside triphosphate. In some embodiments, the nucleoside triphosphate is a 3'-O-blocked nucleoside triphosphate.

Template-Free Enzymatic Synthesis of Oligonucleotides

Generally, methods of template-free (or equivalently, "template-independent") enzymatic DNA synthesis comprise repeated cycles of steps, such as are illustrated in FIG. 1, in which a predetermined nucleotide is coupled to an initiator or growing chain in each cycle. The general elements of template-free enzymatic synthesis is described in the following references: Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/c6ob01371f (2016); Schmitz et al, Organic Lett., 1(11): 1729-1731 (1999).

Initiator polynucleotides (100) are provided, for example, attached to solid support (102), which have free 3'-hydroxyl groups (103). To the initiator polynucleotides (100) (or elongated initiator polynucleotides in subsequent cycles) are added (104) a 3'-O-protected-dNTP and a template-free polymerase, such as a TdT or variant thereof (e.g. Ybert et al, WO/2017/216472; Champion et al, WO2019/135007) under conditions effective for the enzymatic incorporation of the 3'-O-protected-dNTP onto the 3' end of the initiator polynucleotides (100) (or elongated initiator polynucleotides). This reaction produces elongated initiator polynucleotides whose 3'-hydroxyls are protected (106). If the elongated sequence is not complete, then another cycle of addition is implemented (108). If the elongated initiator polynucleotide contains a competed sequence, then the 3'-O-protection group may be removed, or deprotected, and the desired sequence may be cleaved from the original initiator polynucleotide (110). Such cleavage may be carried out using any of a variety of single strand cleavage techniques, for example, by inserting a cleavable nucleotide at a predetermined location within the original initiator polynucleotide. An exemplary cleavable nucleotide may be a uracil nucleotide which is cleaved by uracil DNA glycosylase. If the elongated initiator polynucleotide does not contain a completed sequence, then the 3'-O-protection groups are removed to expose free 3'-hydroxyls (103) and the elongated initiator polynucleotides are subjected to another cycle of nucleotide addition and deprotection.

As used herein, the terms “protected” and “blocked” in reference to specified groups, such as, a 3'-hydroxyls of a nucleotide or a nucleoside, are used interchangeably and are intended to mean a moiety is attached covalently to the specified group that prevents a chemical change to the group during a chemical or enzymatic process. Whenever the specified group is a 3'-hydroxyl of a nucleoside triphosphate, or an extended fragment (or “extension intermediate”) in which a 3'-protected (or blocked)-nucleoside triphosphate has been incorporated, the prevented chemical change is a further, or subsequent, extension of the extended fragment (or “extension intermediate”) by an enzymatic coupling reaction.

As used herein, an “initiator” (or equivalent terms, such as, “initiating fragment,” “initiator nucleic acid,” “initiator oligonucleotide,” or the like) usually refers to a short oligonucleotide sequence with a free 3'-hydroxyl at its end, which can be further elongated by a template-free polymerase, such as TdT. In one embodiment, the initiating fragment is a DNA initiating fragment. In an alternative embodiment, the initiating fragment is an RNA initiating fragment. In some embodiments, an initiating fragment possesses between 3 and 100 nucleotides, in particular between 3 and 20 nucleotides. In some embodiments, the initiating fragment is single-stranded. In alternative embodiments, the initiating fragment may be double-stranded. In some embodiments, an initiator oligonucleotide may be attached to a synthesis support by its 5'end; and in other embodiments, an initiator oligonucleotide may be attached indirectly to a synthesis support by forming a duplex with a complementary oligonucleotide that is directly attached to the synthesis support, e.g. through a covalent bond. In some embodiments a synthesis support is a solid support which may be a discrete region of a solid planar solid, or may be a bead.

In some embodiments, an initiator may comprise a non-nucleic acid compound having a free hydroxyl to which a TdT may couple a 3'-O-protected dNTP, e.g. Baiga, U.S. patent publications US2019/0078065 and US2019/0078126.

After synthesis is completed polynucleotides with the desired nucleotide sequence may be released from initiators and the solid supports by cleavage. A wide variety of cleavable linkages or cleavable nucleotides may be used for this purpose. In some embodiments, cleaving the desired polynucleotide leaves a natural free 5'-hydroxyl on a cleaved strand; however, in alternative embodiments, a cleaving step may leave a moiety, e.g. a 5'-phosphate, that may be removed in a subsequent step, e.g. by phosphatase treatment. Cleaving steps may be carried out chemically, thermally, enzymatically or by photochemical methods. In some embodiments, cleavable nucleotides may be nucleotide analogs such as deoxyuridine or 8-oxo-deoxyguanosine that are recognized by specific glycosylases (e.g. uracil deoxyglycosylase followed by endonuclease VIII, and 8-oxoguanine DNA glycosylase, respectively). In some embodiments, cleavage may be accomplished by providing initiators with a deoxyinosine as the penultimate 3' nucleotide, which may be cleaved by endonuclease V at the 3' end of the initiator leaving a 5'-phosphate on the released polynucleotide. Further methods for cleaving single stranded polynucleotides are disclosed in the following references, which are incorporated by reference: U.S. Pat. Nos. 5,739,386, 5,700,642 and 5,830,655; and U.S. Patent Publication Nos. 2003/0186226 and 2004/0106728; and in Urdea and Horn, U.S.

In some embodiments, cleavage by glycosylases and/or endonucleases may require a double stranded DNA substrate.

Returning to FIG. 1, in some embodiments, an ordered sequence of nucleotides are coupled to an initiator nucleic acid using a template-free polymerase, such as TdT, in the presence of 3'-O-protected dNTPs in each synthesis step. In some embodiments, the method of synthesizing an oligonucleotide comprises the steps of (a) providing an initiator (e.g. (100)) having a free 3'-hydroxyl (103); (b) reacting (104) under extension conditions the initiator or an extension intermediate having a free 3'-hydroxyl with a template-free polymerase in the presence of a 3'-O-protected nucleoside triphosphate to produce a 3'-O-protected extension intermediate (106); (c) deprotecting the extension intermediate to produce an extension intermediate with a free 3'-hydroxyl; and (d) repeating steps (b) and (c) (108) until the polynucleotide is synthesized (110). (Sometimes the terms “extension intermediate” and “elongation fragment” are used interchangeably). In some embodiments, an initiator is provided as an oligonucleotide attached to a solid support, e.g. by its 5' end. The above method may also include washing steps after the reaction, or extension, step, as well as after the de-protecting step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

When the sequence of polynucleotides on a synthesis support includes reverse complementary subsequences, secondary intra-molecular or cross-molecular structures may be created by the formation of hydrogen bonds between the reverse complementary regions. In some embodiments, base protecting moieties for exocyclic amines are selected so that hydrogens of the protected nitrogen cannot participate in hydrogen bonding, thereby preventing the formation of such secondary structures. That is, base protecting moieties may be employed to prevent the formation of hydrogen bonds, such as are formed in normal base pairing, for example, between nucleosides A and T and between G and C. At the end of a synthesis, the base protecting moieties may be removed and the polynucleotide product may be cleaved from the solid support, for example, by cleaving it from its initiator.

In addition to providing 3'-O-blocked dNTP monomers with base protection groups, elongation reactions may be performed at higher temperatures using thermal stable template-free polymerases. For example, a thermal stable template-free polymerase having activity above 40° C. may be employed; or, in some embodiments, a thermal stable template-free polymerase having activity in the range of from 40-85° C. may be employed; or, in some embodiments, a thermal stable template-free polymerase having activity in the range of from 40-65° C. may be employed.

In some embodiments, elongation conditions may include adding solvents to an elongation reaction mixture that inhibit hydrogen bonding or base stacking. Such solvents include water miscible solvents with low dielectric constants, such as dimethyl sulfoxide (DMSO), methanol, and the like. Likewise, in some embodiments, elongation conditions may include the provision of chaotropic agents that include, but are not limited to, n-butanol, ethanol, guanidinium chloride, lithium perchlorate, lithium acetate, magnesium chloride, phenol, 2-propanol, sodium dodecyl sulfate, thiourea, urea, and the like. In some embodiments, elongation conditions include the presence of a secondary-structure-suppressing amount of DMSO. In some embodiments, elongation conditions may include the provision of DNA binding proteins that inhibit the formation of secondary structures, wherein such proteins include, but are not limited to, single-stranded binding proteins, helicases, DNA glycolases, and the like.

3'-O-blocked dNTPs without base protection may be purchased from commercial vendors or synthesized using published techniques, e.g. U.S. Pat. No. 7,057,026; Guo et al, Proc. Natl. Acad. Sci., 105(27): 9145-9150 (2008); Benner, U.S. Pat. Nos. 7,544,794 and 8,212,020; International patent publications WO2004/005667, WO91/06678; Canard et al, Gene (cited herein); Metzker et al, Nucleic Acids Research, 22: 4259-4267 (1994); Meng et al, J. Org. Chem., 14: 3248-3252 (3006); U.S. patent publication 2005/037991. 3'-O-blocked dNTPs with base protection may be synthesized as described below.

When base-protected dNTPs are employed the above method of FIG. 1 may further include a step (e) removing base protecting moieties, which in the case of acyl or amidine protection groups may (for example) include treating with concentrated ammonia.

The above method may also include capping step(s) as well as washing steps after the reacting, or extending, step, as well as after the deprotecting step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions.

In some embodiments, reaction conditions for an elongation step (also sometimes referred to as an extension step or a coupling step) may comprising the following: 2.0 μM purified TdT; 125-600 μM 3'-O-blocked dNTP (e.g. 3'-O—NH2-blocked dNTP); about 10 to about 500 mM potassium cacodylate buffer (pH between 6.5 and 7.5) and from about 0.01 to about 10 mM of a divalent cation (e.g. $CoCl_2$, or $MnCl_2$), where the elongation reaction may be carried out in a 50 μL reaction volume, at a temperature within the range RT to 45° C., for 3 minutes. In embodiments, in which the 3'-O-blocked dNTPs are 3'-O—NH2-blocked dNTPs, reaction conditions for a deblocking step may comprise the following: 700 mM $NaNO_2$; 1 M sodium acetate (adjusted with acetic acid to pH in the range of 4.8-6.5), where the deblocking reaction may be carried out in a 50 μL volume, at a temperature within the range of RT to 45° C. for 30 seconds to several minutes. Washes may be performed with the cacodylate buffer without the components of the coupling reaction (e.g. enzyme, monomer, divalent cations).

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in the following references, which are incorporated by reference: Benner, U.S. Pat. Nos. 7,544,794 and 8,212,020; 5,808,045; 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite.

As noted above, in some embodiments it is desirable to employ two or more blocking groups that may be removed using orthogonal de-blocking conditions. The following exemplary pairs of blocking groups (Table 4) may be used in parallel synthesis embodiments. It is understood that other blocking group pairs, or groups containing more than two, may be available for use in these embodiments of the invention.

TABLE 4

| Exemplary pairs of blocking groups | |
|---|---|
| 3'-O—NH2 | 3'-O-azidomethyl |
| 3'-O—NH2 | 3'-O-allyl |
| 3'-O—NH2 | 3'-O-phosphate |
| 3'-O-azidomethyl | 3'-O-allyl |
| 3'-O-azidomethyl | 3'-O-phosphate |
| 3'-O-allyl | 3'-O-phosphate |

Synthesizing oligonucleotides on living cells requires mild deblocking, or deprotection, conditions, that is, conditions that do not disrupt cellular membranes, denature proteins, interfere with key cellular functions, or the like. In some embodiments, deprotection conditions are within a range of physiological conditions compatible with cell survival. In such embodiments, enzymatic deprotection is desirable because it may be carried out under physiological conditions. In some embodiments specific enzymatically removable blocking groups are associated with specific enzymes for their removal. For example, ester- or acyl-based blocking groups may be removed with an esterase, such as acetylesterase, or like enzyme, and a phosphate blocking group may be removed with a 3' phosphatase, such as T4 polynucleotide kinase. By way of example, 3'-O-phosphates may be removed by treatment with as solution of 100 mM Tris-HCl (pH 6.5) 10 mM $MgCl_2$, 5 mM 2-mercaptoethanol, and one Unit T4 polynucleotide kinase. The reaction proceeds for one minute at a temperature of 37° C.

A "3'-phosphate-blocked" or "3'-phosphate-protected" nucleotide refers to nucleotides in which the hydroxyl group at the 3'-position is blocked by the presence of a phosphate containing moiety. Examples of 3'-phosphate-blocked nucleotides in accordance with the invention are nucleotidyl-3'-phosphate monoestednucleotidyl-2',3'-cyclic phosphate, nucicotidyl-2'-phosphate monoester and nucleotidyl-2' or 3'-alkylphosphate diester, and nucleotidyl-2' or 3'-pyrophosphate. Thiophosphate or other analogs of such compounds can also be used, provided that the substitution does not prevent dephosphorylation resulting in a free 3'-OH by a phosphatase.

Further examples of synthesis and enzymatic deprotection of 3'-O-ester-protected dNTPs or 3'-O-phosphate-protected dNTPs are described in the following references: Canard et al, Proc. Natl. Acad. Sci., 92:10859-10863 (1995); Canard et al, Gene, 148: 1-6 (1994); Cameron et al, Biochemistry, 16(23): 5120-5126 (1977); Rasolonjatovo et al, Nucleosides & Nucleotides, 18(4&5): 1021-1022 (1999); Ferrero et al, Monatshefte fur Chemie, 131: 585-616 (2000); Taunton-Rigby et al, J. Org. Chem., 38(5): 977-985 (1973); Uemura et al, Tetrahedron Lett., 30(29): 3819-3820 (1989); Becker et al, J. Biol. Chem., 242(5): 936-950 (1967); Tsien, International patent publication WO1991/006678.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

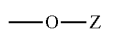

wherein —Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')$_2$ represents a group of formula =C(R"')$_2$ wherein each R"' may be the same or different and is selected from the group comprising hydrogen and halogen atoms and alkyl groups, with the proviso that in some embodiments the alkyl of each R"' has from 1 to 3 carbon atoms; and wherein the molecule may be reacted to yield an intermediate in which each R" is exchanged for H or, where Z is —(R')$_2$—F, the F is exchanged for OH, SH or NH$_2$, preferably OH, which intermediate dissociates under aqueous conditions to afford a molecule with a free 3'-OH; with the proviso that where Z is —C(R')$_2$—S—R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')$_2$—N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less. In some embodiments, Z is an enzymatically cleavable organic moiety with or without heteroatoms having a molecular weight of 200 or less. In other embodiments, Z is an enzymatically cleavable organic moiety with or without heteroatoms having a molecular weight of 100 or less. In other embodiments, Z is an enzymatically cleavable organic moiety with or without heteroatoms having a molecular weight of 50 or less. In other embodiments, Z is an enzymatically cleavable ester group having a molecular weight of 200 or less. In other embodiments, Z is a phosphate group removable by a 3'-phosphatase. In some embodiments, one or more of the following 3'-phosphatases may be used with the manufacturer's recommended protocols: T4 polynucleotide kinase, calf intestinal alkaline phosphatase, recombinant shrimp alkaline phosphatase (e.g. available from New England Biolabs, Beverly, MA)

In a further embodiments, the 3'-blocked nucleotide triphosphate is blocked by either a 3'-O-azidomethyl, 3'-O—NH$_2$ or 3'-O-allyl group. In other embodiments, 3'-O-blocking groups of the invention include 3'-O-methyl, 3'-O-(2-nitrobenzyl), 3'-O-allyl, 3'-O-amine, 3'-O-azidomethyl, 3'-O-tert-butoxy ethoxy, 3'-O-(2-cyanoethyl), 3'-O-nitro, and 3'-O-propargyl. In other embodiments, the 3'-blocked nucleotide triphosphate is blocked by either a 3'-O-azidomethyl or a 3'-O—NH2. Synthesis and use of such 3'-blocked nucleoside triphosphates are disclosed in the following references: U.S. Pat. Nos. 9,410,197; 8,808,988; 6664097; 5744595; 7544794; 8034923; 8212020; 10472383; Guo et al, Proc. Natl. Acad. Sci., 105(27): 9145-9150 (2008); and like references.

In some embodiments, 3'-O— protection groups are electrochemically labile groups. That is, deprotection or cleavage of the protection group is accomplished by changing the electrochemical conditions in the vicinity of the protection group which result in cleavage. Such changes in electrochemical conditions may be brought about by changing or applying a physical quantity, such as a voltage difference or light to activate auxiliary species which, in turn, cause changes in the electrochemical conditions at the site of the protection group, such as an increase or decrease in pH. In some embodiments, electrochemically labile groups include, for example, pH-sensitive protection groups that are cleaved whenever the pH is changed to a predetermined value. In other embodiments, electrochemically labile groups include protecting groups which are cleaved directly whenever reducing or oxidizing conditions are changed, for example, by increasing or decreasing a voltage difference at the site of the protection group.

Production of Variant TdTs

Variants of the invention may be produced by mutating known reference or wild type TdT-coding polynucleotides, then expressing it using conventional molecular biology techniques. For example, a desired gene or DNA fragment encoding a polypeptide of desired sequence may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or such gene or DNA fragment may be directly cloned from cells of a selected species using conventional protocols, e.g.

described by Boule et al, Mol. Biotechnology, 10: 199-208 (1998), or Bentolila et al, EMBO J., 14: 4221-4229 (1995); or the like.

An isolated gene encoding a desired TdT variant may be inserted into an expression vector, such as pET32 (Novagen) to give an expression vector which then may be used to make and express variant TdT proteins using conventional protocols. Vectors with the correct sequence may be transformed in *E. coli* producer strains.

Transformed strains are cultured using conventional techniques to pellets from which TdT protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h30 at 10,000 rpm. Centrifugate is pass through a 0.2 μm filter to remove any debris before column purification.

TdT protein may be purified from the centrifugate in a one-step affinity procedure. For example, Ni-NTA affinity column (GE Healthcare) may be used to bind the TdT polymerases. Initially the column is washed and equilibrated with 15 column volumes of 50 mM tris-HCL (Sigma) pH 7.5, 150 mM NaCl (Sigma) and 20 mM imidazole (Sigma). TdT polymerases are bound to the column after equilibration; then, a washing buffer, for example, composed of 50 mM tris-HCL (Sigma) pH 7.5, 500 mM NaCl (Sigma) and 20 mM imidazole (Sigma), may be applied to the column for 15 column volumes. After such washing, the TdT polymerases are eluted with 50 mM tris-HCL (Sigma) pH 7.5, 500 mM NaCl (Sigma) and 0.5M imidazole (Sigma). Fractions corresponding to the highest concentration of TdT polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 μL of various fraction of the purified enzymes are analyzed in SDSPAGE gels.

In some embodiments, a TdT variant may be operably linked to a linker moiety including a covalent or non-covalent bond; amino acid tag (e.g., poly-amino acid tag, poly-His tag, 6His-tag, or the like); chemical compound (e.g., polyethylene glycol); protein-protein binding pair (e.g., biotin-avidin); affinity coupling; capture probes; or any combination of these. The linker moiety can be separate from or part of a TdT variant. An exemplary His-tag for use with TdT variants of the invention is MASSHHHHHHSSGSENLYFQTGSSG- (SEQ ID NO: 54)). The tag-linker moiety does not interfere with the nucleotide binding activity, or catalytic activity of the TdT variant.

The above processes, or equivalent processes, result in an isolated TdT variant that may be mixed with a variety of reagents, such as, salts, pH buffers, carrier compounds, and the like, that are necessary or useful for activity and/or preservation.

Kits for Practicing Methods of the Invention

The invention includes a variety of kits for practicing methods of the invention. In one aspect, kits of the invention comprise a TdT variant of the invention in a formulation suitable for carrying out template-free enzymatic polynucleotide synthesis as described herein. Such kits may also include synthesis buffers that provide reaction conditions for optimizing the template-free addition or incorporation of a 3'-O-protected dNTP to a growing strand. In some embodiments, kits of the invention further include 3'-O-reversibly protected dNTPs. In such embodiments, the 3'-O-reversibly protected dNTPs may comprise 3'-O-amino-dNTPs or 3'-O-azidomethyl-dNTPs. In further embodiments, kits may include one or more of the following items, either separately or together with the above-mentioned items: (i) deprotection reagents for carrying out a deprotecting step as described herein, (ii) solid supports with initiators attached thereto, (iii) cleavage reagents for releasing completed polynucleotides from solid supports, (iv) wash reagents or buffers for removing unreacted 3'-O-protected dNTPs at the end of an enzymatic addition or coupling step, and (v) post-synthesis processing reagents, such as purification columns, desalting reagents, eluting reagents, and the like. In some embodiments, kits of the invention may include arrays of reaction wells for carrying out multiple synthesis reactions in a single operation. In some embodiments, such arrays may be conventional filter plates comprising 24-, 48-, 96-, 384- or 1536-wells.

In regard to items (ii) and (iii) above, certain initiators and cleavage reagents go together. For example, an initiator comprising an inosine cleavable nucleotide may come with an endonuclease V cleavage reagent; an initiator comprising a nitrobenzyl photocleavable linker may come with a suitable light source for cleaving the photocleavable linker; an initiator comprising a uracil may come with a uracil DNA glycosylase cleavage reagent; and the like.

Example 1

Testing Incorporation Activity of TdT Variants

TdT variants listed in Table 5 were prepared using conventional techniques, purified and tested in two separate hairpin assays as described above using 3'-O-amino-2'-deoxynucleoside triphosphate monomers. Their performance in the assays was compared to that of a mouse-bovine chimeric TdT (designated M57, SEQ ID NO: 55) known to have a high incorporation rate.

TABLE 5

| Designation | SEQ ID NO | mg/ml expression | Hairpin + G (% M57) | Hairpin + C (% M57) | 3'-OH (no addition) (% M57) |
|---|---|---|---|---|---|
| B10 | 4 | 2.3 | 34 | 36 | 25 |
| B19 | 7 | 1.0 | 83 | 107 | 42 |
| B57 | 10 | 0.8 | 34 | 91 | 62 |
| B59 | 13 | 2.8 | 9 | −73 | −1 |
| B63 | 16 | 2.8 | 21 | 162 | 41 |
| F15 | 19 | 7.3 | 54 | 625 | 85 |
| F24 | 22 | 5.0 | 25 | 324 | 85 |
| F32 | 25 | 5.8 | 35 | 536 | 91 |
| F57 | 28 | 0.4 | 15 | 172 | 24 |
| N100 | 31 | 8.1 | 31 | 90 | 10 |
| N100or | 34 | 6.2 | 53 | 362 | 28 |
| N14 | 37 | 2.8 | 69 | 510 | 96 |

TABLE 5-continued

| Designation | SEQ ID NO | mg/ml expression | Hairpin + G (% M57) | Hairpin + C (% M57) | 3'-OH (no addition) (% M57) |
|---|---|---|---|---|---|
| N27 | 40 | 4.3 | 111 | 363 | 85 |
| N35 | 43 | 2.8 | 70 | 480 | 101 |
| N72 | 46 | 1.2 | 70 | 222 | 87 |
| N93or | 49 | 0.4 | 37 | 267 | 61 |
| M57 | 55 | 8.9 | 100 | 100 | 100 |

As can be seen from the data many of the TdT variants have coupling efficiencies much greater than the standard, M57. Reactions were carried out in presence of low concentration of 3' terminated dNTPs (20 μM), so the increases are mostly attributed to better affinity towards particular dNTP. Expression levels correspond to protein concentration after elution from Ni-NTA (300 μL total, derived from 50 ml culture).

Definitions

Amino acids are represented by either their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

"Functionally equivalent" in reference to a substituted residue means the substituted residue of a variant TdT has an identical functional role as a residue in a sequence of another TdT having a sequence homologous to SEQ ID NO: 1. Functionally equivalent residues may be identified by using sequence alignments, for example, using the Mutalin line alignment software (http://multalin.toulouse.inra.fr/multalin/multalin.html; 1988, Nucl. Acids Res., 16 (22), 25 10881-10890). After alignment, the functionally equivalent residues are at homologous positions on the different sequences considered. Sequence alignments and identification of functionally equivalent residues may be determined between any TdT and their natural variants, including interspecies.

"Isolated" in reference to protein means such a compound which has been identified and separated and/or recovered from a component of its natural environment or from a heterogeneous reaction mixture. Contaminant components of a natural environment or reaction mixture are materials which would interfere with a protein's function, and may include enzymes, hormones, and other proteinaceous or nonproteinaceous solutes. In some embodiments, a protein of the invention is purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. When manufactured by recombinant methodologies, an isolated protein of the invention may include the protein of the invention in situ within recombinant cells since at least one component of the protein's natural environment will not be present. Ordinarily, an isolated protein of the invention is prepared by at least one purification step.

"Kit" refers to any delivery system for delivering materials or reagents for carrying out a method of the invention. In the context of reaction assays, such delivery systems include systems and/or compounds (such as dilutants, surfactants, carriers, or the like) that allow for the storage, transport, or delivery of reaction reagents (e.g., one or more TdT variants, reaction buffers, 3'-O-protected-dNTPs, deprotection reagents, solid suppprts with initiators attached, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain one or more TdT variants for use in a synthesis method, while a second or additional containers may contain deprotection agents, solid supports with initiators, 3'-O-protected dNTPs, or the like.

"Mutant" or "variant," which are used interchangeably, refer to polypeptides derived from a natural or reference TdT polypeptide described herein, and comprising a modification or an alteration, i.e., a substitution, insertion, and/or deletion, at one or more positions. Variants may be obtained by various techniques well known in the art. In particular, examples of techniques for altering the DNA sequence encoding the wild-type protein, include, but are not limited to, site-directed mutagenesis, random mutagenesis, sequence shuffling and synthetic oligonucleotide construction. Mutagenesis activities consist in deleting, inserting or substituting one or several amino-acids in the sequence of a protein or in the case of the invention of a polymerase. The following terminology is used to designate a substitution: L238A denotes that amino acid residue (Leucine, L) at position 238 of a reference, or wild type, sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/or ttp://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

The invention claimed is:

1. A terminal deoxynucleotidyl transferase (TdT) variant comprising an amino acid sequence at least ninety percent identical to an amino acid sequence selected from SEQ ID NO: 2, 5, 8, 11, 14, 17, 20, 23 26, 29, 32, 35, 38, 41, 44 or 47, wherein:

with respect to SEQ ID NO: 2 leucine at position 61 is substituted, cysteine at position 170 is substituted, arginine at position 204 is substituted, arginine at position 326 is substituted and glycine at position 329 is substituted;

with respect to SEQ ID NO: 5 leucine at position 48 is substituted, cysteine at position 158 is substituted, arginine at position 192 is substituted, arginine at position 314 is substituted and glycine at position 317 is substituted;

with respect to SEQ ID NO: 8 leucine at position 61 is substituted, tyrosine at position 171 is substituted, arginine at position 205 is substituted, arginine at position 327 is substituted and glutamic acid at position 329 is substituted;

with respect to SEQ ID NO: 11 leucine at position 61 is substituted, tyrosine at position 171 is substituted, arginine at position 205 is substituted, arginine at position 324 is substituted and glutamic acid at position 327 is substituted;

with respect to SEQ ID NO: 14 glycine at position 61 is substituted, arginine at position 205 is substituted, arginine at position 327 is substituted and glutamic acid at position 330 is substituted;

with respect to SEQ ID NO: 17 arginine at position 61 may or may not be substituted, alanine at position 158 is substituted, arginine at position 192 is substituted, arginine at position 311 is substituted and glutamic acid at position 314 is substituted;

with respect to SEQ ID NO: 20 arginine at position 61 may or may not be substituted, proline at position 171 may or may not be substituted, arginine at position 205 is substituted, threonine at position 321 is substituted and glutamic acid at position 324 is substituted;

with respect to SEQ ID NO: 23 arginine at position 61 may or may not be substituted, alanine at position 171 may or may not be substituted, arginine at position 205 is substituted, alanine at position 322 may or may not be substituted and glutamic acid at position 325 is substituted;

with respect to SEQ ID NO: 26 arginine at position 61 may or may not be substituted, alanine at position 171 may or may not be substituted, arginine at position 205 is substituted, arginine at position 322 is substituted and glutamic acid at position 325 is substituted;

with respect to SEQ ID NO: 29 methionine at position 48 is substituted, cysteine at position 158 is substituted, arginine at position 192 is substituted, arginine at position 310 is substituted and glutamic acid at position 313 is substituted;

with respect to SEQ ID NO: 32 methionine at position 61 is substituted, cysteine at position 171 is substituted, arginine at position 205 is substituted, arginine at position 323 is substituted and glutamic acid at position 326 is substituted;

with respect to SEQ ID NO: 35 methionine at position 61 is substituted, cysteine at position 171 is substituted, arginine at position 205 is substituted, arginine at position 323 is substituted and glutamic acid at position 326 is substituted;

with respect to SEQ ID NO: 38 methionine at position 61 is substituted, cysteine at position 171 is substituted, arginine at position 205 is substituted, arginine at position 323 is substituted and glutamic acid at position 326 is substituted;

with respect to SEQ ID NO: 41 methionine at position 61 is substituted, cysteine at position 171 is substituted, arginine at position 205 is substituted, arginine at position 323 is substituted and glutamic acid at position 326 is substituted;

with respect to SEQ ID NO: 44 methionine at position 48 is substituted, cysteine at position 158 is substituted, arginine at position 192 is substituted, arginine at position 309 is substituted and glutamic acid at position 312 is substituted; or with respect to SEQ ID NO: 47 methionine at position 61 is substituted, cysteine at position 171 is substituted, arginine at position 205 is substituted, arginine at position 323 is substituted and glutamic acid at position 326 is substituted; and wherein the TdT variant (i) is capable of synthesizing a nucleic acid fragment without a template and (ii) (ii) is capable of incorporating a 3'-O-modified nucleotide onto a free 3'-hydroxyl of a nucleic acid fragment.

2. The TdT variant of claim 1, wherein:

said substitution for leucine at position 61 in SEQ ID NO: 2, 8 or 11 or position 48 in SEQ ID NO: 5 is selected from the group consisting of R or Q;

said substitution for cysteine at position 170 in SEQ ID NO: 2 or position 158 in SEQ ID NO: 5, 29 or 44 or position 171 in SEQ ID NO: 32, 35, 38, 41 or 47 is selected from the group consisting of G, R, P, A, V, S, N, Q or D; and in other embodiments, the substitution for cysteine at the foregoing positions is selected from the group consisting of G or R;

said substitution for tyrosine at position 171 of SEQ ID NO: 8 or 11 is selected from the group consisting of G, R, P, A, V, S, N, Q or D; and in other embodiments, the substitution for tyrosine at the foregoing positions is selected from the group consisting of G or R;

said substitution for alanine at position 158 of SEQ ID NO: 17 or position 171 of SEQ ID NO: 23 or 26 is selected from the group consisting of G, R, P, V, S, N, Q or D; and in other embodiments, the substitution for alanine at the foregoing positions is selected from the group consisting of G or R;

said substitution for proline at position 171 of SEQ ID NO: 20 is selected from the group consisting of G, R, A, V, S, N, Q or D; and in other embodiments, the substitution for tyrosine at the foregoing positions is selected from the group consisting of G or R;

said substitution for arginine at position 204 of SEQ ID NO: 2 or position 192 of SEQ ID NO: 5, 17, 29 or 44 or position 205 of SEQ ID NO: 8, 11, 14, 20, 23, 26, 32, 35, 38, 41 or 47 is selected from the group consisting of L or N;

said substitution for arginine at position 326 of SEQ ID NO: 2 or position 314 of SEQ ID NO: 5 or position 327 of SEQ ID NO: 8 or 14 or position 324 of SEQ ID NO: 11 or position 311 of SEQ ID NO: 17 or position 321 of SEQ ID NO: 20 or position 322 of SEQ ID NO: 23 or 26 or position 310 of SEQ ID NO: 29 or position 323 of SEQ ID NO: 32, 35, 38, 41 or 47 or position 309 of SEQ ID NO: 44 is selected from the group consisting of P, N or A;

said substitution for threonine at position 321 of SEQ ID NO: 20 is selected from the group consisting of P, N or A;

said substitution for glycine at position 329 of SEQ ID NO: 2 or 5 is selected from the group consisting of N, L, T or S; or said substitution for glutamic acid at position 330 of SEQ ID NO: 8 or 14 or position 327 of SEQ ID NO: 11 or position 311 of SEQ ID NO: 17 or position 324 of SEQ ID NO: 20 or position 325 of SEQ ID NO: 23 or 26 or position 313 of SEQ ID NO: 29 position 326 of SEQ ID NO: 32, 35, 38, 41 or 47 or position 312 of SEQ ID NO: 44 is selected from the group consisting of N, L, T or S.

3. The TdT variant of claim 1, wherein:

with respect to SEQ ID NO: 2 glutamine at position 327 is substituted;

with respect to SEQ ID NO: 5 glutamic acid at position 315 is substituted;

with respect to SEQ ID NO: 8 glutamine at position 328 is substituted;

with respect to SEQ ID NO: 11 glutamine at position 325 is substituted;

with respect to SEQ ID NO: 14 glutamine at position 328 is substituted;

with respect to SEQ ID NO: 17 glutamine at position 312 is substituted;

with respect to SEQ ID NO: 20 glutamine at position 322 is substituted;

with respect to SEQ ID NO: 23 glutamine at position 323 is substituted;

with respect to SEQ ID NO: 26 methionine at position 323 is substituted;

with respect to SEQ ID NO: 29 glutamine at position 311 is substituted;

with respect to SEQ ID NO: 32 glutamine at position 324 is substituted;

with respect to SEQ ID NO: 35 glutamine at position 324 is substituted;

with respect to SEQ ID NO: 38 glutamine at position 324 is substituted;

with respect to SEQ ID NO: 41 glutamine at position 324 is substituted;

with respect to SEQ ID NO: 44 glutamine at position 310 is substituted; or with respect to SEQ ID NO: 47 glutamine at position 324 is substituted.

4. The TdT variant of claim 3, wherein said glutamine is substituted with an amino acid selected from the group consisting of T, F, L, M, I, V and Y.

5. The TdT variant of claim 1, wherein said 3'-O-modified nucleotide is selected from the group consisting of 3'-O-amino-2'-deoxynucleoside triphosphate, 3'-O-azidomethyl-2'-deoxynucleoside triphosphate and 3'-O-allyl-2'-deoxynucleoside triphosphate.

6. A terminal deoxynucleotidyl transferase (TdT) variant comprising an amino acid sequence at least ninety percent identical to an amino acid sequence selected from SEQ ID NO: 3, 6, 9, 12, 15, 18, 21, 24, 27, 30, 33, 36, 39, 42, 45 or 48, wherein:

with respect to SEQ ID NO: 3 amino acid position 61 is R, amino acid position 171 is R, amino acid position 205 is L, amino acid position 327 is A, and amino acid position 330 is N;

with respect to SEQ ID NO: 6 amino acid position 48 is R, amino acid position 158 is R, amino acid position 192 is L, amino acid position 314 is P, and amino acid position 317 is N;

with respect to SEQ ID NO: 9 amino acid position 61 is R, amino acid position 171 is R, amino acid position 205 is L, amino acid position 327 is A, and amino acid position 330 is N;

with respect to SEQ ID NO: 12 amino acid position 61 is R, amino acid position 171 is A, amino acid position 205 is L, amino acid position 324 is P, and amino acid position 327 is N;

with respect to SEQ ID NO: 15 amino acid position 61 is R, amino acid position 171 is R, amino acid position 205 is L, amino acid position 328 is P, and amino acid position 331 is N;

with respect to SEQ ID NO: 18 amino acid position 48 is R, amino acid position 158 is R, amino acid position 192 is L, amino acid position 311 is P, and amino acid position 314 is N;

with respect to SEQ ID NO: 21 amino acid position 61 is R, amino acid position 171 is P, amino acid position 205 is L, amino acid position 321 is A, and amino acid position 324 is N;

with respect to SEQ ID NO: 24 amino acid position 61 is R, amino acid position 171 is A, amino acid position 205 is L, amino acid position 322 is A, and amino acid position 325 is N;

with respect to SEQ ID NO: 27 amino acid position 61 is R, amino acid position 171 is R, amino acid position 205 is L, amino acid position 327 is A, and amino acid position 330 is N;

with respect to SEQ ID NO: 30 amino acid position 48 is R, amino acid position 158 is R, amino acid position 192 is L, amino acid position 310 is P, and amino acid position 313 is N;

with respect to SEQ ID NO: 33 amino acid position 61 is R, amino acid position 171 is R, amino acid position 205 is L, amino acid position 323 is P, and amino acid position 326 is N;

with respect to SEQ ID NO: 36 amino acid position 61 is R, amino acid position 171 is R, amino acid position 205 is L, amino acid position 323 is A, and amino acid position 326 is N;

with respect to SEQ ID NO: 39 amino acid position 61 is R, amino acid position 171 is R, amino acid position 205 is L, amino acid position 323 is P, and amino acid position 326 is N;

with respect to SEQ ID NO: 42 amino acid position 61 is R, amino acid position 171 is R, amino acid position 205 is L, amino acid position 323 is A, and amino acid position 326 is N;

with respect to SEQ ID NO: 45 amino acid position 48 is R, amino acid position 158 is R, amino acid position 192 is L, amino acid position 310 is A, and amino acid position 313 is N; or with respect to SEQ ID NO: 48 amino acid position 61 is R, amino acid position 171 is R, amino acid position 205 is L, amino acid position 323 is P, and amino acid position 326 is N; and wherein the TdT variant (i) is capable of synthesizing a nucleic acid fragment without a template and (ii) (ii) is capable of incorporating a 3'-O-modified nucleotide onto a free 3'-hydroxyl of a nucleic acid fragment.

7. The TdT variant of claim 6, wherein:

with respect to SEQ ID NO: 3 amino acid position 328 is Q or is selected from the group consisting of T, F, L or M;

with respect to SEQ ID NO: 6 amino acid position 315 is Q or is selected from the group consisting of T, F, L or M;

with respect to SEQ ID NO: 9 amino acid position 328 is Q or is selected from the group consisting of T, F, L or M;

with respect to SEQ ID NO: 12 amino acid position 325 is Q or is selected from the group consisting of T, F, L or M;

with respect to SEQ ID NO: 15 amino acid position 329 is Q or is selected from the group consisting of T, F, L or M;

with respect to SEQ ID NO: 18 amino acid position 312 is Q or is selected from the group consisting of T, F, L or M;

with respect to SEQ ID NO: 21 amino acid position 322 is Q or is selected from the group consisting of T, F, L or M;

with respect to SEQ ID NO: 24 amino acid position 323 is Q or is selected from the group consisting of T, F, L or M;

with respect to SEQ ID NO: 27 amino acid position 328 is Q or is selected from the group consisting of T, F, L or M;

with respect to SEQ ID NO: 30 amino acid position 311 is Q or is selected from the group consisting of T, F, L or M;

with respect to SEQ ID NO: 33 amino acid position 324 is Q or is selected from the group consisting of T, F, L or M;

with respect to SEQ ID NO: 36 amino acid position 324 is Q or is selected from the group consisting of T, F, L or M;

with respect to SEQ ID NO: 39 amino acid position 324 is Q or is selected from the group consisting of T, F, L or M;

with respect to SEQ ID NO: 42 amino acid position 324 is Q or is selected from the group consisting of T, F, L or M;

with respect to SEQ ID NO: 45 amino acid position 311 is Q or is selected from the group consisting of T, F, L or M; or with respect to SEQ ID NO: 48 amino acid position 324 is Q or is selected from the group consisting of T, F, L or M.

8. The TdT variant of claim 6 wherein said 3'-O-modified nucleotide is selected from the group consisting of 3'-O-amino-2'-deoxynucleoside triphosphate, 3'-O-azidomethyl-2'-deoxynucleoside triphosphate and 3'-O-allyl-2'-deoxynucleoside triphosphate.

9. A terminal deoxynucleotidyl transferase (TdT) variant comprising an amino acid sequence at least ninety percent identical to an amino acid sequence selected from SEQ ID NO: 3, 6, 9, 12, 15, 18, 21, 24, 27, 30, 33, 36, 39, 42, 45 or 48, and wherein the TdT variant (i) is capable of synthesizing a nucleic acid fragment without a template and (ii) is capable of incorporating a 3'-O-modified nucleotide onto a free 3'-hydroxyl of a polynucleotide.

* * * * *

SEQUENCE LISTING

<160> NUMBER OF SEQ ID NOS: 55

<210> SEQ ID NO 1
<211> LENGTH: 510

-continued

<212> TYPE: PRT
<213> ORGANISM: ARTIFICIAL SEQUENCE
<220> FEATURE:
<223> OTHER INFORMATION: Wild type mouse TdT

<400> SEQUENCE: 1

```
Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

Ala Thr Glu Asp Glu Glu Gln Gln Leu Leu His Lys Val Thr Asp Phe
        355                 360                 365

Trp Lys Gln Gln Gly Leu Leu Leu Tyr Cys Asp Ile Leu Glu Ser Thr
    370                 375                 380
```

-continued

```
Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
            420                 425                 430

Val Asp Leu Val Met Cys Pro Tyr Asp Arg Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Glu Ile Phe Ala
                485                 490                 495

His Leu Gly Leu Asp Tyr Ile Glu Pro Trp Glu Arg Asn Ala
            500                 505                 510


<210> SEQ ID NO 2
<211> LENGTH: 382
<212> TYPE: PRT
<213> ORGANISM: ARTIFICIAL SEQUENCE
<220> FEATURE:
<223> OTHER INFORMATION: B10: trunc wt serinus canaria TdT

<400> SEQUENCE: 2

Ser Pro Pro Leu Asn Thr Pro Glu Leu Glu Met Pro Ser Phe Ile Ala
1               5                   10                  15

Thr Lys Val Ser Gln Tyr Ser Cys Gln Arg Lys Thr Thr Leu Asn Asn
            20                  25                  30

Tyr Asn Lys Lys Phe Thr Asp Ala Phe Glu Val Met Ala Glu Asn Tyr
        35                  40                  45

Glu Phe Lys Glu Asn Glu Ile Phe Cys Leu Glu Phe Leu Arg Ala Ala
    50                  55                  60

Ser Leu Leu Lys Ser Leu Pro Phe Ser Val Thr Arg Met Lys Asp Ile
65                  70                  75                  80

Gln Gly Leu Pro Cys Met Gly Asp Gln Val Arg Asp Val Ile Glu Ile
                85                  90                  95

Ile Glu Glu Gly Glu Ser Ser Arg Val Lys Glu Val Leu Asn Asp Glu
            100                 105                 110

Arg Tyr Lys Ala Phe Lys Gln Phe Thr Ser Val Phe Gly Val Gly Val
        115                 120                 125

Lys Thr Ser Glu Lys Trp Tyr Arg Met Gly Leu Arg Thr Val Gly Glu
    130                 135                 140

Val Lys Ala Asp Lys Thr Leu Lys Leu Ser Lys Met Gln Lys Ala Gly
145                 150                 155                 160

Phe Leu Tyr Tyr Glu Asp Leu Val Ser Cys Val Ser Lys Ala Glu Ala
                165                 170                 175

Asp Ala Val Ser Leu Ile Val Lys Asn Thr Val Cys Thr Phe Leu Pro
            180                 185                 190

Asp Ala Leu Val Thr Ile Thr Gly Gly Phe Arg Arg Gly Lys Asn Ile
        195                 200                 205

Gly His Asp Ile Asp Phe Leu Ile Thr Asn Pro Gly Pro Arg Glu Asp
    210                 215                 220

Asp Glu Leu Leu His Lys Val Ile Asp Leu Trp Lys Lys Gln Gly Leu
225                 230                 235                 240
```

-continued

```
Leu Leu Tyr Cys Asp Ile Ile Glu Ser Thr Phe Val Lys Glu Gln Leu
                245                 250                 255

Pro Ser Arg Lys Ile Asp Ala Met Asp His Phe Gln Lys Cys Phe Ala
            260                 265                 270

Ile Leu Lys Leu Tyr Gln Pro Arg Val Asp Asn Ser Thr Cys Asn Thr
        275                 280                 285

Ser Lys Lys Leu Glu Met Ala Glu Val Lys Asp Trp Lys Ala Ile Arg
    290                 295                 300

Val Asp Leu Val Ile Thr Pro Phe Glu Gln Tyr Ser Tyr Ala Leu Leu
305                 310                 315                 320

Gly Trp Thr Gly Ser Arg Gln Phe Gly Arg Asp Leu Arg Arg Tyr Ala
                325                 330                 335

Ala His Glu Arg Arg Met Ile Leu Asp Asn His Gly Leu Tyr Asp Arg
            340                 345                 350

Thr Lys Arg Ile Phe Leu Lys Ala Gly Ser Glu Glu Glu Ile Phe Ala
        355                 360                 365

His Leu Gly Leu Asp Tyr Val Glu Pro Trp Glu Arg Asn Ala
    370                 375                 380


<210> SEQ ID NO 3
<211> LENGTH: 383
<212> TYPE: PRT
<213> ORGANISM: ARTIFICIAL SEQUENCE
<220> FEATURE:
<223> OTHER INFORMATION: B10 trunc new

<400> SEQUENCE: 3

Ser Pro Ser Pro Val Pro Gly Ser Gln Asn Val Pro Ala Pro Ser Val
1               5                   10                  15

Thr Lys Val Ser Gln Tyr Ser Cys Gln Arg Lys Thr Thr Leu Asn Asn
            20                  25                  30

Tyr Asn Lys Lys Phe Thr Asp Ala Phe Glu Val Met Ala Glu Asn Tyr
        35                  40                  45

Glu Phe Lys Glu Asn Glu Glu Ser Arg Asp Ala Phe Arg Arg Ala Ala
    50                  55                  60

Ser Leu Leu Lys Ser Leu Pro Phe Pro Val Thr Arg Met Lys Asp Ile
65                  70                  75                  80

Gln Gly Leu Pro Cys Met Gly Asp Gln Val Arg Arg Ile Ile Glu Glu
                85                  90                  95

Ile Ile Glu Glu Gly Glu Ser Ser Arg Val Lys Glu Val Leu Asn Asp
            100                 105                 110

Glu Arg Tyr Lys Ala Phe Lys Gln Phe Thr Ser Val Phe Gly Val Gly
        115                 120                 125

Arg Lys Thr Ser Glu Lys Trp Tyr Arg Met Gly Leu Arg Thr Val Glu
    130                 135                 140

Glu Val Lys Ala Asp Lys Thr Leu Lys Leu Ser Lys Met Gln Lys Ala
145                 150                 155                 160

Gly Phe Leu Tyr Tyr Glu Asp Leu Val Ser Arg Val Ser Lys Ala Glu
                165                 170                 175

Ala Asp Ala Val Ser Leu Ile Val Lys Asn Thr Val Val Thr Phe Leu
            180                 185                 190

Pro Asp Ala Leu Val Thr Ile Thr Gly Gly Phe Arg Leu Gly Lys Lys
        195                 200                 205

Ile Gly His Asp Ile Asp Phe Leu Ile Thr Asn Pro Gly Pro Arg Glu
    210                 215                 220
```

```
Asp Glu Glu Leu Leu His Lys Val Ile Asp Leu Trp Lys Lys Gln Gly
225                 230                 235                 240

Leu Leu Leu Tyr Cys Asp Ile Ile Glu Ser Thr Phe Val Lys Glu Gln
                245                 250                 255

Leu Pro Ser Arg Lys Val Asp Ala Met Asp His Phe Gln Lys Cys Phe
            260                 265                 270

Ala Ile Leu Lys Leu Tyr Gln Pro Arg Val Asp Asn Ser Thr Ser Asn
        275                 280                 285

Thr Ser Lys Lys Leu Glu Met Ala Glu Val Lys Asp Trp Lys Ala Ile
    290                 295                 300

Arg Val Asp Leu Val Ile Thr Pro Phe Glu Gln Tyr Ala Tyr Ala Leu
305                 310                 315                 320

Leu Gly Trp Thr Gly Ser Ala Phe Phe Asn Arg Asp Leu Arg Arg Tyr
                325                 330                 335

Ala Ser His Glu Arg Lys Met Ile Leu Asp Asn His Ala Leu Tyr Asp
            340                 345                 350

Arg Arg Lys Arg Ile Phe Leu Lys Ala Gly Ser Glu Glu Glu Ile Phe
        355                 360                 365

Ala His Leu Gly Leu Asp Tyr Val Glu Pro Trp Glu Arg Asn Ala
    370                 375                 380


<210> SEQ ID NO 4
<211> LENGTH: 408
<212> TYPE: PRT
<213> ORGANISM: ARTIFICIAL SEQUENCE
<220> FEATURE:
<223> OTHER INFORMATION: B10

<400> SEQUENCE: 4

Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30

Ser Gln Asn Val Pro Ala Pro Ser Val Thr Lys Val Ser Gln Tyr Ser
        35                  40                  45

Cys Gln Arg Lys Thr Thr Leu Asn Asn Tyr Asn Lys Lys Phe Thr Asp
    50                  55                  60

Ala Phe Glu Val Met Ala Glu Asn Tyr Glu Phe Lys Glu Asn Glu Glu
65                  70                  75                  80

Ser Arg Asp Ala Phe Arg Arg Ala Ala Ser Leu Leu Lys Ser Leu Pro
                85                  90                  95

Phe Pro Val Thr Arg Met Lys Asp Ile Gln Gly Leu Pro Cys Met Gly
            100                 105                 110

Asp Gln Val Arg Arg Ile Ile Glu Glu Ile Ile Glu Glu Gly Glu Ser
        115                 120                 125

Ser Arg Val Lys Glu Val Leu Asn Asp Glu Arg Tyr Lys Ala Phe Lys
    130                 135                 140

Gln Phe Thr Ser Val Phe Gly Val Gly Arg Lys Thr Ser Glu Lys Trp
145                 150                 155                 160

Tyr Arg Met Gly Leu Arg Thr Val Glu Glu Val Lys Ala Asp Lys Thr
                165                 170                 175

Leu Lys Leu Ser Lys Met Gln Lys Ala Gly Phe Leu Tyr Tyr Glu Asp
            180                 185                 190

Leu Val Ser Arg Val Ser Lys Ala Glu Ala Asp Ala Val Ser Leu Ile
        195                 200                 205
```

```
Val Lys Asn Thr Val Val Thr Phe Leu Pro Asp Ala Leu Val Thr Ile
    210                 215                 220

Thr Gly Gly Phe Arg Leu Gly Lys Lys Ile Gly His Asp Ile Asp Phe
225                 230                 235                 240

Leu Ile Thr Asn Pro Gly Pro Arg Glu Asp Glu Glu Leu Leu His Lys
                245                 250                 255

Val Ile Asp Leu Trp Lys Lys Gln Gly Leu Leu Leu Tyr Cys Asp Ile
            260                 265                 270

Ile Glu Ser Thr Phe Val Lys Glu Gln Leu Pro Ser Arg Lys Val Asp
        275                 280                 285

Ala Met Asp His Phe Gln Lys Cys Phe Ala Ile Leu Lys Leu Tyr Gln
    290                 295                 300

Pro Arg Val Asp Asn Ser Thr Ser Asn Thr Ser Lys Lys Leu Glu Met
305                 310                 315                 320

Ala Glu Val Lys Asp Trp Lys Ala Ile Arg Val Asp Leu Val Ile Thr
                325                 330                 335

Pro Phe Glu Gln Tyr Ala Tyr Ala Leu Leu Gly Trp Thr Gly Ser Ala
            340                 345                 350

Phe Phe Asn Arg Asp Leu Arg Arg Tyr Ala Ser His Glu Arg Lys Met
        355                 360                 365

Ile Leu Asp Asn His Ala Leu Tyr Asp Arg Arg Lys Arg Ile Phe Leu
    370                 375                 380

Lys Ala Gly Ser Glu Glu Glu Ile Phe Ala His Leu Gly Leu Asp Tyr
385                 390                 395                 400

Val Glu Pro Trp Glu Arg Asn Ala
                405
```

```
<210> SEQ ID NO 5
<211> LENGTH: 370
<212> TYPE: PRT
<213> ORGANISM: ARTIFICIAL SEQUENCE
<220> FEATURE:
<223> OTHER INFORMATION: B19 trunc wt (Neopelma chrysocephalum)(saffron-
      crested neopelma)

<400> SEQUENCE: 5

Phe Ile Ala Arg Lys Val Ser Gln Tyr Ser Cys Gln Arg Lys Thr Thr
1               5                   10                  15

Leu Asn Asn Tyr Asn Lys Lys Phe Thr Asp Ala Phe Glu Ile Met Ala
            20                  25                  30

Glu Asn Tyr Glu Phe Lys Glu Asn Glu Ile Phe Cys Leu Glu Phe Leu
        35                  40                  45

Arg Ala Ala Ser Leu Leu Lys Tyr Leu Pro Phe Pro Val Thr Arg Met
    50                  55                  60

Lys Asp Ile Gln Gly Leu Pro Cys Ile Gly Asp Gln Val Arg Asp Val
65                  70                  75                  80

Ile Glu Gly Ile Ile Glu Glu Gly Glu Ser Ser Arg Val Lys Glu Val
                85                  90                  95

Leu Asn Asp Glu Arg Tyr Lys Ala Phe Lys Gln Phe Thr Ser Val Phe
            100                 105                 110

Gly Val Gly Val Lys Thr Ser Glu Lys Trp Tyr Arg Met Gly Leu Arg
        115                 120                 125

Thr Val Glu Glu Leu Lys Ala Asp Lys Thr Leu Lys Leu Ser Lys Met
    130                 135                 140

Gln Lys Ala Gly Phe Leu Tyr Tyr Glu Asp Leu Val Ser Cys Val Ser
145                 150                 155                 160
```

Lys Ala Glu Ala Asp Ala Val Thr Leu Ile Val Lys Asn Thr Val Ser
165 170 175

Thr Phe Leu Pro Asp Ala Leu Val Thr Ile Thr Gly Gly Phe Arg Arg
180 185 190

Gly Lys Lys Met Gly His Asp Ile Asp Phe Leu Ile Thr Asn Pro Gly
195 200 205

Pro Arg Glu Asp Asp Glu Leu Leu His Lys Val Val Asp Leu Trp Lys
210 215 220

Lys Gln Gly Leu Leu Leu Tyr Cys Asp Ile Ile Glu Ser Thr Phe Val
225 230 235 240

Glu Glu Gln Leu Pro Ser Arg Lys Val Asp Ala Met Asp Asn Phe Gln
245 250 255

Lys Cys Phe Thr Ile Leu Lys Leu Tyr Gln Pro Gly Val Asp Asn Ser
260 265 270

Ser Tyr Asn Met Ser Lys Lys Ser Asp Met Ala Glu Val Lys Asp Trp
275 280 285

Lys Ala Ile Arg Val Asp Leu Val Ile Thr Pro Phe Glu Gln Tyr Ala
290 295 300

Tyr Ala Leu Leu Gly Trp Thr Gly Ser Arg Glu Phe Gly Arg Asp Leu
305 310 315 320

Arg Arg Tyr Ala Ser His Glu Arg Lys Met Ile Leu Asp Asn His Gly
325 330 335

Leu Tyr Asp Arg Arg Lys Arg Ile Phe Leu Lys Ala Gly Ser Glu Glu
340 345 350

Glu Ile Phe Ala His Leu Gly Leu Asp Tyr Val Glu Pro Trp Glu Arg
355 360 365

Asn Ala
370

<210> SEQ ID NO 6
<211> LENGTH: 370
<212> TYPE: PRT
<213> ORGANISM: ARTIFICIAL SEQUENCE
<220> FEATURE:
<223> OTHER INFORMATION: B19 trunc new

<400> SEQUENCE: 6

Ser Ser Val Ser Lys Val Ser Gln Tyr Ser Cys Gln Arg Lys Thr Thr
1 5 10 15

Leu Asn Asn Tyr Asn Lys Lys Phe Thr Asp Ala Phe Glu Ile Met Ala
20 25 30

Glu Asn Tyr Glu Phe Lys Glu Asn Glu Ile Phe Cys Leu Glu Phe Arg
35 40 45

Arg Ala Ala Ser Val Leu Lys Phe Leu Pro Phe Pro Val Thr Arg Met
50 55 60

Lys Asp Ile Gln Gly Leu Pro Cys Met Gly Asp Arg Val Arg Asp Val
65 70 75 80

Ile Glu Glu Ile Ile Glu Glu Gly Glu Ser Ser Arg Val Lys Glu Val
85 90 95

Leu Asn Asp Glu Arg Tyr Lys Ala Phe Lys Gln Phe Thr Ser Val Phe
100 105 110

Gly Val Gly Arg Lys Thr Ser Glu Lys Trp Tyr Arg Met Gly Leu Arg
115 120 125

Thr Leu Glu Glu Val Lys Ala Asp Lys Thr Leu Lys Leu Ser Lys Met
130 135 140

Gln Lys Ala Gly Phe Leu Tyr Tyr Glu Asp Leu Ala Glu Arg Val Ser
145 150 155 160

Lys Ala Glu Ala Asp Ala Val Ser Leu Ile Val Lys Asn Thr Val Val
165 170 175

Thr Phe Leu Pro Asp Ala Leu Val Thr Ile Thr Gly Gly Phe Arg Leu
180 185 190

Gly Lys Lys Ile Gly His Asp Ile Asp Phe Leu Ile Thr Asn Pro Gly
195 200 205

Pro Arg Glu Asp Glu Glu Leu Leu His Lys Val Val Asp Leu Trp Lys
210 215 220

Lys Gln Gly Leu Leu Leu Tyr Cys Asp Ile Ile Glu Ser Thr Phe Val
225 230 235 240

Lys Glu Gln Leu Pro Ser Arg Lys Val Asp Ala Met Asp Asn Phe Gln
245 250 255

Lys Cys Phe Ala Ile Leu Lys Leu Tyr Gln Pro Arg Val Asp Asn Ser
260 265 270

Ser Tyr Asn Thr Ser Lys Lys Phe Asp Met Ala Glu Val Lys Asp Trp
275 280 285

Lys Ala Ile Arg Val Asp Leu Val Ile Thr Pro Phe Glu Gln Tyr Ala
290 295 300

Tyr Ala Leu Leu Gly Trp Thr Gly Ser Pro Gln Phe Asn Arg Asp Leu
305 310 315 320

Arg Arg Tyr Ala Thr His Glu Arg Lys Met Ile Leu Asp Asn His Ala
325 330 335

Leu Tyr Asp Arg Arg Lys Arg Ile Phe Leu Lys Ala Gly Ser Glu Glu
340 345 350

Glu Ile Phe Ala His Leu Gly Leu Asp Tyr Val Glu Pro Arg Glu Arg
355 360 365

Asn Ala
370

<210> SEQ ID NO 7
<211> LENGTH: 395
<212> TYPE: PRT
<213> ORGANISM: ARTIFICIAL SEQUENCE
<220> FEATURE:
<223> OTHER INFORMATION: B19

<400> SEQUENCE: 7

Met Ala Ser Ser His His His His His His Ser Ser Gly Ser Glu Asn
1 5 10 15

Leu Tyr Phe Gln Thr Gly Ser Ser Gly Ser Ser Val Ser Lys Val Ser
20 25 30

Gln Tyr Ser Cys Gln Arg Lys Thr Thr Leu Asn Asn Tyr Asn Lys Lys
35 40 45

Phe Thr Asp Ala Phe Glu Ile Met Ala Glu Asn Tyr Glu Phe Lys Glu
50 55 60

Asn Glu Ile Phe Cys Leu Glu Phe Arg Arg Ala Ala Ser Val Leu Lys
65 70 75 80

Phe Leu Pro Phe Pro Val Thr Arg Met Lys Asp Ile Gln Gly Leu Pro
85 90 95

Cys Met Gly Asp Arg Val Arg Asp Val Ile Glu Glu Ile Ile Glu Glu
100 105 110

Gly Glu Ser Ser Arg Val Lys Glu Val Leu Asn Asp Glu Arg Tyr Lys
115 120 125

```
Ala Phe Lys Gln Phe Thr Ser Val Phe Gly Val Gly Arg Lys Thr Ser
    130                 135                 140

Glu Lys Trp Tyr Arg Met Gly Leu Arg Thr Leu Glu Glu Val Lys Ala
145                 150                 155                 160

Asp Lys Thr Leu Lys Leu Ser Lys Met Gln Lys Ala Gly Phe Leu Tyr
                165                 170                 175

Tyr Glu Asp Leu Ala Glu Arg Val Ser Lys Ala Glu Ala Asp Ala Val
            180                 185                 190

Ser Leu Ile Val Lys Asn Thr Val Val Thr Phe Leu Pro Asp Ala Leu
        195                 200                 205

Val Thr Ile Thr Gly Gly Phe Arg Leu Gly Lys Lys Ile Gly His Asp
    210                 215                 220

Ile Asp Phe Leu Ile Thr Asn Pro Gly Pro Arg Glu Asp Glu Glu Leu
225                 230                 235                 240

Leu His Lys Val Val Asp Leu Trp Lys Lys Gln Gly Leu Leu Leu Tyr
                245                 250                 255

Cys Asp Ile Ile Glu Ser Thr Phe Val Lys Glu Gln Leu Pro Ser Arg
            260                 265                 270

Lys Val Asp Ala Met Asp Asn Phe Gln Lys Cys Phe Ala Ile Leu Lys
        275                 280                 285

Leu Tyr Gln Pro Arg Val Asp Asn Ser Ser Tyr Asn Thr Ser Lys Lys
    290                 295                 300

Phe Asp Met Ala Glu Val Lys Asp Trp Lys Ala Ile Arg Val Asp Leu
305                 310                 315                 320

Val Ile Thr Pro Phe Glu Gln Tyr Ala Tyr Ala Leu Leu Gly Trp Thr
                325                 330                 335

Gly Ser Pro Gln Phe Asn Arg Asp Leu Arg Arg Tyr Ala Thr His Glu
            340                 345                 350

Arg Lys Met Ile Leu Asp Asn His Ala Leu Tyr Asp Arg Arg Lys Arg
        355                 360                 365

Ile Phe Leu Lys Ala Gly Ser Glu Glu Glu Ile Phe Ala His Leu Gly
    370                 375                 380

Leu Asp Tyr Val Glu Pro Arg Glu Arg Asn Ala
385                 390                 395


<210> SEQ ID NO 8
<211> LENGTH: 383
<212> TYPE: PRT
<213> ORGANISM: ARTIFICIAL SEQUENCE
<220> FEATURE:
<223> OTHER INFORMATION: B57 trunc wt (Alligator sinensis)

<400> SEQUENCE: 8

Ser Pro Ser Pro Val Pro Gly Ser Gln Asn Val Pro Ala Pro Ser Val
1               5                   10                  15

Asp Lys Val Ser Gln Tyr Ala Cys Gln Arg Arg Thr Thr Leu Asn Asn
            20                  25                  30

Tyr Asn Lys Lys Phe Thr Asp Ala Phe Glu Ile Leu Ala Glu Asn Cys
        35                  40                  45

Glu Phe Arg Glu Asn Arg Leu Gly Cys Leu Glu Phe Leu Arg Ala Ala
    50                  55                  60

Ser Val Leu Lys Phe Leu Pro Phe Pro Ile Val Lys Met Lys Asn Ile
65                  70                  75                  80

Glu Gly Leu Pro Cys Met Gly Asp Lys Val Lys Cys Val Ile Glu Glu
                85                  90                  95
```

-continued

```
Ile Leu Glu Glu Gly Glu Ser Cys Gln Ala Lys Glu Ile Leu Asn Asp
            100                 105                 110

Glu Arg Tyr Lys Ser Phe Lys Leu Phe Thr Ser Val Phe Gly Val Gly
        115                 120                 125

Leu Lys Thr Thr Glu Lys Trp Tyr Arg Met Gly Phe Arg Thr Leu Glu
    130                 135                 140

Glu Val Lys Ala Glu Lys Thr Leu Lys Leu Ser Arg Met Gln Ile Ala
145                 150                 155                 160

Gly Phe Leu His Tyr Glu Asp Ile Ile Ser Tyr Val Ser Lys Ala Glu
                165                 170                 175

Ala Asp Ala Val Ser Leu Leu Ile Lys Asp Thr Val Cys Met Phe Leu
            180                 185                 190

Pro Asp Ala Leu Val Thr Ile Thr Gly Gly Phe Arg Arg Gly Lys Lys
        195                 200                 205

Thr Gly His Asp Val Asp Phe Leu Ile Thr Asn Pro Gly Pro Glu Glu
    210                 215                 220

Glu Lys Glu Leu Leu His Lys Val Val Asp Leu Trp Glu Lys Gln Gly
225                 230                 235                 240

Leu Leu Leu Tyr Tyr Asp Val Ile Glu Ser Thr Phe Glu Lys Glu Lys
                245                 250                 255

Arg Pro Ser Arg Lys Val Asp Ala Leu Asp His Phe Gln Lys Cys Phe
            260                 265                 270

Ala Ile Leu Lys Leu His Gln Gln Arg Arg Gly Asn Ser Asn Ser Asn
        275                 280                 285

Ile Ser Lys Glu Ser Asp Lys Ala Glu Val Lys Asp Trp Lys Ala Ile
    290                 295                 300

Arg Val Asp Leu Val Ile Ser Pro Phe Glu Gln Tyr Ala Tyr Ala Leu
305                 310                 315                 320

Leu Gly Trp Thr Gly Ser Arg Gln Phe Glu Arg Asp Leu Arg Arg Tyr
                325                 330                 335

Ala Ser Arg Glu Arg Lys Met Met Leu Asp Asn His Ala Leu Tyr Asp
            340                 345                 350

Lys Thr Lys Arg Thr Phe Leu Lys Ala Glu Ser Glu Glu Ile Phe
        355                 360                 365

Ala His Leu Gly Leu Asp Tyr Ile Glu Pro Trp Glu Arg Asn Ala
    370                 375                 380
```

<210> SEQ ID NO 9
<211> LENGTH: 383
<212> TYPE: PRT
<213> ORGANISM: ARTIFICIAL SEQUENCE
<220> FEATURE:
<223> OTHER INFORMATION: B57 trunc new

<400> SEQUENCE: 9

```
Ser Pro Ser Pro Val Pro Gly Ser Gln Asn Val Pro Ala Pro Ser Val
1               5                   10                  15

Asp Lys Ile Ser Gln Tyr Ala Cys Gln Arg Arg Thr Thr Leu Asn Asn
            20                  25                  30

Tyr Asn Lys Lys Phe Thr Asp Ala Phe Glu Ile Leu Ala Glu Asn Tyr
        35                  40                  45

Glu Phe Asn Glu Asn Lys Gly Phe Cys Leu Ala Phe Arg Arg Ala Ala
    50                  55                  60

Ser Val Leu Lys Phe Leu Pro Phe Thr Ile Val Arg Met Asn Asp Ile
65                  70                  75                  80
```

Gln Gly Leu Pro Trp Met Gly Asp Gln Val Lys Arg Val Ile Glu Glu
85 90 95

Ile Leu Glu Glu Gly Glu Ser Ser Lys Val Lys Glu Val Leu Asn Asp
100 105 110

Glu Lys Tyr Lys Ala Phe Lys Leu Phe Thr Ser Val Phe Gly Val Gly
115 120 125

Arg Lys Thr Ser Glu Lys Trp Tyr Arg Met Gly Leu Arg Thr Leu Glu
130 135 140

Glu Val Lys Ala Asp Lys Thr Leu Lys Leu Thr Lys Met Gln Lys Ala
145 150 155 160

Gly Phe Leu Tyr Tyr Glu Asp Leu Ile Ser Arg Val Ser Lys Ala Glu
165 170 175

Ala Asp Ala Val Ser Leu Ile Val Lys Asp Thr Val Trp Lys Phe Leu
180 185 190

Pro Asp Ala Leu Val Thr Leu Thr Gly Gly Phe Arg Leu Gly Lys Lys
195 200 205

Met Gly His Asp Val Asp Phe Leu Ile Thr Thr Pro Gly Pro Glu Glu
210 215 220

Glu Glu Glu Leu Leu His Lys Val Ile Asp Leu Trp Lys Lys Gln Gly
225 230 235 240

Leu Leu Leu Tyr Tyr Asp Ile Ile Glu Ser Thr Phe Glu Lys Thr Lys
245 250 255

Leu Pro Ser Arg Thr Val Asp Ala Leu Asp His Phe Gln Lys Cys Phe
260 265 270

Ala Ile Leu Lys Leu His Lys Gln Arg Val Asp Asn Gly Asn Ser Asn
275 280 285

Gln Ser Lys Glu Phe Asp Lys Glu Glu Thr Lys Asp Trp Lys Ala Ile
290 295 300

Arg Val Asp Leu Val Ile Thr Pro Phe Glu Gln Tyr Ala Tyr Ala Leu
305 310 315 320

Leu Gly Trp Thr Gly Ser Ala Phe Phe Asn Arg Asp Leu Arg Arg Tyr
325 330 335

Ala Thr His Glu Lys Lys Met Met Leu Asp Asn His Ala Leu Tyr Asp
340 345 350

Lys Thr Lys Arg Ile Phe Leu Lys Ala Ala Ser Glu Glu Glu Ile Phe
355 360 365

Ala His Leu Gly Leu Asp Tyr Leu Glu Pro Trp Glu Arg Asn Ala
370 375 380

<210> SEQ ID NO 10
<211> LENGTH: 408
<212> TYPE: PRT
<213> ORGANISM: ARTIFICIAL SEQUENCE
<220> FEATURE:
<223> OTHER INFORMATION: B57

<400> SEQUENCE: 10

Met Ala Ser Ser His His His His His His Ser Ser Gly Ser Glu Asn
1 5 10 15

Leu Tyr Phe Gln Thr Gly Ser Ser Gly Ser Pro Ser Pro Val Pro Gly
20 25 30

Ser Gln Asn Val Pro Ala Pro Ser Val Asp Lys Ile Ser Gln Tyr Ala
35 40 45

Cys Gln Arg Arg Thr Thr Leu Asn Asn Tyr Asn Lys Lys Phe Thr Asp
50 55 60

```
Ala Phe Glu Ile Leu Ala Glu Asn Tyr Glu Phe Asn Glu Asn Lys Gly
65                  70                  75                  80

Phe Cys Leu Ala Phe Arg Arg Ala Ala Ser Val Leu Lys Phe Leu Pro
                85                  90                  95

Phe Thr Ile Val Arg Met Asn Asp Ile Gln Gly Leu Pro Trp Met Gly
            100                 105                 110

Asp Gln Val Lys Arg Val Ile Glu Glu Ile Leu Glu Glu Gly Glu Ser
        115                 120                 125

Ser Lys Val Lys Glu Val Leu Asn Asp Glu Lys Tyr Lys Ala Phe Lys
    130                 135                 140

Leu Phe Thr Ser Val Phe Gly Val Gly Arg Lys Thr Ser Glu Lys Trp
145                 150                 155                 160

Tyr Arg Met Gly Leu Arg Thr Leu Glu Glu Val Lys Ala Asp Lys Thr
                165                 170                 175

Leu Lys Leu Thr Lys Met Gln Lys Ala Gly Phe Leu Tyr Tyr Glu Asp
            180                 185                 190

Leu Ile Ser Arg Val Ser Lys Ala Glu Ala Asp Ala Val Ser Leu Ile
        195                 200                 205

Val Lys Asp Thr Val Trp Lys Phe Leu Pro Asp Ala Leu Val Thr Leu
    210                 215                 220

Thr Gly Gly Phe Arg Leu Gly Lys Lys Met Gly His Asp Val Asp Phe
225                 230                 235                 240

Leu Ile Thr Thr Pro Gly Pro Glu Glu Glu Glu Glu Leu Leu His Lys
                245                 250                 255

Val Ile Asp Leu Trp Lys Lys Gln Gly Leu Leu Leu Tyr Tyr Asp Ile
            260                 265                 270

Ile Glu Ser Thr Phe Glu Lys Thr Lys Leu Pro Ser Arg Thr Val Asp
        275                 280                 285

Ala Leu Asp His Phe Gln Lys Cys Phe Ala Ile Leu Lys Leu His Lys
    290                 295                 300

Gln Arg Val Asp Asn Gly Asn Ser Asn Gln Ser Lys Glu Phe Asp Lys
305                 310                 315                 320

Glu Glu Thr Lys Asp Trp Lys Ala Ile Arg Val Asp Leu Val Ile Thr
                325                 330                 335

Pro Phe Glu Gln Tyr Ala Tyr Ala Leu Leu Gly Trp Thr Gly Ser Ala
            340                 345                 350

Phe Phe Asn Arg Asp Leu Arg Arg Tyr Ala Thr His Glu Lys Lys Met
        355                 360                 365

Met Leu Asp Asn His Ala Leu Tyr Asp Lys Thr Lys Arg Ile Phe Leu
    370                 375                 380

Lys Ala Ala Ser Glu Glu Glu Ile Phe Ala His Leu Gly Leu Asp Tyr
385                 390                 395                 400

Leu Glu Pro Trp Glu Arg Asn Ala
                405
```

<210> SEQ ID NO 11
<211> LENGTH: 380
<212> TYPE: PRT
<213> ORGANISM: ARTIFICIAL SEQUENCE
<220> FEATURE:
<223> OTHER INFORMATION: B59 trunc wt (Xenopus laevis)

<400> SEQUENCE: 11

```
Ser Pro Ser Pro Val Pro Gly Ser Gln Asn Val Pro Ala Pro Ser Glu
1               5                   10                  15
```

-continued

```
Val Lys Val Ser Gln Tyr Ala Cys Gln Arg Cys Thr Thr Leu Gln Asp
            20                  25                  30

Thr Asn Arg Ile Phe Thr Asp Ala Phe Asp Ile Leu Ala Glu His Phe
        35                  40                  45

Glu Phe Cys Glu Asn Lys Gly Arg Thr Val Ala Phe Leu Arg Ala Ser
    50                  55                  60

Ser Leu Ile Lys Ser Leu Pro Phe Pro Ile Thr Ala Met Lys Glu Leu
65                  70                  75                  80

Glu Gly Leu Pro Trp Leu Gly Asp Gln Met Lys Gly Ile Ile Glu Glu
                85                  90                  95

Ile Leu Glu Glu Gly Lys Ser Tyr Lys Val Leu Glu Val Met Asn Glu
            100                 105                 110

Glu Arg Tyr Lys Ser Phe Lys Gln Phe Thr Ser Val Phe Gly Val Gly
        115                 120                 125

Leu Lys Thr Ser Asp Lys Trp Phe Arg Met Gly Phe Arg Thr Leu Glu
    130                 135                 140

Glu Ile Lys Asn Glu Lys Glu Leu Lys Leu Thr Lys Met Gln Lys Cys
145                 150                 155                 160

Gly Leu Leu Tyr Tyr Glu Asp Ile Thr Ser Tyr Val Ser Arg Ala Glu
                165                 170                 175

Ala Glu Thr Thr Glu Gln Leu Ile Lys Ser Ile Val Trp Lys Phe Val
            180                 185                 190

Pro Asp Ala Ile Val Thr Leu Thr Gly Gly Phe Arg Arg Gly Lys Lys
        195                 200                 205

Lys Gly His Asp Val Asp Ile Leu Ile Thr Cys Ala Arg Lys Gly Lys
    210                 215                 220

Glu Lys Asn Ile Leu His Asn Thr Met Ser Val Leu Lys Asn Arg Gly
225                 230                 235                 240

Leu Leu Leu Phe Tyr Asn Ile Ile Glu Ser Thr Phe Asp Glu Thr Lys
                245                 250                 255

Leu Pro Ser Arg His Val Asp Ala Leu Asp His Phe Gln Lys Cys Phe
            260                 265                 270

Thr Ile Leu Lys Leu Pro Lys Arg Gln Met Asp Ile Gly Asn Ile Ile
        275                 280                 285

Asp Pro His Glu Cys Glu Arg Lys Asn Trp Lys Ala Val Arg Leu Asp
    290                 295                 300

Leu Val Ile Thr Pro Tyr Glu Gln Tyr Pro Tyr Ala Leu Leu Gly Trp
305                 310                 315                 320

Thr Gly Ser Arg Gln Phe Glu Arg Asp Leu Arg Arg Tyr Ala Thr His
                325                 330                 335

Glu Lys Arg Met Met Leu Asp Asn His Gly Leu Tyr Asp Lys Thr Lys
            340                 345                 350

Asn Asn Phe Leu Lys Ala Asn Asn Glu Glu Asp Ile Phe Lys Gln Leu
        355                 360                 365

Gly Leu Asp Tyr Leu Glu Pro Trp Glu Arg Asn Ala
    370                 375                 380
```

<210> SEQ ID NO 12
<211> LENGTH: 380
<212> TYPE: PRT
<213> ORGANISM: ARTIFICIAL SEQUENCE
<220> FEATURE:
<223> OTHER INFORMATION: B59 trunc new

<400> SEQUENCE: 12

```
Ser Pro Ser Pro Val Pro Gly Ser Gln Asn Val Pro Ala Pro Ser Glu
1               5                   10                  15

Val Lys Val Ser Gln Tyr Ala Cys Gln Arg Arg Thr Thr Leu Gln Asp
            20                  25                  30

Thr Asn Arg Ile Phe Thr Asp Ala Phe Asp Ile Leu Ala Glu Asn Tyr
        35                  40                  45

Glu Phe Asn Glu Asn Lys Gly Pro Cys Val Ala Phe Arg Arg Ala Ser
    50                  55                  60

Ser Val Leu Lys Ser Leu Pro Phe Pro Ile Val Ala Met Lys Asp Leu
65                  70                  75                  80

Glu Gly Leu Pro Trp Leu Gly Asp Gln Met Lys Arg Ile Ile Glu Glu
                85                  90                  95

Ile Leu Glu Glu Gly Lys Ser Ser Lys Val Val Glu Val Met Asn Asp
            100                 105                 110

Glu Arg Tyr Lys Ala Phe Lys Leu Phe Thr Ser Val Phe Gly Val Gly
        115                 120                 125

Arg Lys Thr Ser Glu Lys Trp Phe Arg Met Gly Phe Arg Thr Leu Glu
    130                 135                 140

Glu Ile Lys Ser Asp Lys Glu Leu Lys Leu Thr Lys Met Gln Lys Ala
145                 150                 155                 160

Gly Leu Leu Tyr Tyr Glu Asp Ile Thr Ser Ala Val Ser Lys Ala Glu
                165                 170                 175

Ala Glu Ala Val Glu Gln Leu Ile Lys Ser Ile Val Trp Lys Phe Val
            180                 185                 190

Pro Asp Ala Ile Val Thr Leu Thr Gly Gly Phe Arg Leu Gly Lys Lys
        195                 200                 205

Met Gly His Asp Val Asp Ile Leu Ile Thr Thr Pro Arg Lys Gly Glu
    210                 215                 220

Lys Glu Glu Ile Leu His Lys Thr Ile Asn Val Leu Lys Lys Arg Gly
225                 230                 235                 240

Leu Leu Leu Phe Tyr Asn Ile Ile Glu Ser Thr Phe Asp Glu Thr Lys
                245                 250                 255

Leu Pro Ser Arg His Val Asp Ala Leu Asp His Phe Gln Lys Cys Phe
            260                 265                 270

Thr Ile Leu Lys Leu Gln Lys Gln Gln Leu Asp Asn Gly Asn Ser Asn
        275                 280                 285

Glu Pro Phe Glu Thr Glu Lys Lys Asn Trp Lys Ala Ile Arg Val Asp
    290                 295                 300

Leu Val Ile Thr Pro Tyr Glu Gln Tyr Ala Tyr Ala Leu Leu Gly Trp
305                 310                 315                 320

Thr Gly Ser Pro Gln Phe Asn Arg Asp Leu Arg Arg Tyr Ala Thr His
                325                 330                 335

Glu Lys Arg Met Met Leu Asp Asn His Ala Leu Tyr Asp Lys Thr Lys
            340                 345                 350

Asn Ile Phe Leu Lys Ala Asn Ser Glu Glu Asp Ile Phe Thr His Leu
        355                 360                 365

Gly Leu Asp Tyr Leu Glu Pro Trp Glu Arg Asn Ala
    370                 375                 380
```

<210> SEQ ID NO 13
<211> LENGTH: 405
<212> TYPE: PRT
<213> ORGANISM: ARTIFICIAL SEQUENCE
<220> FEATURE:

<223> OTHER INFORMATION: B59

<400> SEQUENCE: 13

```
Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30

Ser Gln Asn Val Pro Ala Pro Ser Glu Val Lys Val Ser Gln Tyr Ala
        35                  40                  45

Cys Gln Arg Arg Thr Thr Leu Gln Asp Thr Asn Arg Ile Phe Thr Asp
    50                  55                  60

Ala Phe Asp Ile Leu Ala Glu Asn Tyr Glu Phe Asn Glu Asn Lys Gly
65                  70                  75                  80

Pro Cys Val Ala Phe Arg Arg Ala Ser Ser Val Leu Lys Ser Leu Pro
                85                  90                  95

Phe Pro Ile Val Ala Met Lys Asp Leu Glu Gly Leu Pro Trp Leu Gly
            100                 105                 110

Asp Gln Met Lys Arg Ile Ile Glu Glu Ile Leu Glu Glu Gly Lys Ser
        115                 120                 125

Ser Lys Val Val Glu Val Met Asn Asp Glu Arg Tyr Lys Ala Phe Lys
    130                 135                 140

Leu Phe Thr Ser Val Phe Gly Val Gly Arg Lys Thr Ser Glu Lys Trp
145                 150                 155                 160

Phe Arg Met Gly Phe Arg Thr Leu Glu Glu Ile Lys Ser Asp Lys Glu
                165                 170                 175

Leu Lys Leu Thr Lys Met Gln Lys Ala Gly Leu Leu Tyr Tyr Glu Asp
            180                 185                 190

Ile Thr Ser Ala Val Ser Lys Ala Glu Ala Glu Ala Val Glu Gln Leu
        195                 200                 205

Ile Lys Ser Ile Val Trp Lys Phe Val Pro Asp Ala Ile Val Thr Leu
    210                 215                 220

Thr Gly Gly Phe Arg Leu Gly Lys Lys Met Gly His Asp Val Asp Ile
225                 230                 235                 240

Leu Ile Thr Thr Pro Arg Lys Gly Glu Lys Glu Glu Ile Leu His Lys
                245                 250                 255

Thr Ile Asn Val Leu Lys Lys Arg Gly Leu Leu Leu Phe Tyr Asn Ile
            260                 265                 270

Ile Glu Ser Thr Phe Asp Glu Thr Lys Leu Pro Ser Arg His Val Asp
        275                 280                 285

Ala Leu Asp His Phe Gln Lys Cys Phe Thr Ile Leu Lys Leu Gln Lys
    290                 295                 300

Gln Gln Leu Asp Asn Gly Asn Ser Asn Glu Pro Phe Glu Thr Glu Lys
305                 310                 315                 320

Lys Asn Trp Lys Ala Ile Arg Val Asp Leu Val Ile Thr Pro Tyr Glu
                325                 330                 335

Gln Tyr Ala Tyr Ala Leu Leu Gly Trp Thr Gly Ser Pro Gln Phe Asn
            340                 345                 350

Arg Asp Leu Arg Arg Tyr Ala Thr His Glu Lys Arg Met Met Leu Asp
        355                 360                 365

Asn His Ala Leu Tyr Asp Lys Thr Lys Asn Ile Phe Leu Lys Ala Asn
    370                 375                 380

Ser Glu Glu Asp Ile Phe Thr His Leu Gly Leu Asp Tyr Leu Glu Pro
385                 390                 395                 400
```

-continued

```
Trp Glu Arg Asn Ala
                405


<210> SEQ ID NO 14
<211> LENGTH: 383
<212> TYPE: PRT
<213> ORGANISM: ARTIFICIAL SEQUENCE
<220> FEATURE:
<223> OTHER INFORMATION: B63 trunc wt (Notechis scutatus)

<400> SEQUENCE: 14

Ser Pro Ser Pro Val Pro Gly Ser Gln Asn Val Pro Ala Pro Ser Val
1               5                   10                  15

Asp Ser Ile Ser Pro Tyr Ala Cys Gln Arg Arg Thr Thr Leu Lys Asn
            20                  25                  30

Tyr Asn Gln Lys Phe Thr Asp Ala Phe Glu Ile Leu Val Glu Asn Tyr
        35                  40                  45

Glu Phe Asn Glu Asn Lys Glu Phe Cys Leu Ala Phe Gly Arg Ala Ala
    50                  55                  60

Ser Leu Leu Lys Cys Leu Pro Phe Thr Val Val Arg Val Asn Asp Ile
65                  70                  75                  80

Glu Gly Leu Pro Trp Met Gly Lys Gln Val Arg Glu Ile Ile Glu Asp
                85                  90                  95

Ile Leu Glu Glu Gly Glu Ser Ser Lys Val Lys Ala Val Leu Asn Asp
            100                 105                 110

Glu Asn Tyr Arg Ser Ile Lys Leu Phe Thr Ser Val Phe Gly Val Gly
        115                 120                 125

Leu Arg Thr Ser Glu Lys Trp Tyr Arg Met Gly Leu Arg Thr Leu Glu
    130                 135                 140

Glu Val Lys Cys Asn Lys Asn Leu Thr Leu Thr Arg Met Gln Lys Ala
145                 150                 155                 160

Gly Phe Phe Tyr Tyr Asp Asp Leu Ile Ser Ser Val Ser Lys Ala Glu
                165                 170                 175

Ala Asp Ala Ala Thr Gln Ile Val Gln Asp Thr Val Trp Lys Ile Leu
            180                 185                 190

Pro Asn Ala Val Val Thr Leu Thr Gly Gly Phe Arg Arg Gly Lys Gln
        195                 200                 205

Thr Gly His Asp Val Asp Phe Leu Ile Thr Val Pro Gly Ser Arg Gln
    210                 215                 220

Glu Glu Glu Leu Leu His Pro Val Ile Asp Ile Trp Lys Lys Gln Glu
225                 230                 235                 240

Leu Leu Leu Tyr Tyr Asp Leu Ile Glu Ser Thr Phe Glu Asn Thr Lys
                245                 250                 255

Leu Pro Ser Arg Lys Val Asp Ala Leu Asp His Phe Gln Lys Cys Phe
            260                 265                 270

Ala Ile Leu Lys Val His Lys Glu Arg Val Asn Lys Gly Ser Ala Val
        275                 280                 285

Gln Ser Asn Val Phe Ala Glu Glu Gly Thr Lys Asp Trp Lys Ala Ile
    290                 295                 300

Arg Val Asp Leu Val Val Thr Pro Phe Gln His Tyr Ala Phe Ala Leu
305                 310                 315                 320

Leu Gly Trp Thr Gly Ser Arg Gln Phe Glu Arg Asp Leu Arg Arg Tyr
                325                 330                 335

Ala Thr Gln Glu Lys Lys Met Met Leu Asp Asn His Ala Leu Tyr Asp
            340                 345                 350
```

-continued

Lys Thr Lys Lys Ile Phe Leu Ser Ala Ala Asn Glu Glu Glu Ile Phe
355 360 365

Ser His Leu Gly Leu Asp Tyr Leu Glu Pro Trp Glu Arg Asn Ala
370 375 380

<210> SEQ ID NO 15
<211> LENGTH: 384
<212> TYPE: PRT
<213> ORGANISM: ARTIFICIAL SEQUENCE
<220> FEATURE:
<223> OTHER INFORMATION: B63 trunc new

<400> SEQUENCE: 15

Ser Pro Ser Pro Val Pro Gly Ser Gln Asn Val Pro Ala Pro Ser Val
1 5 10 15

Asp Ser Ile Ser Gln Tyr Ala Cys Gln Arg Arg Thr Thr Leu Asn Asn
20 25 30

Tyr Asn Lys Lys Phe Thr Asp Ala Phe Glu Ile Leu Ala Glu Asn Tyr
35 40 45

Glu Phe Asn Glu Asn Lys Gly Phe Cys Leu Ala Phe Arg Arg Ala Ala
50 55 60

Ser Val Leu Lys Phe Leu Pro Phe Thr Ile Val Arg Val Asn Asp Ile
65 70 75 80

Glu Gly Leu Pro Trp Met Gly Glu Gln Val Lys Arg Ile Ile Glu Asp
85 90 95

Ile Leu Glu Glu Gly Glu Ser Ser Lys Val Lys Ala Val Leu Asn Asn
100 105 110

Glu Asn Tyr Arg Ala Phe Lys Leu Phe Thr Ser Val Phe Gly Val Gly
115 120 125

Arg Lys Thr Ser Glu Lys Trp Tyr Arg Met Gly Leu Arg Thr Leu Glu
130 135 140

Glu Val Lys Ala Asp Lys Asn Leu Lys Leu Thr Arg Met Gln Lys Ala
145 150 155 160

Gly Phe Leu His Tyr Glu Asp Leu Ile Ser Arg Val Ser Lys Ala Glu
165 170 175

Ala Asp Ala Ala Ser Leu Ile Val Lys Asp Thr Val Trp Lys Phe Leu
180 185 190

Pro Asn Ala Leu Val Thr Leu Thr Gly Gly Phe Arg Leu Gly Lys Lys
195 200 205

Met Gly His Asp Val Asp Phe Leu Ile Thr Val Pro Gly Ser Arg Gln
210 215 220

Glu Glu Glu Glu Leu Leu His Thr Val Ile Asp Leu Trp Lys Lys Gln
225 230 235 240

Gly Leu Leu Leu Tyr Tyr Asp Leu Ile Glu Ser Thr Phe Glu Lys Thr
245 250 255

Lys Leu Pro Ser Arg Thr Val Asp Ala Leu Asp His Phe Gln Lys Cys
260 265 270

Phe Ala Ile Leu Lys Leu His Lys Glu Arg Val Asp Lys Gly Asn Ser
275 280 285

Ile Gln Ser Lys Ala Phe Ala Glu Glu Glu Thr Lys Asp Trp Lys Ala
290 295 300

Ile Arg Val Asp Leu Val Val Thr Pro Phe Glu Gln Tyr Ala Phe Ala
305 310 315 320

Leu Leu Gly Trp Thr Gly Ser Pro Phe Phe Asn Arg Asp Leu Arg Arg
325 330 335

```
Tyr Ala Thr His Glu Lys Lys Met Met Leu Asp Asn His Ala Leu Tyr
            340                 345                 350

Asp Lys Thr Lys Lys Ile Phe Leu Lys Ala Ala Ser Glu Glu Glu Ile
        355                 360                 365

Phe Ala His Leu Gly Leu Asp Tyr Leu Glu Pro Trp Glu Arg Asn Ala
    370                 375                 380


<210> SEQ ID NO 16
<211> LENGTH: 409
<212> TYPE: PRT
<213> ORGANISM: ARTIFICIAL SEQUENCE
<220> FEATURE:
<223> OTHER INFORMATION: B63

<400> SEQUENCE: 16

Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30

Ser Gln Asn Val Pro Ala Pro Ser Val Asp Ser Ile Ser Gln Tyr Ala
        35                  40                  45

Cys Gln Arg Arg Thr Thr Leu Asn Asn Tyr Asn Lys Lys Phe Thr Asp
    50                  55                  60

Ala Phe Glu Ile Leu Ala Glu Asn Tyr Glu Phe Asn Glu Asn Lys Gly
65                  70                  75                  80

Phe Cys Leu Ala Phe Arg Arg Ala Ala Ser Val Leu Lys Phe Leu Pro
                85                  90                  95

Phe Thr Ile Val Arg Val Asn Asp Ile Glu Gly Leu Pro Trp Met Gly
            100                 105                 110

Glu Gln Val Lys Arg Ile Ile Glu Asp Ile Leu Glu Glu Gly Glu Ser
        115                 120                 125

Ser Lys Val Lys Ala Val Leu Asn Asn Glu Asn Tyr Arg Ala Phe Lys
    130                 135                 140

Leu Phe Thr Ser Val Phe Gly Val Gly Arg Lys Thr Ser Glu Lys Trp
145                 150                 155                 160

Tyr Arg Met Gly Leu Arg Thr Leu Glu Glu Val Lys Ala Asp Lys Asn
                165                 170                 175

Leu Lys Leu Thr Arg Met Gln Lys Ala Gly Phe Leu His Tyr Glu Asp
            180                 185                 190

Leu Ile Ser Arg Val Ser Lys Ala Glu Ala Asp Ala Ala Ser Leu Ile
        195                 200                 205

Val Lys Asp Thr Val Trp Lys Phe Leu Pro Asn Ala Leu Val Thr Leu
    210                 215                 220

Thr Gly Gly Phe Arg Leu Gly Lys Lys Met Gly His Asp Val Asp Phe
225                 230                 235                 240

Leu Ile Thr Val Pro Gly Ser Arg Gln Glu Glu Glu Glu Leu Leu His
                245                 250                 255

Thr Val Ile Asp Leu Trp Lys Lys Gln Gly Leu Leu Leu Tyr Tyr Asp
            260                 265                 270

Leu Ile Glu Ser Thr Phe Glu Lys Thr Lys Leu Pro Ser Arg Thr Val
        275                 280                 285

Asp Ala Leu Asp His Phe Gln Lys Cys Phe Ala Ile Leu Lys Leu His
    290                 295                 300

Lys Glu Arg Val Asp Lys Gly Asn Ser Ile Gln Ser Lys Ala Phe Ala
305                 310                 315                 320
```

```
Glu Glu Glu Thr Lys Asp Trp Lys Ala Ile Arg Val Asp Leu Val Val
                325                 330                 335

Thr Pro Phe Glu Gln Tyr Ala Phe Ala Leu Leu Gly Trp Thr Gly Ser
            340                 345                 350

Pro Phe Phe Asn Arg Asp Leu Arg Arg Tyr Ala Thr His Glu Lys Lys
        355                 360                 365

Met Met Leu Asp Asn His Ala Leu Tyr Asp Lys Thr Lys Lys Ile Phe
    370                 375                 380

Leu Lys Ala Ala Ser Glu Glu Glu Ile Phe Ala His Leu Gly Leu Asp
385                 390                 395                 400

Tyr Leu Glu Pro Trp Glu Arg Asn Ala
                405


<210> SEQ ID NO 17
<211> LENGTH: 367
<212> TYPE: PRT
<213> ORGANISM: ARTIFICIAL SEQUENCE
<220> FEATURE:
<223> OTHER INFORMATION: F15 trunc wt (Salmo truttal)

<400> SEQUENCE: 17

Thr Ala Ala Ala Asn Val Ser Gln Tyr Ala Cys Leu Arg Arg Thr Thr
1               5                   10                  15

Thr Glu Asn His Asn Lys Ile Phe Thr Asp Val Leu Glu Glu Leu Ala
            20                  25                  30

Glu Asn Ser Glu Phe Asn Glu Ser Lys Gly Pro Cys Leu Ala Phe Arg
        35                  40                  45

Arg Ala Ala Ser Val Leu Lys Ser Leu Pro Ser Ala Val His Cys Leu
    50                  55                  60

Gly Ala Ile Gln Gly Leu Pro Cys Leu Gly Glu His Thr Lys Ala Val
65                  70                  75                  80

Met Glu Glu Ile Leu Ile Phe Gly Arg Ser Phe Lys Val Glu Glu Val
                85                  90                  95

Gln Ser Asp Glu Arg Tyr Gln Ala Leu Lys Leu Phe Thr Ser Val Phe
            100                 105                 110

Gly Val Gly Pro Lys Thr Ala Glu Lys Trp Tyr Arg Arg Gly Leu Arg
        115                 120                 125

Ser Leu Lys Glu Ile Leu Ala Glu Pro Asn Ile Gln Leu Asn Arg Met
    130                 135                 140

Gln Arg Ala Gly Phe Leu Tyr Tyr Arg Asp Ile Ser Lys Ala Val Ser
145                 150                 155                 160

Lys Ala Glu Ala Lys Ala Leu Ser Ser Ile Ile Glu Glu Thr Ala His
                165                 170                 175

Trp Ile Ala Pro Asp Ser Ile Leu Ala Leu Thr Gly Gly Phe Arg Arg
            180                 185                 190

Gly Lys Glu Tyr Gly His Asp Val Asp Phe Leu Leu Thr Met Pro Glu
        195                 200                 205

Met Gly Lys Glu Glu Gly Leu Leu Leu Arg Val Ile Asp Arg Leu Arg
    210                 215                 220

Asp Gln Gly Ile Leu Leu Tyr Cys Glu His Gln Asp Ser Thr Phe Asp
225                 230                 235                 240

Met Ser Lys Leu Pro Ser His Arg Phe Glu Ala Met Asp His Phe Glu
                245                 250                 255

Lys Cys Phe Leu Ile Leu Arg Leu Glu Glu Gly Gln Val Glu Gly Asp
            260                 265                 270
```

-continued

```
Gly Gly Leu Gln Lys Asp Pro Gly Glu Ser Arg Gly Trp Arg Ala Val
        275                 280                 285

Arg Val Asp Leu Val Ala Pro Pro Val Asp Arg Tyr Ala Phe Val Leu
    290                 295                 300

Leu Gly Trp Thr Gly Ser Arg Gln Phe Glu Arg Asp Leu Arg Arg Phe
305                 310                 315                 320

Ala Ser Lys Glu Arg Gly Met Cys Leu Asp Asn His Ala Leu Tyr Asp
                325                 330                 335

Lys Thr Lys Lys Leu Phe Leu Pro Ala Thr Ser Glu Glu Asp Ile Phe
            340                 345                 350

Ala His Leu Gly Leu Glu Tyr Val Glu Pro Trp Gln Arg Asn Ala
        355                 360                 365


<210> SEQ ID NO 18
<211> LENGTH: 367
<212> TYPE: PRT
<213> ORGANISM: ARTIFICIAL SEQUENCE
<220> FEATURE:
<223> OTHER INFORMATION: F15 trunc new

<400> SEQUENCE: 18

Ser Ser Val Ala Thr Val Ser Gln Tyr Ala Cys Gln Arg Arg Thr Thr
1               5                   10                  15

Met Glu Asn His Asn Lys Ile Phe Thr Asp Ala Phe Glu Val Leu Ala
            20                  25                  30

Glu Asn Ser Glu Phe Asn Glu Ser Lys Glu Ser Arg Asp Ala Phe Arg
        35                  40                  45

Arg Ala Ala Ser Val Leu Lys Ser Leu Pro Ser Ala Val Arg Ser Leu
    50                  55                  60

Gly Asp Thr Glu Gly Leu Pro Cys Leu Gly Glu His Thr Lys Arg Val
65                  70                  75                  80

Ile Glu Glu Ile Leu Glu Tyr Gly Arg Ser Ser Lys Val Glu Asp Ile
                85                  90                  95

Leu Ser Asp Glu Arg Tyr Gln Thr Met Lys Leu Phe Thr Ser Val Phe
            100                 105                 110

Gly Val Gly Pro Lys Thr Ala Glu Lys Trp Tyr Arg Arg Gly Leu Arg
        115                 120                 125

Ser Leu Glu Glu Val Arg Ala Glu Pro Ser Ile His Leu Asn Arg Met
    130                 135                 140

Gln Arg Ala Gly Phe Leu Tyr Tyr Arg Asp Ile Ser Lys Arg Val Ser
145                 150                 155                 160

Lys Ala Glu Ala Lys Ala Leu Gly Asn Ile Ile Glu Glu Thr Val His
                165                 170                 175

Ala Ile Ala Pro Asp Ala Ile Val Thr Leu Thr Gly Gly Phe Arg Leu
            180                 185                 190

Gly Lys Glu Phe Gly His Asp Val Asp Phe Ile Leu Thr Thr Pro Glu
        195                 200                 205

Met Gly Lys Glu Glu Gly Leu Leu Pro Arg Val Ile Asp Arg Leu Arg
    210                 215                 220

Asn Gln Gly Ile Leu Leu Tyr Cys Asp Tyr Gln Glu Ser Thr Phe Asp
225                 230                 235                 240

Met Ser Lys Leu Pro Ser Arg Thr Phe Glu Ala Met Asp His Phe Gln
                245                 250                 255

Lys Cys Phe Leu Ile Ile Lys Leu Lys Glu Gly Leu Val Glu Gly Glu
            260                 265                 270
```

-continued

```
Gly Gly Leu Gln Ser Asp Pro Gly Asp Arg Arg Gly Trp Arg Ala Val
        275                 280                 285

Arg Val Asp Leu Val Ala Pro Pro Val Asp Arg Tyr Ala Phe Ala Leu
    290                 295                 300

Leu Gly Trp Thr Gly Ser Pro Gln Phe Asn Arg Asp Leu Arg Arg Phe
305                 310                 315                 320

Ala Arg Leu Glu Arg Arg Met Leu Leu Asp Asn His Ala Leu Tyr Asp
                325                 330                 335

Lys Thr Lys Lys Ile Phe Leu Pro Ala Lys Thr Glu Glu Asp Ile Phe
            340                 345                 350

Ala His Leu Gly Leu Glu Tyr Ile Glu Pro Trp Gln Arg Asn Ala
        355                 360                 365


<210> SEQ ID NO 19
<211> LENGTH: 392
<212> TYPE: PRT
<213> ORGANISM: ARTIFICIAL SEQUENCE
<220> FEATURE:
<223> OTHER INFORMATION: F15

<400> SEQUENCE: 19

Met Ala Ser Ser His His His His His His Ser Ser Gly Ser Glu Asn
1               5                   10                  15

Leu Tyr Phe Gln Thr Gly Ser Ser Gly Ser Ser Val Ala Thr Val Ser
            20                  25                  30

Gln Tyr Ala Cys Gln Arg Arg Thr Thr Met Glu Asn His Asn Lys Ile
        35                  40                  45

Phe Thr Asp Ala Phe Glu Val Leu Ala Glu Asn Ser Glu Phe Asn Glu
    50                  55                  60

Ser Lys Glu Ser Arg Asp Ala Phe Arg Arg Ala Ala Ser Val Leu Lys
65                  70                  75                  80

Ser Leu Pro Ser Ala Val Arg Ser Leu Gly Asp Thr Glu Gly Leu Pro
                85                  90                  95

Cys Leu Gly Glu His Thr Lys Arg Val Ile Glu Glu Ile Leu Glu Tyr
            100                 105                 110

Gly Arg Ser Ser Lys Val Glu Asp Ile Leu Ser Asp Glu Arg Tyr Gln
        115                 120                 125

Thr Met Lys Leu Phe Thr Ser Val Phe Gly Val Gly Pro Lys Thr Ala
    130                 135                 140

Glu Lys Trp Tyr Arg Arg Gly Leu Arg Ser Leu Glu Glu Val Arg Ala
145                 150                 155                 160

Glu Pro Ser Ile His Leu Asn Arg Met Gln Arg Ala Gly Phe Leu Tyr
                165                 170                 175

Tyr Arg Asp Ile Ser Lys Arg Val Ser Lys Ala Glu Ala Lys Ala Leu
            180                 185                 190

Gly Asn Ile Ile Glu Glu Thr Val His Ala Ile Ala Pro Asp Ala Ile
        195                 200                 205

Val Thr Leu Thr Gly Gly Phe Arg Leu Gly Lys Glu Phe Gly His Asp
    210                 215                 220

Val Asp Phe Ile Leu Thr Thr Pro Glu Met Gly Lys Glu Glu Gly Leu
225                 230                 235                 240

Leu Pro Arg Val Ile Asp Arg Leu Arg Asn Gln Gly Ile Leu Leu Tyr
                245                 250                 255

Cys Asp Tyr Gln Glu Ser Thr Phe Asp Met Ser Lys Leu Pro Ser Arg
            260                 265                 270
```

-continued

```
Thr Phe Glu Ala Met Asp His Phe Gln Lys Cys Phe Leu Ile Ile Lys
        275                 280                 285

Leu Lys Glu Gly Leu Val Glu Gly Glu Gly Gly Leu Gln Ser Asp Pro
    290                 295                 300

Gly Asp Arg Arg Gly Trp Arg Ala Val Arg Val Asp Leu Val Ala Pro
305                 310                 315                 320

Pro Val Asp Arg Tyr Ala Phe Ala Leu Leu Gly Trp Thr Gly Ser Pro
                325                 330                 335

Gln Phe Asn Arg Asp Leu Arg Arg Phe Ala Arg Leu Glu Arg Arg Met
            340                 345                 350

Leu Leu Asp Asn His Ala Leu Tyr Asp Lys Thr Lys Lys Ile Phe Leu
        355                 360                 365

Pro Ala Lys Thr Glu Glu Asp Ile Phe Ala His Leu Gly Leu Glu Tyr
    370                 375                 380

Ile Glu Pro Trp Gln Arg Asn Ala
385                 390


<210> SEQ ID NO 20
<211> LENGTH: 377
<212> TYPE: PRT
<213> ORGANISM: ARTIFICIAL SEQUENCE
<220> FEATURE:
<223> OTHER INFORMATION: F24 trunc wt (Electrophorus electricus)

<400> SEQUENCE: 20

Ser Pro Ser Pro Val Pro Gly Ser Gln Asn Val Pro Ala Pro Ser Leu
1               5                   10                  15

Pro Thr Val Ser Gln Tyr Ala Cys Gln Arg Arg Thr Thr Leu Asp Asn
            20                  25                  30

His Asn Lys Val Phe Thr Asp Ala Leu Glu Val Leu Ile Glu Asn Tyr
        35                  40                  45

Glu Phe Ser Asp Asn Lys Gly Ala Cys Val Gly Phe Arg Arg Ala Ala
    50                  55                  60

Ser Val Leu Lys Ser Leu Pro Lys Pro Leu Arg Cys Leu Lys Asp Met
65                  70                  75                  80

Glu Gly Leu Pro Cys Leu Gly Asp Asp Thr Lys Ala Ile Ile Glu Glu
                85                  90                  95

Ile Tyr Glu Cys Gly Ser Ser Ser Arg Val Glu Asn Ile Leu Ser Asp
            100                 105                 110

Glu Lys Tyr Gln Thr Leu Lys Leu Phe Thr Ser Val Phe Gly Val Gly
        115                 120                 125

Pro Lys Thr Gly Glu Lys Trp Tyr Arg Arg Gly Leu Arg Ala Leu Glu
    130                 135                 140

Gln Val His Ser Glu Pro Ser Ile Gln Leu Asn Lys Met Gln Ala Ala
145                 150                 155                 160

Gly Phe Leu Tyr Tyr Glu Asp Ile Ser Lys Pro Val Ser Arg Ala Glu
                165                 170                 175

Ala Lys Ala Val Gly Cys Ile Ile Glu Glu Val Ala Ser Cys Phe Ser
            180                 185                 190

Ser Ser Val Thr Ile Thr Leu Thr Gly Gly Phe Arg Arg Gly Lys Glu
        195                 200                 205

Phe Gly His Asp Val Asp Phe Leu Leu Ser Ile Pro Glu Pro Gly Lys
    210                 215                 220

Glu Asp Gly Leu Leu Pro Ala Val Ile Asp Arg Leu Arg Lys Gln Gly
225                 230                 235                 240
```

```
Ile Leu Leu Tyr Ser Asp Leu Gln Glu Ser Thr Leu Gln Gln Trp Lys
                245                 250                 255

Arg Pro Ser Arg Cys Phe Asp Ser Met Asp His Phe Gln Lys Cys Phe
            260                 265                 270

Leu Ile Val Lys Leu Trp Thr Arg Leu Val Glu Gly His Arg Glu Asp
        275                 280                 285

Pro Ser Ser Gln Arg Asp Trp Lys Ala Val Arg Val Asp Leu Val Val
    290                 295                 300

Pro Pro Val Asp Cys Tyr Ala Phe Ala Leu Leu Gly Trp Ser Gly Ser
305                 310                 315                 320

Thr Gln Phe Glu Arg Asp Leu Arg Arg Phe Ala Arg Leu Glu Arg Arg
                325                 330                 335

Met Leu Leu Asp Asn His Ala Leu Tyr Asp Lys Thr Thr Asn Thr Phe
            340                 345                 350

Leu Gln Ala Lys Thr Glu Glu Asp Ile Phe Ala His Leu Gly Leu Asp
        355                 360                 365

Tyr Ile Glu Pro Trp Gln Arg Asn Ala
    370                 375


<210> SEQ ID NO 21
<211> LENGTH: 377
<212> TYPE: PRT
<213> ORGANISM: ARTIFICIAL SEQUENCE
<220> FEATURE:
<223> OTHER INFORMATION: F24 trunc new

<400> SEQUENCE: 21

Ser Pro Ser Pro Val Pro Gly Ser Gln Asn Val Pro Ala Pro Ser Leu
1               5                   10                  15

Pro Thr Val Ser Gln Tyr Ala Cys Gln Arg Arg Thr Thr Leu Asp Asn
            20                  25                  30

His Asn Lys Ile Phe Thr Asp Ala Leu Glu Val Leu Ala Glu Asn Tyr
        35                  40                  45

Glu Phe Ser Asp Ser Lys Glu Ser Arg Asp Ala Phe Arg Arg Ala Ala
    50                  55                  60

Ser Val Leu Lys Ser Leu Pro Thr Pro Leu Arg Ser Leu Gln Asp Thr
65                  70                  75                  80

Glu Gly Leu Pro Cys Leu Gly Glu Glu Thr Lys Arg Val Ile Glu Glu
                85                  90                  95

Ile Phe Glu Glu Gly Ser Ser Ser Arg Val Glu Asp Ile Leu Ser Asp
            100                 105                 110

Glu Arg Tyr Gln Thr Leu Lys Leu Phe Thr Ser Val Phe Gly Val Gly
        115                 120                 125

Pro Lys Thr Ala Glu Lys Trp Tyr Arg Arg Gly Leu Arg Ser Leu Glu
    130                 135                 140

Gln Val Arg Ser Asp Pro Ser Ile His Leu Asn Arg Met Gln Thr Ala
145                 150                 155                 160

Gly Phe Leu Tyr Tyr Glu Asp Ile Ser Lys Pro Val Ser Lys Ala Glu
                165                 170                 175

Ala Lys Ala Leu Gly Asn Ile Ile Glu Glu Thr Ala Ser Ala Phe Ser
            180                 185                 190

Pro Ser Val Thr Ile Thr Leu Thr Gly Gly Phe Arg Leu Gly Lys Glu
        195                 200                 205

Phe Gly His Asp Val Asp Phe Leu Leu Thr Val Pro Glu Pro Gly Lys
    210                 215                 220
```

-continued

```
Glu Asp Gly Leu Leu Pro Ala Val Ile Asp Arg Leu Arg Ser Gln Gly
225                 230                 235                 240

Ile Leu Leu Tyr Ser Asp Phe Gln Glu Ser Thr Phe Asp Leu Ser Lys
                245                 250                 255

Leu Pro Ser Arg Arg Phe Glu Ala Met Asp His Phe Gln Lys Cys Phe
            260                 265                 270

Leu Ile Val Lys Leu Lys Ala Gly Leu Val Glu Gly Glu Gly Ala Asp
        275                 280                 285

Pro Gly Asp Arg Arg Asp Trp Arg Ala Val Arg Val Asp Leu Val Ala
    290                 295                 300

Pro Pro Val Asp Arg Tyr Ala Phe Ala Leu Leu Gly Trp Ser Gly Ser
305                 310                 315                 320

Ala Phe Phe Asn Arg Asp Leu Arg Arg Phe Ala Arg Leu Glu Arg Gly
                325                 330                 335

Met Leu Leu Asp Asn His Ala Leu Tyr Asp Lys Thr Thr Asn Thr Phe
            340                 345                 350

Leu Gln Ala Lys Thr Glu Glu Asp Ile Phe Ala His Leu Gly Leu Asp
        355                 360                 365

Tyr Ile Glu Pro Trp Gln Arg Asn Ala
    370                 375


<210> SEQ ID NO 22
<211> LENGTH: 402
<212> TYPE: PRT
<213> ORGANISM: ARTIFICIAL SEQUENCE
<220> FEATURE:
<223> OTHER INFORMATION: F24

<400> SEQUENCE: 22

Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30

Ser Gln Asn Val Pro Ala Pro Ser Leu Pro Thr Val Ser Gln Tyr Ala
        35                  40                  45

Cys Gln Arg Arg Thr Thr Leu Asp Asn His Asn Lys Ile Phe Thr Asp
    50                  55                  60

Ala Leu Glu Val Leu Ala Glu Asn Tyr Glu Phe Ser Asp Ser Lys Glu
65                  70                  75                  80

Ser Arg Asp Ala Phe Arg Arg Ala Ala Ser Val Leu Lys Ser Leu Pro
                85                  90                  95

Thr Pro Leu Arg Ser Leu Gln Asp Thr Glu Gly Leu Pro Cys Leu Gly
            100                 105                 110

Glu Glu Thr Lys Arg Val Ile Glu Glu Ile Phe Glu Glu Gly Ser Ser
        115                 120                 125

Ser Arg Val Glu Asp Ile Leu Ser Asp Glu Arg Tyr Gln Thr Leu Lys
    130                 135                 140

Leu Phe Thr Ser Val Phe Gly Val Gly Pro Lys Thr Ala Glu Lys Trp
145                 150                 155                 160

Tyr Arg Arg Gly Leu Arg Ser Leu Glu Gln Val Arg Ser Asp Pro Ser
                165                 170                 175

Ile His Leu Asn Arg Met Gln Thr Ala Gly Phe Leu Tyr Tyr Glu Asp
            180                 185                 190

Ile Ser Lys Pro Val Ser Lys Ala Glu Ala Lys Ala Leu Gly Asn Ile
        195                 200                 205
```

Ile Glu Glu Thr Ala Ser Ala Phe Ser Pro Ser Val Thr Ile Thr Leu
    210                 215                 220

Thr Gly Gly Phe Arg Leu Gly Lys Glu Phe Gly His Asp Val Asp Phe
225                 230                 235                 240

Leu Leu Thr Val Pro Glu Pro Gly Lys Glu Asp Gly Leu Leu Pro Ala
                245                 250                 255

Val Ile Asp Arg Leu Arg Ser Gln Gly Ile Leu Leu Tyr Ser Asp Phe
            260                 265                 270

Gln Glu Ser Thr Phe Asp Leu Ser Lys Leu Pro Ser Arg Arg Phe Glu
        275                 280                 285

Ala Met Asp His Phe Gln Lys Cys Phe Leu Ile Val Lys Leu Lys Ala
    290                 295                 300

Gly Leu Val Glu Gly Glu Gly Ala Asp Pro Gly Asp Arg Arg Asp Trp
305                 310                 315                 320

Arg Ala Val Arg Val Asp Leu Val Ala Pro Pro Val Asp Arg Tyr Ala
                325                 330                 335

Phe Ala Leu Leu Gly Trp Ser Gly Ser Ala Phe Phe Asn Arg Asp Leu
            340                 345                 350

Arg Arg Phe Ala Arg Leu Glu Arg Gly Met Leu Leu Asp Asn His Ala
        355                 360                 365

Leu Tyr Asp Lys Thr Thr Asn Thr Phe Leu Gln Ala Lys Thr Glu Glu
    370                 375                 380

Asp Ile Phe Ala His Leu Gly Leu Asp Tyr Ile Glu Pro Trp Gln Arg
385                 390                 395                 400

Asn Ala

<210> SEQ ID NO 23
<211> LENGTH: 378
<212> TYPE: PRT
<213> ORGANISM: ARTIFICIAL SEQUENCE
<220> FEATURE:
<223> OTHER INFORMATION: F32 trunc wt (Anabas testudineus)

<400> SEQUENCE: 23

Ser Pro Ser Pro Val Pro Gly Ser Gln Asn Val Pro Ala Pro Ser Val
1               5                   10                  15

Ala Thr Val Ser Gln Tyr Ala Cys Gln Arg Arg Thr Thr Thr Glu Asn
            20                  25                  30

Asn Asn Lys Ile Leu Thr Asp Ala Phe Glu Val Leu Ala Glu Ser Tyr
        35                  40                  45

Glu Leu Asn Gln Leu Glu Gly Pro Cys Leu Ala Phe Arg Arg Ala Ala
    50                  55                  60

Ser Val Leu Lys Ser Leu Pro Trp Ala Val Gln Cys Leu Gly Ala Thr
65                  70                  75                  80

Gln Gly Leu Pro Cys Leu Gly Glu His Thr Lys Ala Leu Ile Glu Glu
                85                  90                  95

Ile Leu Gln Tyr Gly His Ser Phe Glu Val Glu Lys Ile Leu Ser Asp
            100                 105                 110

Glu Arg Tyr Gln Thr Leu Lys Leu Phe Thr Ser Val Phe Gly Val Gly
        115                 120                 125

Pro Lys Thr Ala Glu Lys Trp Tyr Arg Arg Gly Leu Arg Ser Phe Ser
    130                 135                 140

Asp Ile Leu Ala Glu Pro Ser Ile Gln Leu Asn Arg Met Gln Gln Ser
145                 150                 155                 160

Gly Phe Leu His Tyr Gly Asp Ile Ser Arg Ala Val Ser Lys Ala Glu

```
                165                 170                 175

Ala Arg Ala Leu Gly Asn Ile Ile Asp Glu Ala Val His Ala Ile Thr
            180                 185                 190

Pro Asp Gly Ile Leu Ala Leu Thr Gly Gly Phe Arg Arg Gly Lys Glu
        195                 200                 205

Phe Gly His Asp Val Asp Phe Ile Val Thr Thr Pro Glu Gln Gly Lys
    210                 215                 220

Glu Glu Thr Leu Leu Pro Asn Ile Ile Asp Arg Leu Lys Glu Gln Gly
225                 230                 235                 240

Ile Leu Leu Tyr Ser Asp Tyr Gln Thr Ser Thr Phe Asp Ile Ser Lys
                245                 250                 255

Leu Pro Ser His Lys Phe Glu Ala Met Asp His Phe Ala Lys Cys Phe
            260                 265                 270

Leu Ile Leu Arg Leu Glu Gly Ser Leu Val Asp Arg Gly Leu Asn Ser
        275                 280                 285

Thr Glu Gly Asp Ser Arg Gly Trp Arg Ala Val Arg Val Asp Leu Val
    290                 295                 300

Ser Pro Pro Met Glu Arg Tyr Ala Tyr Ala Leu Leu Gly Trp Thr Gly
305                 310                 315                 320

Ser Arg Gln Phe Glu Arg Asp Leu Arg Arg Phe Ala Arg Leu Glu Gln
                325                 330                 335

His Met Leu Leu Asp Asn His Ala Leu Tyr Asp Lys Thr Lys Lys Glu
            340                 345                 350

Phe Leu Ala Ala Thr Thr Glu Arg Asp Ile Phe Ala His Leu Gly Leu
        355                 360                 365

Glu Tyr Ile Glu Pro Trp Gln Arg Asn Ala
    370                 375


<210> SEQ ID NO 24
<211> LENGTH: 378
<212> TYPE: PRT
<213> ORGANISM: ARTIFICIAL SEQUENCE
<220> FEATURE:
<223> OTHER INFORMATION: F32 trunc new

<400> SEQUENCE: 24

Ser Pro Ser Pro Val Pro Gly Ser Gln Asn Val Pro Ala Pro Ser Val
1               5                   10                  15

Ala Thr Val Ser Gln Tyr Ala Cys Gln Arg Arg Thr Thr Thr Glu Asn
            20                  25                  30

Asn Asn Lys Ile Phe Thr Asp Ala Phe Glu Val Leu Ala Glu Ser Tyr
        35                  40                  45

Glu Phe Asn Glu Met Glu Glu Ser Arg Asp Ala Phe Arg Arg Ala Ala
    50                  55                  60

Ser Val Leu Lys Ser Leu Pro Trp Ala Val Gln Ser Leu Gly Ala Thr
65                  70                  75                  80

Gln Asp Leu Pro Cys Leu Gly Glu His Thr Lys Arg Val Met Glu Glu
                85                  90                  95

Ile Leu Gln Tyr Gly Arg Ser Phe Glu Val Glu Lys Ile Leu Ser Asp
            100                 105                 110

Glu Arg Tyr Gln Thr Leu Lys Leu Phe Thr Ser Val Phe Gly Val Gly
        115                 120                 125

Pro Lys Thr Ala Glu Lys Trp Tyr Arg Arg Gly Leu Arg Ser Phe Glu
    130                 135                 140

Asp Ile Arg Ala Glu Pro Ser Ile His Leu Asn Arg Met Gln Gln Ser
```

```
145                 150                 155                 160

Gly Phe Leu His Tyr Gly Asp Ile Ser Arg Ala Val Ser Lys Ala Glu
                165                 170                 175

Ala Arg Ala Leu Gly Asn Ile Ile Asp Glu Ala Val His Ala Ile Thr
            180                 185                 190

Pro Asp Ala Ile Leu Ala Leu Thr Gly Gly Phe Arg Leu Gly Lys Glu
        195                 200                 205

Phe Gly His Asp Val Asp Phe Ile Val Thr Thr Pro Glu Leu Gly Lys
    210                 215                 220

Glu Glu Ser Leu Leu Pro Asn Ile Ile Asp Arg Leu Lys Lys Gln Gly
225                 230                 235                 240

Ile Leu Leu Tyr Ser Asp Tyr Gln Ala Ser Thr Phe Asp Met Ser Lys
                245                 250                 255

Leu Pro Ser His Arg Phe Glu Ala Met Asp His Phe Ala Lys Cys Phe
            260                 265                 270

Leu Ile Leu Arg Leu Glu Gly Ser Gln Val Glu Gly Gly Leu Asn Ser
        275                 280                 285

Ala Glu Gly Asp Ser Arg Gly Trp Arg Ala Val Arg Val Asp Leu Val
    290                 295                 300

Ser Pro Pro Met Asp Arg Tyr Ala Phe Ala Leu Leu Gly Trp Thr Gly
305                 310                 315                 320

Ser Ala Phe Phe Asn Arg Asp Leu Arg Arg Phe Ala Arg Met Glu Arg
                325                 330                 335

Arg Met Leu Leu Asp Asn His Ala Leu Tyr Asp Lys Thr Lys Lys Glu
            340                 345                 350

Phe Leu Ala Ala Thr Thr Glu Lys Asp Ile Phe Ala His Leu Gly Leu
        355                 360                 365

Glu Tyr Ile Glu Pro Trp Gln Arg Asn Ala
    370                 375


<210> SEQ ID NO 25
<211> LENGTH: 403
<212> TYPE: PRT
<213> ORGANISM: ARTIFICIAL SEQUENCE
<220> FEATURE:
<223> OTHER INFORMATION: F32

<400> SEQUENCE: 25

Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30

Ser Gln Asn Val Pro Ala Pro Ser Val Ala Thr Val Ser Gln Tyr Ala
        35                  40                  45

Cys Gln Arg Arg Thr Thr Thr Glu Asn Asn Asn Lys Ile Phe Thr Asp
    50                  55                  60

Ala Phe Glu Val Leu Ala Glu Ser Tyr Glu Phe Asn Glu Met Glu Glu
65                  70                  75                  80

Ser Arg Asp Ala Phe Arg Arg Ala Ala Ser Val Leu Lys Ser Leu Pro
                85                  90                  95

Trp Ala Val Gln Ser Leu Gly Ala Thr Gln Asp Leu Pro Cys Leu Gly
            100                 105                 110

Glu His Thr Lys Arg Val Met Glu Glu Ile Leu Gln Tyr Gly Arg Ser
        115                 120                 125

Phe Glu Val Glu Lys Ile Leu Ser Asp Glu Arg Tyr Gln Thr Leu Lys
```

```
    130                 135                 140

Leu Phe Thr Ser Val Phe Gly Val Gly Pro Lys Thr Ala Glu Lys Trp
145                 150                 155                 160

Tyr Arg Arg Gly Leu Arg Ser Phe Glu Asp Ile Arg Ala Glu Pro Ser
                165                 170                 175

Ile His Leu Asn Arg Met Gln Gln Ser Gly Phe Leu His Tyr Gly Asp
            180                 185                 190

Ile Ser Arg Ala Val Ser Lys Ala Glu Ala Arg Ala Leu Gly Asn Ile
        195                 200                 205

Ile Asp Glu Ala Val His Ala Ile Thr Pro Asp Ala Ile Leu Ala Leu
    210                 215                 220

Thr Gly Gly Phe Arg Leu Gly Lys Glu Phe Gly His Asp Val Asp Phe
225                 230                 235                 240

Ile Val Thr Thr Pro Glu Leu Gly Lys Glu Glu Ser Leu Leu Pro Asn
                245                 250                 255

Ile Ile Asp Arg Leu Lys Lys Gln Gly Ile Leu Leu Tyr Ser Asp Tyr
            260                 265                 270

Gln Ala Ser Thr Phe Asp Met Ser Lys Leu Pro Ser His Arg Phe Glu
        275                 280                 285

Ala Met Asp His Phe Ala Lys Cys Phe Leu Ile Leu Arg Leu Glu Gly
    290                 295                 300

Ser Gln Val Glu Gly Gly Leu Asn Ser Ala Glu Gly Asp Ser Arg Gly
305                 310                 315                 320

Trp Arg Ala Val Arg Val Asp Leu Val Ser Pro Pro Met Asp Arg Tyr
                325                 330                 335

Ala Phe Ala Leu Leu Gly Trp Thr Gly Ser Ala Phe Phe Asn Arg Asp
            340                 345                 350

Leu Arg Arg Phe Ala Arg Met Glu Arg Arg Met Leu Leu Asp Asn His
        355                 360                 365

Ala Leu Tyr Asp Lys Thr Lys Lys Glu Phe Leu Ala Ala Thr Thr Glu
    370                 375                 380

Lys Asp Ile Phe Ala His Leu Gly Leu Glu Tyr Ile Glu Pro Trp Gln
385                 390                 395                 400

Arg Asn Ala


<210> SEQ ID NO 26
<211> LENGTH: 378
<212> TYPE: PRT
<213> ORGANISM: ARTIFICIAL SEQUENCE
<220> FEATURE:
<223> OTHER INFORMATION: F57 trunc wt

<400> SEQUENCE: 26

Ser Pro Ser Pro Val Pro Gly Ser Gln Asn Val Pro Ala Pro Ser Val
1               5                   10                  15

Asp Lys Val Ser Gln Tyr Ala Cys Gln Arg Arg Thr Thr Val Glu Asn
            20                  25                  30

Asn Asn Arg Ile Phe Thr Asp Ala Phe Glu Val Leu Ala Glu Asn Tyr
        35                  40                  45

Glu Phe Asn Glu Ile Glu Gly Arg Cys Leu Ala Phe Arg Arg Ala Ala
    50                  55                  60

Ser Val Leu Lys Ser Leu Pro Trp Ala Val Arg Ser Val Gly Ala Thr
65                  70                  75                  80

Leu Asp Leu Pro Cys Leu Gly Glu His Thr Thr Ala Val Met Lys Glu
                85                  90                  95
```

```
Ile Leu Gln Tyr Gly Arg Ser Phe Glu Val Glu Lys Ile Leu Ser Asp
            100                 105                 110

Glu Arg Cys Gln Thr Leu Lys Leu Phe Thr Ser Val Phe Gly Val Gly
        115                 120                 125

Pro Lys Thr Ala Glu Lys Trp Tyr Arg Arg Gly Leu Arg Ser Phe Ser
    130                 135                 140

Asp Val Leu Ala Gln Pro Gly Ile His Leu Asn Arg Met Gln Gln Ser
145                 150                 155                 160

Gly Phe Leu His Tyr Gly Asp Ile Ser Arg Ala Val Ser Lys Ala Glu
                165                 170                 175

Ala Arg Ala Val Gly Asn Ile Ile Asp Glu Ala Val His Val Ile Thr
            180                 185                 190

Pro Asn Ala Ile Leu Ala Leu Thr Gly Gly Phe Arg Arg Gly Lys Asp
        195                 200                 205

Phe Gly His Asp Val Asp Phe Ile Val Thr Thr Thr Glu Leu Gly Lys
    210                 215                 220

Glu Lys Asn Leu Leu Ile Ser Val Ile Glu Ser Leu Lys Lys Gln Gly
225                 230                 235                 240

Leu Leu Leu Phe Ser Asp Tyr Gln Ala Ser Thr Phe Asp Ile Ser Lys
                245                 250                 255

Leu Pro Ser His Arg Phe Glu Ala Met Asp His Phe Ala Lys Cys Phe
            260                 265                 270

Leu Ile Leu Arg Leu Glu Gly Ser Arg Val Glu Gly Gly Leu Gln Arg
        275                 280                 285

Ala Gln Ala Asp Gly Arg Gly Trp Arg Ala Val Arg Val Asp Leu Val
    290                 295                 300

Ser Pro Pro Ala Asp Arg Phe Ala Phe Thr Met Leu Gly Trp Thr Gly
305                 310                 315                 320

Ser Arg Met Phe Glu Arg Asp Leu Arg Arg Phe Ala Arg Leu Glu Arg
                325                 330                 335

Gln Met Leu Leu Asp Asn His Ala Leu Tyr Asp Lys Thr Lys Lys Glu
            340                 345                 350

Phe Leu Thr Ala Ala Thr Glu Lys Asp Ile Phe Asp His Leu Gly Leu
        355                 360                 365

Glu Tyr Ile Glu Pro Trp Gln Arg Asn Ala
    370                 375
```

<210> SEQ ID NO 27
<211> LENGTH: 383
<212> TYPE: PRT
<213> ORGANISM: ARTIFICIAL SEQUENCE
<220> FEATURE:
<223> OTHER INFORMATION: F57 trunc new (Poecilia reticulate)

<400> SEQUENCE: 27

```
Ser Pro Ser Pro Val Pro Gly Ser Gln Asn Val Pro Ala Pro Ser Val
1               5                   10                  15

Asp Lys Ile Ser Gln Tyr Ala Cys Gln Arg Arg Thr Thr Leu Asn Asn
            20                  25                  30

Tyr Asn Lys Lys Phe Thr Asp Ala Phe Glu Ile Leu Ala Glu Asn Tyr
        35                  40                  45

Glu Phe Asn Glu Asn Lys Gly Phe Cys Leu Ala Phe Arg Arg Ala Ala
    50                  55                  60

Ser Val Leu Lys Phe Leu Pro Phe Thr Ile Val Arg Met Asn Asp Ile
65                  70                  75                  80
```

Gln Gly Leu Pro Trp Met Gly Asp Gln Val Lys Arg Val Ile Glu Glu
85 90 95

Ile Leu Glu Glu Gly Glu Ser Ser Lys Val Lys Glu Val Leu Asn Asp
100 105 110

Glu Lys Tyr Lys Ala Phe Lys Leu Phe Thr Ser Val Phe Gly Val Gly
115 120 125

Arg Lys Thr Ser Glu Lys Trp Tyr Arg Met Gly Leu Arg Thr Leu Glu
130 135 140

Glu Val Lys Ala Asp Lys Thr Leu Lys Leu Thr Lys Met Gln Lys Ala
145 150 155 160

Gly Phe Leu Tyr Tyr Glu Asp Leu Ile Ser Arg Val Ser Lys Ala Glu
165 170 175

Ala Asp Ala Val Ser Leu Ile Val Lys Asp Thr Val Trp Lys Phe Leu
180 185 190

Pro Asp Ala Leu Val Thr Leu Thr Gly Gly Phe Arg Leu Gly Lys Lys
195 200 205

Met Gly His Asp Val Asp Phe Leu Ile Thr Thr Pro Gly Pro Glu Glu
210 215 220

Glu Glu Glu Leu Leu His Lys Val Ile Asp Leu Trp Lys Lys Gln Gly
225 230 235 240

Leu Leu Leu Tyr Tyr Asp Ile Ile Glu Ser Thr Phe Glu Lys Thr Lys
245 250 255

Leu Pro Ser Arg Thr Val Asp Ala Leu Asp His Phe Gln Lys Cys Phe
260 265 270

Ala Ile Leu Lys Leu His Lys Gln Arg Val Asp Asn Gly Asn Ser Asn
275 280 285

Gln Ser Lys Glu Phe Asp Lys Glu Glu Thr Lys Asp Trp Lys Ala Ile
290 295 300

Arg Val Asp Leu Val Ile Thr Pro Phe Glu Gln Tyr Ala Tyr Ala Leu
305 310 315 320

Leu Gly Trp Thr Gly Ser Ala Phe Phe Asn Arg Asp Leu Arg Arg Tyr
325 330 335

Ala Thr His Glu Lys Lys Met Met Leu Asp Asn His Ala Leu Tyr Asp
340 345 350

Lys Thr Lys Arg Ile Phe Leu Lys Ala Ala Ser Glu Glu Glu Ile Phe
355 360 365

Ala His Leu Gly Leu Asp Tyr Leu Glu Pro Trp Glu Arg Asn Ala
370 375 380

<210> SEQ ID NO 28
<211> LENGTH: 408
<212> TYPE: PRT
<213> ORGANISM: ARTIFICIAL SEQUNECE
<220> FEATURE:
<223> OTHER INFORMATION: F57

<400> SEQUENCE: 28

Met Ala Ser Ser His His His His His His Ser Ser Gly Ser Glu Asn
1 5 10 15

Leu Tyr Phe Gln Thr Gly Ser Ser Gly Ser Pro Ser Pro Val Pro Gly
20 25 30

Ser Gln Asn Val Pro Ala Pro Ser Val Asp Lys Ile Ser Gln Tyr Ala
35 40 45

Cys Gln Arg Arg Thr Thr Leu Asn Asn Tyr Asn Lys Lys Phe Thr Asp
50 55 60

-continued

```
Ala Phe Glu Ile Leu Ala Glu Asn Tyr Glu Phe Asn Glu Asn Lys Gly
65                  70                  75                  80

Phe Cys Leu Ala Phe Arg Arg Ala Ala Ser Val Leu Lys Phe Leu Pro
                85                  90                  95

Phe Thr Ile Val Arg Met Asn Asp Ile Gln Gly Leu Pro Trp Met Gly
            100                 105                 110

Asp Gln Val Lys Arg Val Ile Glu Glu Ile Leu Glu Glu Gly Glu Ser
        115                 120                 125

Ser Lys Val Lys Glu Val Leu Asn Asp Glu Lys Tyr Lys Ala Phe Lys
    130                 135                 140

Leu Phe Thr Ser Val Phe Gly Val Gly Arg Lys Thr Ser Glu Lys Trp
145                 150                 155                 160

Tyr Arg Met Gly Leu Arg Thr Leu Glu Glu Val Lys Ala Asp Lys Thr
                165                 170                 175

Leu Lys Leu Thr Lys Met Gln Lys Ala Gly Phe Leu Tyr Tyr Glu Asp
            180                 185                 190

Leu Ile Ser Arg Val Ser Lys Ala Glu Ala Asp Ala Val Ser Leu Ile
        195                 200                 205

Val Lys Asp Thr Val Trp Lys Phe Leu Pro Asp Ala Leu Val Thr Leu
    210                 215                 220

Thr Gly Gly Phe Arg Leu Gly Lys Lys Met Gly His Asp Val Asp Phe
225                 230                 235                 240

Leu Ile Thr Thr Pro Gly Pro Glu Glu Glu Glu Glu Leu Leu His Lys
                245                 250                 255

Val Ile Asp Leu Trp Lys Lys Gln Gly Leu Leu Leu Tyr Tyr Asp Ile
            260                 265                 270

Ile Glu Ser Thr Phe Glu Lys Thr Lys Leu Pro Ser Arg Thr Val Asp
        275                 280                 285

Ala Leu Asp His Phe Gln Lys Cys Phe Ala Ile Leu Lys Leu His Lys
    290                 295                 300

Gln Arg Val Asp Asn Gly Asn Ser Asn Gln Ser Lys Glu Phe Asp Lys
305                 310                 315                 320

Glu Glu Thr Lys Asp Trp Lys Ala Ile Arg Val Asp Leu Val Ile Thr
                325                 330                 335

Pro Phe Glu Gln Tyr Ala Tyr Ala Leu Leu Gly Trp Thr Gly Ser Ala
            340                 345                 350

Phe Phe Asn Arg Asp Leu Arg Arg Tyr Ala Thr His Glu Lys Lys Met
        355                 360                 365

Met Leu Asp Asn His Ala Leu Tyr Asp Lys Thr Lys Arg Ile Phe Leu
    370                 375                 380

Lys Ala Ala Ser Glu Glu Glu Ile Phe Ala His Leu Gly Leu Asp Tyr
385                 390                 395                 400

Leu Glu Pro Trp Glu Arg Asn Ala
                405
```

<210> SEQ ID NO 29
<211> LENGTH: 366
<212> TYPE: PRT
<213> ORGANISM: ARTIFICIAL SEQUENCE
<220> FEATURE:
<223> OTHER INFORMATION: N100 trunc wt (short Rattus norvegicus)

<400> SEQUENCE: 29

```
Pro Leu Met Gln Lys Ile Ser Gln Tyr Ala Cys Gln Arg Arg Thr Thr
1               5                   10                  15
```

```
Leu Asn Asn His Asn Gln Leu Phe Thr Asp Ala Phe Asp Ile Leu Ala
            20                  25                  30

Glu Asn Tyr Glu Phe Arg Glu Asn Glu Val Ser Cys Leu Pro Phe Met
        35                  40                  45

Arg Ala Ala Ser Val Leu Lys Ser Leu Ser Phe Pro Ile Val Ser Met
    50                  55                  60

Lys Asp Ile Glu Gly Ile Pro Cys Leu Gly Asp Lys Val Lys Cys Val
65                  70                  75                  80

Ile Glu Gly Ile Ile Glu Asp Gly Glu Ser Ser Glu Val Lys Ala Val
                85                  90                  95

Leu Asn Asp Glu Arg Tyr Lys Ser Phe Lys Leu Phe Thr Ser Val Phe
            100                 105                 110

Gly Val Gly Leu Lys Thr Ala Glu Lys Trp Phe Arg Met Gly Phe Arg
        115                 120                 125

Thr Leu Ser Lys Ile Lys Ser Asp Lys Ser Leu Arg Phe Thr His Met
    130                 135                 140

Gln Lys Ala Gly Phe Leu Tyr Tyr Glu Asp Leu Val Ser Cys Val Asn
145                 150                 155                 160

Arg Ala Glu Ala Glu Ala Val Ser Met Leu Val Lys Glu Ala Val Val
                165                 170                 175

Ala Phe Leu Pro Asp Ala Leu Val Thr Met Thr Gly Gly Phe Arg Arg
            180                 185                 190

Gly Lys Met Thr Gly His Asp Val Asp Phe Leu Ile Thr Ser Pro Glu
        195                 200                 205

Ala Thr Glu Glu Glu Glu Gln Gln Leu Leu His Lys Val Thr Asn Phe
    210                 215                 220

Trp Arg Gln Gln Gly Leu Leu Leu Tyr Cys Asp Ile Ile Glu Ser Thr
225                 230                 235                 240

Phe Glu Lys Phe Lys Leu Pro Ser Arg Lys Val Asp Ala Leu Asp His
                245                 250                 255

Phe Gln Lys Cys Phe Leu Ile Leu Lys Leu His Arg Gly Leu Val Arg
            260                 265                 270

Ser Glu Glu Ser Gly Gln Gln Glu Gly Lys Asp Trp Lys Ala Ile Arg
        275                 280                 285

Val Asp Leu Val Met Cys Pro Tyr Glu Arg Arg Ala Phe Ala Leu Leu
    290                 295                 300

Gly Trp Thr Gly Ser Arg Gln Phe Glu Arg Asp Leu Arg Arg Tyr Ala
305                 310                 315                 320

Thr His Glu Arg Lys Met Met Leu Asp Asn His Ala Leu Tyr Asp Lys
                325                 330                 335

Thr Lys Arg Val Phe Leu Glu Ala Glu Ser Glu Glu Glu Ile Phe Ala
            340                 345                 350

His Leu Gly Leu Asp Tyr Ile Glu Pro Trp Glu Arg Asn Ala
        355                 360                 365
```

<210> SEQ ID NO 30
<211> LENGTH: 366
<212> TYPE: PRT
<213> ORGANISM: ARTIFICIAL SEQUENCE
<220> FEATURE:
<223> OTHER INFORMATION: N100 trunc new

<400> SEQUENCE: 30

```
Ser Val Val Gln Lys Ile Ser Glu Tyr Ala Cys Gln Arg Arg Thr Thr
1               5                   10                  15
```

-continued

```
Leu Asn Asn His Asn Glu Val Phe Thr Arg Ala Phe Asp Ile Leu Ala
            20                  25                  30

Glu Asn Tyr Glu Phe Arg Glu Asn Glu Glu Ser Arg Asp Ala Phe Arg
        35                  40                  45

Arg Ala Ser Ser Val Leu Lys Ser Leu Pro Phe Pro Ile Ile Ser Met
    50                  55                  60

Lys Asp Thr Glu Gly Ile Pro Cys Leu Gly Asp Lys Val Lys Arg Val
65                  70                  75                  80

Ile Glu Glu Ile Ile Glu Asp Gly Glu Ser Ser Glu Val Lys Ala Val
                85                  90                  95

Leu Asn Asp Glu Arg Tyr Lys Ala Phe Lys Leu Phe Thr Ser Val Phe
            100                 105                 110

Gly Val Gly Arg Lys Thr Ala Glu Lys Trp Phe Arg Met Gly Phe Arg
        115                 120                 125

Thr Leu Glu Lys Ile Lys Ser Asp Lys Ser Leu Arg Phe Thr Gln Met
    130                 135                 140

Gln Lys Ala Gly Phe Leu Tyr Tyr Glu Asp Leu Ala Glu Arg Val Asn
145                 150                 155                 160

Arg Ala Glu Ala Glu Ala Ile Glu Met Leu Val Lys Glu Ala Val Val
                165                 170                 175

Ala Phe Leu Pro Asp Ala Leu Val Thr Met Thr Gly Gly Phe Arg Leu
            180                 185                 190

Gly Lys Met Thr Gly His Asp Val Asp Phe Leu Ile Thr Ser Pro Glu
        195                 200                 205

Ala Thr Glu Glu Glu Glu Gln Gln Leu Leu His Lys Val Thr Asp Phe
    210                 215                 220

Trp Arg Gln Gln Gly Leu Leu Leu Tyr Cys Asp Ile Ile Glu Ser Thr
225                 230                 235                 240

Phe Glu Lys Phe Lys Leu Pro Ser Arg Thr Val Asp Ala Leu Asp His
                245                 250                 255

Phe Gln Lys Cys Phe Leu Ile Leu Lys Leu His His Gly Arg Val Val
            260                 265                 270

Ser Glu Lys Ser Gly Gln Gln Glu Gly Lys Gly Trp Lys Ala Ile Arg
        275                 280                 285

Val Asp Leu Val Met Cys Pro Tyr Glu Arg Arg Ala Phe Ala Leu Leu
    290                 295                 300

Gly Trp Thr Gly Ser Pro Phe Phe Asn Arg Asp Leu Arg Arg Tyr Ala
305                 310                 315                 320

Thr His Glu Arg Lys Met Met Leu Asp Asn His Ala Leu Tyr Asp Lys
                325                 330                 335

Thr Lys Arg Val Phe Leu Glu Ala Glu Ser Glu Glu Glu Ile Phe Ala
            340                 345                 350

His Leu Gly Leu Asp Tyr Ile Glu Pro Trp Glu Arg Asn Ala
        355                 360                 365
```

<210> SEQ ID NO 31
<211> LENGTH: 391
<212> TYPE: PRT
<213> ORGANISM: ARTIFICIAL SEQUENCE
<220> FEATURE:
<223> OTHER INFORMATION: N100

<400> SEQUENCE: 31

```
Met Ala Ser Ser His His His His His His Ser Ser Gly Ser Glu Asn
1               5                   10                  15
```

-continued

```
Leu Tyr Phe Gln Thr Gly Ser Ser Gly Ser Val Val Gln Lys Ile Ser
            20                  25                  30

Glu Tyr Ala Cys Gln Arg Arg Thr Thr Leu Asn Asn His Asn Glu Val
        35                  40                  45

Phe Thr Arg Ala Phe Asp Ile Leu Ala Glu Asn Tyr Glu Phe Arg Glu
    50                  55                  60

Asn Glu Glu Ser Arg Asp Ala Phe Arg Arg Ala Ser Ser Val Leu Lys
65                  70                  75                  80

Ser Leu Pro Phe Pro Ile Ile Ser Met Lys Asp Thr Glu Gly Ile Pro
                85                  90                  95

Cys Leu Gly Asp Lys Val Lys Arg Val Ile Glu Glu Ile Ile Glu Asp
            100                 105                 110

Gly Glu Ser Ser Glu Val Lys Ala Val Leu Asn Asp Glu Arg Tyr Lys
        115                 120                 125

Ala Phe Lys Leu Phe Thr Ser Val Phe Gly Val Gly Arg Lys Thr Ala
    130                 135                 140

Glu Lys Trp Phe Arg Met Gly Phe Arg Thr Leu Glu Lys Ile Lys Ser
145                 150                 155                 160

Asp Lys Ser Leu Arg Phe Thr Gln Met Gln Lys Ala Gly Phe Leu Tyr
                165                 170                 175

Tyr Glu Asp Leu Ala Glu Arg Val Asn Arg Ala Glu Ala Glu Ala Ile
            180                 185                 190

Glu Met Leu Val Lys Glu Ala Val Val Ala Phe Leu Pro Asp Ala Leu
        195                 200                 205

Val Thr Met Thr Gly Gly Phe Arg Leu Gly Lys Met Thr Gly His Asp
    210                 215                 220

Val Asp Phe Leu Ile Thr Ser Pro Glu Ala Thr Glu Glu Glu Glu Gln
225                 230                 235                 240

Gln Leu Leu His Lys Val Thr Asp Phe Trp Arg Gln Gln Gly Leu Leu
                245                 250                 255

Leu Tyr Cys Asp Ile Ile Glu Ser Thr Phe Glu Lys Phe Lys Leu Pro
            260                 265                 270

Ser Arg Thr Val Asp Ala Leu Asp His Phe Gln Lys Cys Phe Leu Ile
        275                 280                 285

Leu Lys Leu His His Gly Arg Val Val Ser Glu Lys Ser Gly Gln Gln
    290                 295                 300

Glu Gly Lys Gly Trp Lys Ala Ile Arg Val Asp Leu Val Met Cys Pro
305                 310                 315                 320

Tyr Glu Arg Arg Ala Phe Ala Leu Leu Gly Trp Thr Gly Ser Pro Phe
                325                 330                 335

Phe Asn Arg Asp Leu Arg Arg Tyr Ala Thr His Glu Arg Lys Met Met
            340                 345                 350

Leu Asp Asn His Ala Leu Tyr Asp Lys Thr Lys Arg Val Phe Leu Glu
        355                 360                 365

Ala Glu Ser Glu Glu Glu Ile Phe Ala His Leu Gly Leu Asp Tyr Ile
    370                 375                 380

Glu Pro Trp Glu Arg Asn Ala
385                 390
```

<210> SEQ ID NO 32
<211> LENGTH: 379
<212> TYPE: PRT
<213> ORGANISM: ARTIFICIAL SEQUNECE
<220> FEATURE:

<223> OTHER INFORMATION: N100or trunk wt (long Rattus norvegicus)

<400> SEQUENCE: 32

```
Ser Leu Ser Pro Val Pro Gly Ser Gln Thr Val Pro Pro Pro Leu Met
1               5                   10                  15

Gln Lys Ile Ser Gln Tyr Ala Cys Gln Arg Arg Thr Thr Leu Asn Asn
            20                  25                  30

His Asn Gln Leu Phe Thr Asp Ala Phe Asp Ile Leu Ala Glu Asn Tyr
        35                  40                  45

Glu Phe Arg Glu Asn Glu Val Ser Cys Leu Pro Phe Met Arg Ala Ala
    50                  55                  60

Ser Val Leu Lys Ser Leu Ser Phe Pro Ile Val Ser Met Lys Asp Ile
65                  70                  75                  80

Glu Gly Ile Pro Cys Leu Gly Asp Lys Val Lys Cys Val Ile Glu Gly
                85                  90                  95

Ile Ile Glu Asp Gly Glu Ser Ser Glu Val Lys Ala Val Leu Asn Asp
            100                 105                 110

Glu Arg Tyr Lys Ser Phe Lys Leu Phe Thr Ser Val Phe Gly Val Gly
        115                 120                 125

Leu Lys Thr Ala Glu Lys Trp Phe Arg Met Gly Phe Arg Thr Leu Ser
    130                 135                 140

Lys Ile Lys Ser Asp Lys Ser Leu Arg Phe Thr His Met Gln Lys Ala
145                 150                 155                 160

Gly Phe Leu Tyr Tyr Glu Asp Leu Val Ser Cys Val Asn Arg Ala Glu
                165                 170                 175

Ala Glu Ala Val Ser Met Leu Val Lys Glu Ala Val Val Ala Phe Leu
            180                 185                 190

Pro Asp Ala Leu Val Thr Met Thr Gly Gly Phe Arg Arg Gly Lys Met
        195                 200                 205

Thr Gly His Asp Val Asp Phe Leu Ile Thr Ser Pro Glu Ala Thr Glu
    210                 215                 220

Glu Glu Glu Gln Gln Leu Leu His Lys Val Thr Asn Phe Trp Arg Gln
225                 230                 235                 240

Gln Gly Leu Leu Leu Tyr Cys Asp Ile Ile Glu Ser Thr Phe Glu Lys
                245                 250                 255

Phe Lys Leu Pro Ser Arg Lys Val Asp Ala Leu Asp His Phe Gln Lys
            260                 265                 270

Cys Phe Leu Ile Leu Lys Leu His Arg Gly Leu Val Arg Ser Glu Glu
        275                 280                 285

Ser Gly Gln Gln Glu Gly Lys Asp Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Arg Gln Phe Glu Arg Asp Leu Arg Arg Tyr Ala Thr His Glu
                325                 330                 335

Arg Lys Met Met Leu Asp Asn His Ala Leu Tyr Asp Lys Thr Lys Arg
            340                 345                 350

Val Phe Leu Glu Ala Glu Ser Glu Glu Glu Ile Phe Ala His Leu Gly
        355                 360                 365

Leu Asp Tyr Ile Glu Pro Trp Glu Arg Asn Ala
    370                 375
```

<210> SEQ ID NO 33
<211> LENGTH: 379

-continued

<212> TYPE: PRT
<213> ORGANISM: ARTIFICIAL SEQUENCE
<220> FEATURE:
<223> OTHER INFORMATION: N100or trunc new

<400> SEQUENCE: 33

```
Ser Pro Ser Pro Val Pro Gly Ser Gln Asn Val Pro Ala Pro Val Val
1               5                   10                  15

Gln Lys Ile Ser Glu Tyr Ala Cys Gln Arg Arg Thr Thr Leu Asn Asn
            20                  25                  30

His Asn Glu Leu Phe Thr Arg Ala Phe Asp Ile Leu Ala Glu Asn Tyr
        35                  40                  45

Glu Phe Arg Glu Asn Glu Glu Ser Arg Asp Ala Phe Arg Arg Ala Ala
    50                  55                  60

Ser Val Leu Lys Ser Leu Ser Phe Pro Ile Val Ser Met Lys Asp Ile
65                  70                  75                  80

Glu Gly Ile Pro Cys Leu Gly Asp Lys Val Lys Arg Ile Ile Glu Glu
                85                  90                  95

Ile Ile Glu Asp Gly Glu Ser Ser Glu Val Lys Ala Val Leu Asn Asp
            100                 105                 110

Glu Arg Tyr Lys Ala Phe Lys Leu Phe Thr Ser Val Phe Gly Val Gly
        115                 120                 125

Arg Lys Thr Ala Glu Lys Trp Phe Arg Met Gly Phe Arg Thr Leu Glu
    130                 135                 140

Lys Ile Arg Ser Asp Lys Ser Leu Arg Phe Thr His Met Gln Lys Ala
145                 150                 155                 160

Gly Phe Leu Tyr Tyr Glu Asp Leu Val Ser Arg Val Asn Arg Ala Glu
                165                 170                 175

Ala Glu Ala Val Ser Met Leu Val Lys Glu Ala Val Val Ala Phe Leu
            180                 185                 190

Pro Asp Ala Leu Val Thr Met Thr Gly Gly Phe Arg Leu Gly Lys Met
        195                 200                 205

Thr Gly His Asp Val Asp Phe Leu Ile Thr Ser Pro Glu Ala Thr Glu
    210                 215                 220

Glu Glu Glu Gln Gln Leu Leu His Lys Val Thr Asn Phe Trp Arg Gln
225                 230                 235                 240

Gln Gly Leu Leu Leu Tyr Cys Asp Ile Ile Glu Ser Thr Phe Glu Lys
                245                 250                 255

Phe Lys Leu Pro Ser Arg Thr Val Asp Ala Leu Asp His Phe Gln Lys
            260                 265                 270

Cys Phe Leu Ile Leu Lys Leu His Arg Gly Leu Val Arg Ser Glu Glu
        275                 280                 285

Ser Gly Gln Gln Glu Gly Lys Asp Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Pro Phe Phe Asn Arg Asp Leu Arg Arg Tyr Ala Thr His Glu
                325                 330                 335

Arg Lys Met Met Leu Asp Asn His Ala Leu Tyr Asp Lys Thr Lys Arg
            340                 345                 350

Val Phe Leu Glu Ala Glu Ser Glu Glu Glu Ile Phe Ala His Leu Gly
        355                 360                 365

Leu Asp Tyr Ile Glu Pro Trp Glu Arg Asn Ala
    370                 375
```

<210> SEQ ID NO 34
<211> LENGTH: 404
<212> TYPE: PRT
<213> ORGANISM: ARTIFICIAL SEQUENCE
<220> FEATURE:
<223> OTHER INFORMATION: N100or

<400> SEQUENCE: 34

```
Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30

Ser Gln Asn Val Pro Ala Pro Val Val Gln Lys Ile Ser Glu Tyr Ala
        35                  40                  45

Cys Gln Arg Arg Thr Thr Leu Asn Asn His Asn Glu Leu Phe Thr Arg
    50                  55                  60

Ala Phe Asp Ile Leu Ala Glu Asn Tyr Glu Phe Arg Glu Asn Glu Glu
65                  70                  75                  80

Ser Arg Asp Ala Phe Arg Arg Ala Ala Ser Val Leu Lys Ser Leu Ser
                85                  90                  95

Phe Pro Ile Val Ser Met Lys Asp Ile Glu Gly Ile Pro Cys Leu Gly
            100                 105                 110

Asp Lys Val Lys Arg Ile Ile Glu Glu Ile Ile Glu Asp Gly Glu Ser
        115                 120                 125

Ser Glu Val Lys Ala Val Leu Asn Asp Glu Arg Tyr Lys Ala Phe Lys
    130                 135                 140

Leu Phe Thr Ser Val Phe Gly Val Gly Arg Lys Thr Ala Glu Lys Trp
145                 150                 155                 160

Phe Arg Met Gly Phe Arg Thr Leu Glu Lys Ile Arg Ser Asp Lys Ser
                165                 170                 175

Leu Arg Phe Thr His Met Gln Lys Ala Gly Phe Leu Tyr Tyr Glu Asp
            180                 185                 190

Leu Val Ser Arg Val Asn Arg Ala Glu Ala Glu Ala Val Ser Met Leu
        195                 200                 205

Val Lys Glu Ala Val Val Ala Phe Leu Pro Asp Ala Leu Val Thr Met
    210                 215                 220

Thr Gly Gly Phe Arg Leu Gly Lys Met Thr Gly His Asp Val Asp Phe
225                 230                 235                 240

Leu Ile Thr Ser Pro Glu Ala Thr Glu Glu Glu Glu Gln Gln Leu Leu
                245                 250                 255

His Lys Val Thr Asn Phe Trp Arg Gln Gln Gly Leu Leu Leu Tyr Cys
            260                 265                 270

Asp Ile Ile Glu Ser Thr Phe Glu Lys Phe Lys Leu Pro Ser Arg Thr
        275                 280                 285

Val Asp Ala Leu Asp His Phe Gln Lys Cys Phe Leu Ile Leu Lys Leu
    290                 295                 300

His Arg Gly Leu Val Arg Ser Glu Glu Ser Gly Gln Gln Glu Gly Lys
305                 310                 315                 320

Asp Trp Lys Ala Ile Arg Val Asp Leu Val Met Cys Pro Tyr Glu Arg
                325                 330                 335

Arg Ala Phe Ala Leu Leu Gly Trp Thr Gly Ser Pro Phe Phe Asn Arg
            340                 345                 350

Asp Leu Arg Arg Tyr Ala Thr His Glu Arg Lys Met Met Leu Asp Asn
        355                 360                 365
```

```
His Ala Leu Tyr Asp Lys Thr Lys Arg Val Phe Leu Glu Ala Glu Ser
    370                 375                 380

Glu Glu Glu Ile Phe Ala His Leu Gly Leu Asp Tyr Ile Glu Pro Trp
385                 390                 395                 400

Glu Arg Asn Ala


<210> SEQ ID NO 35
<211> LENGTH: 379
<212> TYPE: PRT
<213> ORGANISM: ARTIFICIAL SEQUENCE
<220> FEATURE:
<223> OTHER INFORMATION: N14 trunc wt (Piliocolobus tephrosceles)

<400> SEQUENCE: 35

Ser Asp Ser Thr Asn Pro Gly Leu Pro Lys Thr Pro Pro Thr Ala Ile
1               5                   10                  15

Gln Lys Ile Ser Gln Tyr Ala Cys Gln Arg Arg Thr Thr Leu Asn Asn
            20                  25                  30

Cys Asn Gln Ile Phe Thr Asp Ala Phe Asp Ile Leu Ala Glu Asn Cys
        35                  40                  45

Glu Phe Arg Glu Asn Glu Asp Ser Cys Val Thr Phe Met Arg Ala Ala
    50                  55                  60

Ser Val Leu Lys Ser Leu Pro Phe Thr Ile Ile Ser Met Lys Asp Thr
65                  70                  75                  80

Glu Gly Ile Pro Cys Leu Gly Ser Lys Val Lys Cys Ile Ile Glu Glu
                85                  90                  95

Ile Ile Glu Asp Gly Glu Ser Ser Glu Val Lys Ala Val Leu Asn Asp
            100                 105                 110

Glu Arg Tyr Gln Ser Phe Lys Leu Phe Thr Ser Val Phe Gly Val Gly
        115                 120                 125

Leu Lys Thr Ser Glu Lys Trp Phe Arg Met Gly Phe Arg Thr Leu Ser
    130                 135                 140

Lys Val Arg Ser Asp Glu Ser Leu Lys Phe Thr Arg Met Gln Arg Ala
145                 150                 155                 160

Gly Phe Leu Tyr Tyr Glu Asp Leu Val Ser Cys Val Thr Arg Ala Glu
                165                 170                 175

Ala Glu Ala Val Ser Ala Leu Val Lys Glu Ala Val Trp Ala Phe Leu
            180                 185                 190

Pro Asp Ala Phe Val Thr Met Thr Gly Gly Phe Arg Arg Gly Lys Lys
        195                 200                 205

Met Gly His Asp Val Asp Phe Leu Ile Thr Ser Pro Gly Ser Thr Glu
    210                 215                 220

Asp Glu Glu Gln Gln Leu Leu Gln Lys Val Met Asn Leu Trp Glu Lys
225                 230                 235                 240

Lys Gly Leu Leu Leu Tyr Tyr Asp Leu Val Glu Ser Thr Phe Glu Lys
                245                 250                 255

Leu Arg Leu Pro Ser Arg Lys Val Asp Ala Leu Asp His Phe Gln Lys
            260                 265                 270

Cys Phe Leu Ile Phe Lys Leu Pro Leu Gln Arg Val Asp Ser Asp Gln
        275                 280                 285

Ser Ser Trp Gln Gly Gly Lys Thr Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Arg Gln Phe Glu Arg Asp Leu Arg Arg Tyr Ala Thr His Glu
```

```
                325                 330                 335

Arg Lys Met Ile Leu Asp Asn His Ala Leu Tyr Asp Lys Thr Lys Arg
            340                 345                 350

Ile Phe Leu Lys Ala Glu Ser Glu Glu Glu Ile Phe Ala His Leu Gly
        355                 360                 365

Leu Asp Tyr Ile Glu Pro Trp Glu Arg Asn Ala
    370                 375


<210> SEQ ID NO 36
<211> LENGTH: 379
<212> TYPE: PRT
<213> ORGANISM: ARTIFICIAL SEQUENCE
<220> FEATURE:
<223> OTHER INFORMATION: N14 trunc new

<400> SEQUENCE: 36

Ser Pro Ser Pro Val Pro Gly Ser Gln Asn Val Pro Ala Pro Val Val
1               5                   10                  15

Gln Lys Ile Ser Gln Tyr Ala Cys Gln Arg Arg Thr Thr Leu Asn Asn
            20                  25                  30

Tyr Asn Glu Ile Phe Thr Arg Ala Phe Asp Ile Leu Ala Glu Asn Ser
        35                  40                  45

Glu Phe Arg Glu Asn Glu Asp Ser Tyr Val Thr Phe Arg Arg Ala Ala
    50                  55                  60

Ser Val Leu Lys Ser Leu Pro Phe Thr Ile Ile Ser Met Lys Asp Thr
65                  70                  75                  80

Glu Gly Ile Pro Cys Leu Gly Ser Lys Val Lys Arg Ile Ile Glu Glu
                85                  90                  95

Ile Ile Glu Asp Gly Glu Ser Ser Glu Val Lys Ala Val Leu Asn Asp
            100                 105                 110

Glu Arg Tyr Gln Ala Phe Lys Leu Phe Thr Ser Val Phe Gly Val Gly
        115                 120                 125

Arg Lys Thr Ser Glu Lys Trp Phe Arg Met Gly Phe Arg Thr Leu Glu
    130                 135                 140

Lys Val Arg Ser Asp Glu Ser Leu Lys Phe Thr Arg Met Gln Arg Ala
145                 150                 155                 160

Gly Phe Leu Tyr Tyr Glu Asp Leu Val Ser Arg Val Thr Arg Ala Glu
                165                 170                 175

Ala Glu Ala Val Ser Val Leu Val Lys Glu Ala Val Trp Ala Phe Leu
            180                 185                 190

Pro Asp Ala Phe Val Thr Met Thr Gly Gly Phe Arg Leu Gly Lys Lys
        195                 200                 205

Met Gly His Asp Val Asp Phe Leu Ile Thr Ser Pro Gly Ser Thr Glu
    210                 215                 220

Asp Glu Glu Gln Gln Leu Leu Gln Lys Val Met Asn Leu Trp Glu Lys
225                 230                 235                 240

Lys Gly Leu Leu Leu Tyr Tyr Asp Leu Val Glu Ser Thr Phe Glu Lys
                245                 250                 255

Leu Arg Leu Pro Ser Arg Thr Val Asp Ala Leu Asp His Phe Gln Lys
            260                 265                 270

Cys Phe Leu Ile Phe Lys Leu Pro Leu Gln Arg Val Gly Ser Asp Gln
        275                 280                 285

Ser Ser Trp Gln Glu Gly Lys Thr Trp Lys Ala Ile Arg Val Asp Leu
    290                 295                 300

Val Met Cys Pro Tyr Glu Arg Arg Ala Phe Ala Leu Leu Gly Trp Thr
```

305 310 315 320

Gly Ser Ala Phe Phe Asn Arg Asp Leu Arg Arg Tyr Ala Thr His Glu
325 330 335

Arg Lys Met Ile Leu Asp Asn His Ala Leu Tyr Asp Lys Thr Lys Arg
340 345 350

Ile Phe Leu Lys Ala Glu Ser Glu Glu Glu Ile Phe Ala His Leu Gly
355 360 365

Leu Asp Tyr Ile Glu Pro Trp Glu Arg Asn Ala
370 375

<210> SEQ ID NO 37
<211> LENGTH: 404
<212> TYPE: PRT
<213> ORGANISM: ARTIFICIAL SEQUNECE
<220> FEATURE:
<223> OTHER INFORMATION: N14

<400> SEQUENCE: 37

Met Ala Ser Ser His His His His His His Ser Ser Gly Ser Glu Asn
1 5 10 15

Leu Tyr Phe Gln Thr Gly Ser Ser Gly Ser Pro Ser Pro Val Pro Gly
20 25 30

Ser Gln Asn Val Pro Ala Pro Val Val Gln Lys Ile Ser Gln Tyr Ala
35 40 45

Cys Gln Arg Arg Thr Thr Leu Asn Asn Tyr Asn Glu Ile Phe Thr Arg
50 55 60

Ala Phe Asp Ile Leu Ala Glu Asn Ser Glu Phe Arg Glu Asn Glu Asp
65 70 75 80

Ser Tyr Val Thr Phe Arg Arg Ala Ala Ser Val Leu Lys Ser Leu Pro
85 90 95

Phe Thr Ile Ile Ser Met Lys Asp Thr Glu Gly Ile Pro Cys Leu Gly
100 105 110

Ser Lys Val Lys Arg Ile Ile Glu Glu Ile Ile Glu Asp Gly Glu Ser
115 120 125

Ser Glu Val Lys Ala Val Leu Asn Asp Glu Arg Tyr Gln Ala Phe Lys
130 135 140

Leu Phe Thr Ser Val Phe Gly Val Gly Arg Lys Thr Ser Glu Lys Trp
145 150 155 160

Phe Arg Met Gly Phe Arg Thr Leu Glu Lys Val Arg Ser Asp Glu Ser
165 170 175

Leu Lys Phe Thr Arg Met Gln Arg Ala Gly Phe Leu Tyr Tyr Glu Asp
180 185 190

Leu Val Ser Arg Val Thr Arg Ala Glu Ala Glu Ala Val Ser Val Leu
195 200 205

Val Lys Glu Ala Val Trp Ala Phe Leu Pro Asp Ala Phe Val Thr Met
210 215 220

Thr Gly Gly Phe Arg Leu Gly Lys Lys Met Gly His Asp Val Asp Phe
225 230 235 240

Leu Ile Thr Ser Pro Gly Ser Thr Glu Asp Glu Glu Gln Gln Leu Leu
245 250 255

Gln Lys Val Met Asn Leu Trp Glu Lys Lys Gly Leu Leu Leu Tyr Tyr
260 265 270

Asp Leu Val Glu Ser Thr Phe Glu Lys Leu Arg Leu Pro Ser Arg Thr
275 280 285

Val Asp Ala Leu Asp His Phe Gln Lys Cys Phe Leu Ile Phe Lys Leu

```
    290                 295                 300

Pro Leu Gln Arg Val Gly Ser Asp Gln Ser Ser Trp Gln Glu Gly Lys
305                 310                 315                 320

Thr Trp Lys Ala Ile Arg Val Asp Leu Val Met Cys Pro Tyr Glu Arg
                325                 330                 335

Arg Ala Phe Ala Leu Leu Gly Trp Thr Gly Ser Ala Phe Phe Asn Arg
            340                 345                 350

Asp Leu Arg Arg Tyr Ala Thr His Glu Arg Lys Met Ile Leu Asp Asn
        355                 360                 365

His Ala Leu Tyr Asp Lys Thr Lys Arg Ile Phe Leu Lys Ala Glu Ser
    370                 375                 380

Glu Glu Glu Ile Phe Ala His Leu Gly Leu Asp Tyr Ile Glu Pro Trp
385                 390                 395                 400

Glu Arg Asn Ala


<210> SEQ ID NO 38
<211> LENGTH: 379
<212> TYPE: PRT
<213> ORGANISM: ARTIFICIAL SEQUENCE
<220> FEATURE:
<223> OTHER INFORMATION: N27 trunc wt (Sus scrofa)

<400> SEQUENCE: 38

Ser Ala Ser Pro Ser Pro Gly Ser Gln Asn Thr Leu Pro Pro Ala Val
1               5                   10                  15

Lys Lys Ile Ser Gln Tyr Ala Cys Gln Arg Arg Thr Thr Leu Asn Asn
            20                  25                  30

Cys Asn His Ile Phe Thr Asp Ala Phe Glu Val Leu Ala Glu Asn Tyr
        35                  40                  45

Glu Phe Arg Glu Asn Glu Thr Phe Cys Leu Ala Phe Met Arg Ala Ala
    50                  55                  60

Ser Val Leu Lys Ser Leu Pro Phe Thr Ile Ile Ser Met Lys Asp Thr
65                  70                  75                  80

Glu Gly Ile Pro Cys Leu Gly Asp Lys Val Lys Cys Val Ile Glu Glu
                85                  90                  95

Ile Ile Glu Asp Gly Glu Ser Ser Glu Val Lys Ala Val Leu Asn Asp
            100                 105                 110

Glu Arg Tyr Gln Ser Phe Lys Leu Phe Thr Ser Val Phe Gly Val Gly
        115                 120                 125

Leu Lys Thr Ser Glu Arg Trp Phe Arg Met Gly Phe Arg Ser Leu Ser
    130                 135                 140

Lys Ile Arg Ser Asp Lys Thr Leu Lys Phe Thr Arg Met Gln Lys Ala
145                 150                 155                 160

Gly Phe Leu Tyr Tyr Glu Asp Leu Val Ser Cys Val Thr Arg Ala Glu
                165                 170                 175

Ala Glu Ala Val Gly Val Leu Val Lys Glu Ala Val Gln Ala Phe Leu
            180                 185                 190

Pro Asp Ala Phe Val Thr Met Thr Gly Gly Phe Arg Arg Gly Lys Lys
        195                 200                 205

Met Gly His Asp Val Asp Phe Leu Ile Thr Ser Pro Gly Ser Thr Asp
    210                 215                 220

Asp Glu Glu Gln Gln Leu Leu Pro Lys Val Val Asn Leu Trp Glu Arg
225                 230                 235                 240

Glu Gly Leu Leu Leu Tyr Cys Asp Leu Val Glu Ser Thr Leu Glu Lys
                245                 250                 255
```

```
Ser Lys Leu Pro Ser Arg Asn Val Asp Ala Leu Asp His Phe Gln Lys
            260                 265                 270

Cys Phe Leu Ile Leu Lys Leu His His Gln Arg Val Asp Ser Gly Met
        275                 280                 285

Ser Ser Gln Gln Glu Gly Lys Thr Trp Lys Ala Ile Arg Val Asp Leu
    290                 295                 300

Val Met Cys Pro Tyr Glu Leu Arg Ala Phe Ala Leu Leu Gly Trp Thr
305                 310                 315                 320

Gly Ser Arg Gln Phe Glu Arg Asp Leu Arg Arg Tyr Ala Thr His Glu
                325                 330                 335

Arg Lys Met Ile Leu Asp Asn His Ala Leu Tyr Asp Lys Thr Lys Arg
            340                 345                 350

Ile Phe Leu Lys Ala Glu Ser Glu Glu Glu Ile Phe Ala His Leu Gly
        355                 360                 365

Leu Asp Tyr Leu Glu Pro Trp Glu Arg Asn Ala
    370                 375


<210> SEQ ID NO 39
<211> LENGTH: 379
<212> TYPE: PRT
<213> ORGANISM: ARTIFICIAL SEQUENCE
<220> FEATURE:
<223> OTHER INFORMATION: N27 trunc new

<400> SEQUENCE: 39

Ser Pro Ser Pro Val Pro Gly Ser Gln Asn Val Pro Ala Pro Val Val
1               5                   10                  15

Lys Lys Ile Ser Gln Tyr Ala Cys Gln Arg Arg Thr Thr Leu Asn Asn
            20                  25                  30

Tyr Asn Glu Ile Phe Thr Arg Ala Phe Glu Ile Leu Ala Glu Asn Tyr
        35                  40                  45

Glu Phe Arg Glu Asn Glu Glu Ser Tyr Val Thr Phe Arg Arg Ala Ala
    50                  55                  60

Ser Val Leu Lys Ser Leu Pro Phe Thr Ile Ile Ser Met Lys Asp Thr
65                  70                  75                  80

Glu Gly Ile Pro Cys Leu Gly Asp Lys Val Lys Arg Val Ile Glu Glu
                85                  90                  95

Ile Ile Glu Asp Gly Glu Ser Ser Glu Val Lys Ala Val Leu Asn Asp
            100                 105                 110

Glu Arg Tyr Lys Ala Phe Lys Leu Phe Thr Ser Val Phe Gly Val Gly
        115                 120                 125

Arg Lys Thr Ser Glu Lys Trp Phe Arg Met Gly Phe Arg Thr Leu Glu
    130                 135                 140

Lys Ile Arg Ser Asp Lys Thr Leu Lys Phe Thr Arg Met Gln Lys Ala
145                 150                 155                 160

Gly Phe Leu Tyr Tyr Glu Asp Leu Val Ser Arg Val Thr Arg Ala Glu
                165                 170                 175

Ala Glu Ala Val Ser Val Leu Val Lys Glu Ala Val Trp Ala Phe Leu
            180                 185                 190

Pro Asp Ala Phe Val Thr Met Thr Gly Gly Phe Arg Leu Gly Lys Lys
        195                 200                 205

Ile Gly His Asp Val Asp Phe Leu Ile Thr Ser Pro Gly Ser Thr Glu
    210                 215                 220

Glu Glu Glu Gln Gln Leu Leu His Lys Val Ile Asn Leu Trp Glu Lys
225                 230                 235                 240
```

```
Lys Gly Leu Leu Leu Tyr Tyr Asp Leu Val Glu Ser Thr Phe Glu Lys
                245                 250                 255

Leu Lys Leu Pro Ser Arg Thr Val Asp Ala Leu Asp His Phe Gln Lys
            260                 265                 270

Cys Phe Leu Ile Leu Lys Leu His His Gln Arg Val Gly Ser Gly Lys
        275                 280                 285

Ser Ser Gln Gln Glu Gly Lys Thr Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Pro Gln Phe Asn Arg Asp Leu Arg Arg Tyr Ala Thr His Glu
                325                 330                 335

Arg Lys Met Met Leu Asp Asn His Ala Leu Tyr Asp Lys Thr Lys Arg
            340                 345                 350

Ile Phe Leu Lys Ala Glu Ser Glu Glu Glu Ile Phe Ala His Leu Gly
        355                 360                 365

Leu Asp Tyr Ile Glu Pro Trp Glu Arg Asn Ala
    370                 375


<210> SEQ ID NO 40
<211> LENGTH: 404
<212> TYPE: PRT
<213> ORGANISM: ARTIFICIAL SEQUENCE
<220> FEATURE:
<223> OTHER INFORMATION: N27

<400> SEQUENCE: 40

Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30

Ser Gln Asn Val Pro Ala Pro Val Val Lys Lys Ile Ser Gln Tyr Ala
        35                  40                  45

Cys Gln Arg Arg Thr Thr Leu Asn Asn Tyr Asn Glu Ile Phe Thr Arg
    50                  55                  60

Ala Phe Glu Ile Leu Ala Glu Asn Tyr Glu Phe Arg Glu Asn Glu Glu
65                  70                  75                  80

Ser Tyr Val Thr Phe Arg Arg Ala Ala Ser Val Leu Lys Ser Leu Pro
                85                  90                  95

Phe Thr Ile Ile Ser Met Lys Asp Thr Glu Gly Ile Pro Cys Leu Gly
            100                 105                 110

Asp Lys Val Lys Arg Val Ile Glu Glu Ile Ile Glu Asp Gly Glu Ser
        115                 120                 125

Ser Glu Val Lys Ala Val Leu Asn Asp Glu Arg Tyr Lys Ala Phe Lys
    130                 135                 140

Leu Phe Thr Ser Val Phe Gly Val Gly Arg Lys Thr Ser Glu Lys Trp
145                 150                 155                 160

Phe Arg Met Gly Phe Arg Thr Leu Glu Lys Ile Arg Ser Asp Lys Thr
                165                 170                 175

Leu Lys Phe Thr Arg Met Gln Lys Ala Gly Phe Leu Tyr Tyr Glu Asp
            180                 185                 190

Leu Val Ser Arg Val Thr Arg Ala Glu Ala Glu Ala Val Ser Val Leu
        195                 200                 205

Val Lys Glu Ala Val Trp Ala Phe Leu Pro Asp Ala Phe Val Thr Met
    210                 215                 220
```

Thr Gly Gly Phe Arg Leu Gly Lys Lys Ile Gly His Asp Val Asp Phe
225 230 235 240

Leu Ile Thr Ser Pro Gly Ser Thr Glu Glu Glu Glu Gln Gln Leu Leu
245 250 255

His Lys Val Ile Asn Leu Trp Glu Lys Lys Gly Leu Leu Leu Tyr Tyr
260 265 270

Asp Leu Val Glu Ser Thr Phe Glu Lys Leu Lys Leu Pro Ser Arg Thr
275 280 285

Val Asp Ala Leu Asp His Phe Gln Lys Cys Phe Leu Ile Leu Lys Leu
290 295 300

His His Gln Arg Val Gly Ser Gly Lys Ser Ser Gln Gln Glu Gly Lys
305 310 315 320

Thr Trp Lys Ala Ile Arg Val Asp Leu Val Met Cys Pro Tyr Glu Arg
325 330 335

Arg Ala Phe Ala Leu Leu Gly Trp Thr Gly Ser Pro Gln Phe Asn Arg
340 345 350

Asp Leu Arg Arg Tyr Ala Thr His Glu Arg Lys Met Met Leu Asp Asn
355 360 365

His Ala Leu Tyr Asp Lys Thr Lys Arg Ile Phe Leu Lys Ala Glu Ser
370 375 380

Glu Glu Glu Ile Phe Ala His Leu Gly Leu Asp Tyr Ile Glu Pro Trp
385 390 395 400

Glu Arg Asn Ala

<210> SEQ ID NO 41
<211> LENGTH: 379
<212> TYPE: PRT
<213> ORGANISM: ARTIFICIAL SEQUENCE
<220> FEATURE:
<223> OTHER INFORMATION: N35 trunc wt (Panthera tigris altaica)

<400> SEQUENCE: 41

Tyr Ser Ala Ser Pro Asn Pro Glu Leu Gln Lys Thr Pro Pro Leu Val
1 5 10 15

Lys Lys Ile Pro Leu Tyr Ala Cys Gln Arg Arg Thr Thr Leu Asn Asn
20 25 30

Phe Asn His Val Phe Thr Asp Ala Phe Glu Val Leu Ala Glu Asn Tyr
35 40 45

Glu Phe Lys Glu Asn Glu Val Ser Ser Ala Thr Phe Met Arg Ala Ala
50 55 60

Ser Val Leu Lys Ser Leu Pro Phe Thr Ile Ile Ser Met Lys Asp Thr
65 70 75 80

Glu Gly Ile Pro Cys Leu Gly Asp Lys Val Lys Cys Val Ile Glu Glu
85 90 95

Ile Ile Glu Asp Gly Glu Ser Ser Glu Val Lys Ala Val Leu Asn Asp
100 105 110

Glu Arg Tyr Gln Ser Phe Lys Leu Phe Thr Ser Val Phe Gly Val Gly
115 120 125

Leu Lys Thr Ser Glu Lys Trp Phe Arg Met Gly Phe Arg Thr Leu Ser
130 135 140

Lys Ile Lys Ser Asp Lys Thr Leu Lys Phe Thr Gln Met Gln Lys Ala
145 150 155 160

Gly Phe Leu Tyr Tyr Glu Asp Leu Val Ser Cys Val Thr Arg Ala Glu
165 170 175

```
Ala Glu Ala Val Gly Val Leu Val Lys Glu Ala Val Trp Ala Phe Leu
            180                 185                 190

Pro Asp Ala Phe Val Thr Met Thr Gly Gly Phe Arg Arg Gly Lys Lys
        195                 200                 205

Ile Gly His Asp Val Asp Phe Leu Ile Thr Ser Pro Gly Ser Thr Asp
    210                 215                 220

Glu Glu Glu Glu Glu Leu Leu Pro Lys Val Ile Asn Leu Trp Gln Arg
225                 230                 235                 240

Lys Glu Leu Leu Leu Tyr Tyr Asp Leu Val Glu Ser Thr Phe Glu Lys
                245                 250                 255

Leu Lys Leu Pro Ser Arg Lys Val Asp Ala Leu Asp His Phe Gln Lys
            260                 265                 270

Cys Phe Leu Ile Leu Lys Leu His His Gln Arg Val Asp Ser Gly Lys
        275                 280                 285

Cys Ser Gln Gln Glu Gly Lys Thr Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Arg Gln Phe Glu Arg Asp Leu Arg Arg Tyr Ala Thr His Glu
                325                 330                 335

Arg Lys Met Ile Leu Asp Asn His Ala Leu Tyr Asp Lys Thr Lys Lys
            340                 345                 350

Ile Phe Leu Lys Ala Glu Ser Glu Glu Glu Ile Phe Ala His Leu Gly
        355                 360                 365

Leu Asp Tyr Ile Glu Pro Trp Glu Arg Asn Ala
    370                 375


<210> SEQ ID NO 42
<211> LENGTH: 379
<212> TYPE: PRT
<213> ORGANISM: ARTIFICIAL SEQUENCE
<220> FEATURE:
<223> OTHER INFORMATION: N35 trunc new

<400> SEQUENCE: 42

Ser Pro Ser Pro Val Pro Gly Ser Gln Asn Val Pro Ala Pro Val Val
1               5                   10                  15

Lys Lys Ile Ser Gln Tyr Ala Cys Gln Arg Arg Thr Thr Leu Asn Asn
            20                  25                  30

Tyr Asn Glu Ile Phe Thr Arg Ala Phe Glu Val Leu Ala Glu Asn Tyr
        35                  40                  45

Glu Phe Arg Glu Asn Glu Glu Ser Tyr Val Thr Phe Arg Arg Ala Ala
    50                  55                  60

Ser Val Leu Lys Ser Leu Pro Phe Thr Ile Ile Ser Met Lys Asp Thr
65                  70                  75                  80

Glu Gly Ile Pro Cys Leu Gly Asp Lys Val Lys Arg Val Ile Glu Glu
                85                  90                  95

Ile Ile Glu Asp Gly Glu Ser Ser Glu Val Lys Ala Val Leu Asn Asp
            100                 105                 110

Glu Arg Tyr Gln Ala Phe Lys Leu Phe Thr Ser Val Phe Gly Val Gly
        115                 120                 125

Arg Lys Thr Ser Glu Lys Trp Phe Arg Met Gly Phe Arg Thr Leu Glu
    130                 135                 140

Lys Ile Arg Ser Asp Lys Thr Leu Lys Phe Thr Arg Met Gln Lys Ala
145                 150                 155                 160
```

```
Gly Phe Leu Tyr Tyr Glu Asp Leu Ala Glu Arg Val Thr Arg Ala Glu
            165                 170                 175

Ala Glu Ala Val Ser Val Leu Val Lys Glu Ala Val Trp Ala Phe Leu
            180                 185                 190

Pro Asp Ala Phe Val Thr Met Thr Gly Gly Phe Arg Leu Gly Lys Lys
        195                 200                 205

Ile Gly His Asp Val Asp Phe Leu Ile Thr Ser Pro Gly Ser Thr Glu
    210                 215                 220

Glu Glu Glu Gln Gln Leu Leu Pro Lys Val Ile Asn Leu Trp Glu Arg
225                 230                 235                 240

Lys Gly Leu Leu Leu Tyr Tyr Asp Leu Val Glu Ser Thr Phe Glu Lys
                245                 250                 255

Leu Lys Leu Pro Ser Arg Lys Val Asp Ala Leu Asp His Phe Gln Lys
            260                 265                 270

Cys Phe Leu Ile Leu Lys Leu His His Gln Arg Val Gly Ser Gly Lys
        275                 280                 285

Ser Ser Gln Gln Glu Gly Lys Thr Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Ala Phe Phe Asn Arg Asp Leu Arg Arg Tyr Ala Thr His Glu
                325                 330                 335

Arg Lys Met Ile Leu Asp Asn His Ala Leu Tyr Asp Lys Thr Lys Arg
            340                 345                 350

Ile Phe Leu Lys Ala Glu Ser Glu Glu Glu Ile Phe Ala His Leu Gly
        355                 360                 365

Leu Asp Tyr Ile Glu Pro Trp Glu Arg Asn Ala
    370                 375


<210> SEQ ID NO 43
<211> LENGTH: 410
<212> TYPE: PRT
<213> ORGANISM: ARTIFICIAL SEQUENCE
<220> FEATURE:
<223> OTHER INFORMATION: N35

<400> SEQUENCE: 43

Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30

Ser Gln Asn Val Pro Ala Pro Val Val Lys Lys Ile Ser Gln Tyr Ala
        35                  40                  45

Cys Gln Arg Arg Thr Thr Leu Asn Asn Tyr Asn Glu Ile Phe Thr Arg
    50                  55                  60

Ala Phe Glu Val Leu Ala Glu Asn Tyr Glu Phe Arg Glu Asn Glu Glu
65                  70                  75                  80

Ser Tyr Val Thr Phe Arg Arg Ala Ala Ser Val Leu Lys Ser Leu Pro
                85                  90                  95

Phe Thr Ile Ile Ser Met Lys Asp Thr Glu Gly Ile Pro Cys Leu Gly
            100                 105                 110

Asp Lys Val Lys Arg Val Ile Glu Glu Ile Ile Glu Asp Gly Glu Ser
        115                 120                 125

Ser Glu Val Lys Ala Val Leu Asn Asp Glu Arg Tyr Gln Ala Phe Lys
    130                 135                 140
```

```
Leu Phe Thr Ser Val Phe Gly Val Gly Arg Lys Thr Ser Glu Lys Trp
145                 150                 155                 160

Phe Arg Met Gly Phe Arg Thr Leu Glu Lys Ile Arg Ser Asp Lys Thr
                165                 170                 175

Leu Lys Phe Thr Arg Met Gln Lys Ala Gly Phe Leu Tyr Tyr Glu Asp
            180                 185                 190

Leu Ala Glu Arg Val Thr Arg Ala Glu Ala Glu Ala Val Ser Val Leu
        195                 200                 205

Val Lys Glu Ala Val Trp Ala Phe Leu Pro Asp Ala Phe Val Thr Met
    210                 215                 220

Thr Gly Gly Phe Arg Leu Gly Lys Lys Ile Gly His Asp Val Asp Phe
225                 230                 235                 240

Leu Ile Thr Ser Pro Gly Ser Thr Glu Glu Glu Glu Gln Gln Leu Leu
                245                 250                 255

Pro Lys Val Ile Asn Leu Trp Glu Arg Lys Gly Leu Leu Leu Tyr Tyr
            260                 265                 270

Asp Leu Val Glu Ser Thr Phe Glu Lys Leu Lys Leu Pro Ser Arg Lys
        275                 280                 285

Val Asp Ala Leu Asp His Phe Gln Lys Cys Phe Leu Ile Leu Lys Leu
    290                 295                 300

His His Gln Arg Val Gly Ser Gly Lys Ser Ser Gln Gln Glu Gly Lys
305                 310                 315                 320

Thr Trp Lys Ala Ile Arg Val Asp Leu Val Met Cys Pro Tyr Glu Arg
                325                 330                 335

Arg Ala Phe Ala Leu Leu Gly Trp Thr Gly Ser Ala Phe Phe Asn Arg
            340                 345                 350

Asp Leu Arg Arg Tyr Ala Thr His Glu Arg Lys Met Ile Leu Asp Asn
        355                 360                 365

His Ala Leu Tyr Asp Lys Thr Lys Arg Ile Phe Leu Lys Ala Glu Ser
    370                 375                 380

Glu Glu Glu Ile Phe Ala His Leu Gly Leu Asp Tyr Ile Glu Pro Trp
385                 390                 395                 400

Glu Arg Asn Ala Ala Ala Ala Ile Gly Cys
                405                 410
```

<210> SEQ ID NO 44
<211> LENGTH: 365
<212> TYPE: PRT
<213> ORGANISM: ARTIFICIAL SEQUENCE
<220> FEATURE:
<223> OTHER INFORMATION: N72 trunc wt (Bubalus bubalis)

<400> SEQUENCE: 44

```
Leu Ala Val Lys Lys Ile Ser Gln Tyr Ala Cys Gln Arg Lys Thr Thr
1               5                   10                  15

Leu Asn Asn Tyr Asn His Ile Phe Thr Asp Ala Phe Glu Ile Leu Ala
            20                  25                  30

Glu Asn Ser Glu Phe Lys Glu Asn Glu Val Ser Tyr Val Thr Phe Met
        35                  40                  45

Arg Ala Ala Ser Val Leu Lys Ser Leu Pro Phe Thr Ile Ile Ser Met
    50                  55                  60

Lys Asp Thr Gln Gly Ile Pro Cys Leu Gly Asp Lys Val Lys Cys Val
65                  70                  75                  80

Ile Glu Glu Ile Ile Glu Asp Gly Glu Ser Ser Glu Val Lys Ala Val
                85                  90                  95
```

-continued

```
Leu Asn Asp Glu Arg Tyr Gln Ser Phe Lys Leu Phe Thr Ser Val Phe
            100                 105                 110

Gly Val Gly Leu Lys Thr Ser Glu Lys Trp Phe Arg Met Gly Phe Arg
        115                 120                 125

Ser Leu Ser Lys Ile Thr Ser Asp Lys Thr Leu Lys Phe Thr Lys Met
    130                 135                 140

Gln Lys Ala Gly Phe Leu Tyr Tyr Glu Asp Leu Val Ser Cys Val Thr
145                 150                 155                 160

Arg Ala Glu Ala Glu Ala Val Gly Val Leu Val Lys Glu Ala Val Trp
                165                 170                 175

Ala Phe Leu Pro Asp Ala Phe Ile Thr Met Thr Gly Gly Phe Arg Arg
            180                 185                 190

Gly Lys Lys Ile Gly His Asp Val Asp Phe Leu Ile Thr Ser Pro Gly
        195                 200                 205

Ser Ala Glu Asp Glu Glu Gln Leu Leu Pro Lys Val Ile Asn Leu Trp
    210                 215                 220

Glu Lys Lys Gly Leu Leu Leu Tyr Tyr Asp Leu Val Glu Ser Thr Phe
225                 230                 235                 240

Glu Lys Phe Lys Leu Pro Ser Arg Gln Val Asp Thr Leu Asp His Phe
                245                 250                 255

Gln Lys Cys Phe Leu Ile Leu Lys Leu His His Gln Arg Val Asp Ser
            260                 265                 270

Gly Arg Ser Asn Gln Gln Glu Gly Lys Thr Trp Lys Ala Ile Arg Val
        275                 280                 285

Asp Leu Val Met Cys Pro Tyr Glu Asn Arg Ala Phe Ala Leu Leu Gly
    290                 295                 300

Trp Thr Gly Ser Arg Gln Phe Glu Arg Asp Ile Arg Arg Tyr Ala Thr
305                 310                 315                 320

His Glu Arg Lys Met Met Leu Asp Asn His Ala Leu Tyr Asp Lys Thr
                325                 330                 335

Lys Arg Val Phe Leu Lys Ala Glu Ser Glu Glu Glu Ile Phe Ala His
            340                 345                 350

Leu Gly Leu Asp Tyr Ile Glu Pro Trp Glu Arg Asn Ala
        355                 360                 365


<210> SEQ ID NO 45
<211> LENGTH: 366
<212> TYPE: PRT
<213> ORGANISM: ARTIFICIAL SEQUENCE
<220> FEATURE:
<223> OTHER INFORMATION: N72 trunc new

<400> SEQUENCE: 45

Ser Val Val Lys Lys Ile Ser Gln Tyr Ala Cys Gln Arg Arg Thr Thr
1               5                   10                  15

Leu Asn Asn Tyr Asn Glu Ile Phe Thr Arg Ala Phe Glu Ile Leu Ala
            20                  25                  30

Glu Asn Tyr Glu Phe Lys Glu Asn Glu Glu Ser Tyr Val Thr Phe Arg
        35                  40                  45

Arg Ala Ala Ser Val Leu Lys Ser Leu Pro Phe Thr Ile Ile Ser Met
    50                  55                  60

Lys Asp Thr Glu Gly Ile Pro Cys Leu Gly Asp Lys Val Lys Arg Val
65                  70                  75                  80

Ile Glu Glu Ile Ile Glu Asp Gly Glu Ser Ser Glu Val Lys Ala Val
                85                  90                  95
```

-continued

```
Leu Asn Asp Glu Arg Tyr Gln Ala Phe Lys Leu Phe Thr Ser Val Phe
            100                 105                 110

Gly Val Gly Arg Lys Thr Ser Glu Lys Trp Phe Arg Met Gly Phe Arg
        115                 120                 125

Ser Leu Glu Lys Ile Arg Ser Asp Lys Thr Leu Lys Phe Thr Arg Met
    130                 135                 140

Gln Lys Ala Gly Phe Leu Tyr Tyr Glu Asp Leu Val Ser Arg Val Thr
145                 150                 155                 160

Arg Ala Glu Ala Glu Ala Val Gly Val Leu Val Lys Glu Ala Val Trp
                165                 170                 175

Ala Phe Leu Pro Asp Ala Phe Val Thr Met Thr Gly Gly Phe Arg Leu
            180                 185                 190

Gly Lys Lys Ile Gly His Asp Val Asp Phe Leu Ile Thr Ser Pro Gly
        195                 200                 205

Ser Thr Glu Asp Glu Glu Gln Gln Leu Leu Pro Lys Val Ile Asn Leu
    210                 215                 220

Trp Glu Arg Lys Gly Leu Leu Leu Tyr Tyr Asp Leu Val Glu Ser Thr
225                 230                 235                 240

Phe Glu Lys Phe Lys Leu Pro Ser Arg Gln Val Asp Ala Leu Asp His
                245                 250                 255

Phe Gln Lys Cys Phe Leu Ile Leu Lys Leu His His Gln Arg Val Gly
            260                 265                 270

Ser Gly Lys Ser Ser Gln Gln Glu Gly Lys Thr Trp Lys Ala Ile Arg
        275                 280                 285

Val Asp Leu Val Met Cys Pro Tyr Glu Gln Arg Ala Phe Ala Leu Leu
    290                 295                 300

Gly Trp Thr Gly Ser Ala Phe Phe Asn Arg Asp Leu Arg Arg Tyr Ala
305                 310                 315                 320

Thr His Glu Arg Lys Met Met Leu Asp Asn His Ala Leu Tyr Asp Lys
                325                 330                 335

Thr Lys Arg Ile Phe Leu Lys Ala Glu Ser Glu Glu Glu Ile Phe Ala
            340                 345                 350

His Leu Gly Leu Asp Tyr Ile Glu Pro Arg Glu Arg Asn Ala
        355                 360                 365
```

<210> SEQ ID NO 46
<211> LENGTH: 391
<212> TYPE: PRT
<213> ORGANISM: ARTIFICIAL SEQUENCE
<220> FEATURE:
<223> OTHER INFORMATION: N72

<400> SEQUENCE: 46

```
Met Ala Ser Ser His His His His His His Ser Ser Gly Ser Glu Asn
1               5                   10                  15

Leu Tyr Phe Gln Thr Gly Ser Ser Gly Ser Val Val Lys Lys Ile Ser
            20                  25                  30

Gln Tyr Ala Cys Gln Arg Arg Thr Thr Leu Asn Asn Tyr Asn Glu Ile
        35                  40                  45

Phe Thr Arg Ala Phe Glu Ile Leu Ala Glu Asn Tyr Glu Phe Lys Glu
    50                  55                  60

Asn Glu Glu Ser Tyr Val Thr Phe Arg Arg Ala Ala Ser Val Leu Lys
65                  70                  75                  80

Ser Leu Pro Phe Thr Ile Ile Ser Met Lys Asp Thr Glu Gly Ile Pro
                85                  90                  95
```

-continued

```
Cys Leu Gly Asp Lys Val Lys Arg Val Ile Glu Glu Ile Ile Glu Asp
            100                 105                 110

Gly Glu Ser Ser Glu Val Lys Ala Val Leu Asn Asp Glu Arg Tyr Gln
        115                 120                 125

Ala Phe Lys Leu Phe Thr Ser Val Phe Gly Val Gly Arg Lys Thr Ser
    130                 135                 140

Glu Lys Trp Phe Arg Met Gly Phe Arg Ser Leu Glu Lys Ile Arg Ser
145                 150                 155                 160

Asp Lys Thr Leu Lys Phe Thr Arg Met Gln Lys Ala Gly Phe Leu Tyr
                165                 170                 175

Tyr Glu Asp Leu Val Ser Arg Val Thr Arg Ala Glu Ala Glu Ala Val
            180                 185                 190

Gly Val Leu Val Lys Glu Ala Val Trp Ala Phe Leu Pro Asp Ala Phe
        195                 200                 205

Val Thr Met Thr Gly Gly Phe Arg Leu Gly Lys Lys Ile Gly His Asp
    210                 215                 220

Val Asp Phe Leu Ile Thr Ser Pro Gly Ser Thr Glu Asp Glu Glu Gln
225                 230                 235                 240

Gln Leu Leu Pro Lys Val Ile Asn Leu Trp Glu Arg Lys Gly Leu Leu
                245                 250                 255

Leu Tyr Tyr Asp Leu Val Glu Ser Thr Phe Glu Lys Phe Lys Leu Pro
            260                 265                 270

Ser Arg Gln Val Asp Ala Leu Asp His Phe Gln Lys Cys Phe Leu Ile
        275                 280                 285

Leu Lys Leu His His Gln Arg Val Gly Ser Gly Lys Ser Ser Gln Gln
    290                 295                 300

Glu Gly Lys Thr Trp Lys Ala Ile Arg Val Asp Leu Val Met Cys Pro
305                 310                 315                 320

Tyr Glu Gln Arg Ala Phe Ala Leu Leu Gly Trp Thr Gly Ser Ala Phe
                325                 330                 335

Phe Asn Arg Asp Leu Arg Arg Tyr Ala Thr His Glu Arg Lys Met Met
            340                 345                 350

Leu Asp Asn His Ala Leu Tyr Asp Lys Thr Lys Arg Ile Phe Leu Lys
        355                 360                 365

Ala Glu Ser Glu Glu Glu Ile Phe Ala His Leu Gly Leu Asp Tyr Ile
    370                 375                 380

Glu Pro Arg Glu Arg Asn Ala
385                 390


<210> SEQ ID NO 47
<211> LENGTH: 379
<212> TYPE: PRT
<213> ORGANISM: ARTIFICIAL SEQUENCE
<220> FEATURE:
<223> OTHER INFORMATION: N93or trunc wt (Marmota flaviventris)

<400> SEQUENCE: 47

Pro Asp His Ser Asn Ser Asp Pro Gln Arg Ile Pro Pro Pro Ala Val
1               5                   10                  15

Gln Thr Ile Ser Gln Tyr Ala Cys Gln Arg Arg Thr Thr Leu Asn Asn
            20                  25                  30

Cys Asn Arg Val Phe Thr Asp Ala Phe Asp Val Leu Ala Glu Asn Tyr
        35                  40                  45

Glu Phe Arg Glu Asn Glu Ser Cys Ser Val Val Phe Met Arg Ala Ala
    50                  55                  60
```

-continued

```
Ser Val Leu Lys Ser Leu Pro Phe Thr Ile Ile Ser Met Arg Asp Leu
65                  70                  75                  80

Glu Gly Ile Pro Cys Leu Glu Gly Lys Ala Lys Ser Ile Ile Glu Glu
                85                  90                  95

Ile Ile Glu Asp Gly Glu Ser Ser Glu Val Lys Ala Val Leu Asn Asp
            100                 105                 110

Glu Arg Tyr Lys Ser Phe Lys Leu Phe Thr Ser Val Phe Gly Val Gly
        115                 120                 125

Leu Lys Thr Ser Glu Lys Trp Phe Arg Met Gly Phe Arg Thr Leu Ser
    130                 135                 140

Lys Ile Arg Ser Asp Lys Ser Leu Lys Phe Thr His Met Gln Lys Ala
145                 150                 155                 160

Gly Phe Leu Tyr Tyr Glu Asp Leu Val Ser Cys Val Thr Arg Ala Glu
                165                 170                 175

Ala Glu Ala Val Ser Val Leu Val Lys Glu Ala Val Trp Ala Phe Leu
            180                 185                 190

Pro Asp Ala Phe Ile Thr Met Thr Gly Gly Phe Arg Arg Gly Lys Asn
        195                 200                 205

Ile Gly His Asp Val Asp Phe Leu Ile Thr Ser Ala Glu Ala Thr Glu
    210                 215                 220

Glu Glu Glu Gln Gln Leu Leu His Lys Val Thr Asn Leu Trp Glu Lys
225                 230                 235                 240

Lys Gly Leu Leu Leu Tyr Cys Asp Leu Val Glu Ser Thr Phe Glu Lys
                245                 250                 255

Leu Lys Thr Pro Ser Arg Lys Val Asp Ala Leu Asp His Phe Gln Lys
            260                 265                 270

Cys Phe Leu Ile Leu Lys Leu His His Gln Arg Val Asp Ser Asp Lys
        275                 280                 285

Ala Ser Gln Gln Gly Gly Lys Asn Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Arg Gln Phe Glu Arg Asp Leu Arg Arg Tyr Ala Thr His Glu
                325                 330                 335

Arg Lys Met Ile Leu Asp Asn His Ala Leu Tyr Asp Lys Thr Lys Arg
            340                 345                 350

Ile Phe Leu Lys Ala Glu Ser Glu Glu Glu Ile Phe Ala His Leu Gly
        355                 360                 365

Leu Asp Tyr Ile Glu Pro Trp Glu Arg Asn Ala
    370                 375
```

<210> SEQ ID NO 48
<211> LENGTH: 379
<212> TYPE: PRT
<213> ORGANISM: ARTIFICIAL SEQUENCE
<220> FEATURE:
<223> OTHER INFORMATION: N93or trunc new

<400> SEQUENCE: 48

```
Ser Pro Ser Pro Val Pro Gly Ser Gln Asn Val Pro Ala Pro Ala Val
1               5                   10                  15

Gln Thr Ile Ser Gln Tyr Ala Cys Gln Arg Arg Thr Thr Leu Asn Asn
            20                  25                  30

Tyr Asn Arg Val Phe Thr Asp Ala Phe Asp Val Leu Ala Glu Asn Tyr
        35                  40                  45
```

-continued

```
Glu Phe Arg Glu Asn Glu Glu Ser Ser Val Val Phe Arg Arg Ala Ala
    50                  55                  60

Ser Val Leu Lys Ser Leu Pro Phe Thr Ile Ile Ser Met Arg Asp Leu
65                  70                  75                  80

Glu Gly Ile Pro Cys Leu Glu Gly Lys Ala Lys Arg Ile Ile Glu Glu
                85                  90                  95

Ile Ile Glu Asp Gly Glu Ser Ser Glu Val Lys Ala Val Leu Asn Asp
            100                 105                 110

Glu Arg Tyr Lys Ala Phe Lys Leu Phe Thr Ser Val Phe Gly Val Gly
        115                 120                 125

Arg Lys Thr Ser Glu Lys Trp Phe Arg Met Gly Phe Arg Thr Leu Glu
    130                 135                 140

Lys Ile Arg Ser Asp Lys Ser Leu Lys Phe Thr His Met Gln Lys Ala
145                 150                 155                 160

Gly Phe Leu Tyr Tyr Glu Asp Leu Val Ser Arg Val Thr Arg Ala Glu
                165                 170                 175

Ala Glu Ala Val Ser Val Leu Val Lys Glu Ala Val Trp Ala Phe Leu
            180                 185                 190

Pro Asp Ala Phe Ile Thr Met Thr Gly Gly Phe Arg Leu Gly Lys Asn
        195                 200                 205

Ile Gly His Asp Val Asp Phe Leu Ile Thr Ser Ala Glu Ala Thr Glu
    210                 215                 220

Glu Glu Glu Gln Gln Leu Leu His Lys Val Thr Asn Leu Trp Glu Lys
225                 230                 235                 240

Lys Gly Leu Leu Leu Tyr Cys Asp Leu Val Glu Ser Thr Phe Glu Lys
                245                 250                 255

Leu Lys Leu Pro Ser Arg Thr Val Asp Ala Leu Asp His Phe Gln Lys
            260                 265                 270

Cys Phe Leu Ile Leu Lys Leu His His Gln Arg Val Asp Ser Asp Lys
        275                 280                 285

Ala Ser Gln Gln Gly Gly Lys Asn Trp Lys Ala Ile Arg Val Asp Leu
    290                 295                 300

Val Met Cys Pro Tyr Glu Arg Arg Ala Phe Ala Leu Leu Gly Trp Thr
305                 310                 315                 320

Gly Ser Pro Gln Phe Asn Arg Asp Leu Arg Arg Tyr Ala Thr His Glu
                325                 330                 335

Arg Lys Met Ile Leu Asp Asn His Ala Leu Tyr Asp Lys Thr Lys Arg
            340                 345                 350

Ile Phe Leu Lys Ala Glu Ser Glu Glu Glu Ile Phe Ala His Leu Gly
        355                 360                 365

Leu Asp Tyr Ile Glu Pro Arg Glu Arg Asn Ala
    370                 375

<210> SEQ ID NO 49
<211> LENGTH: 404
<212> TYPE: PRT
<213> ORGANISM: ARTIFICIAL SEQUENCE
<220> FEATURE:
<223> OTHER INFORMATION: N93or

<400> SEQUENCE: 49

Met Ala Ser Ser His His His His His His Ser Ser Gly Ser Glu Asn
1               5                   10                  15

Leu Tyr Phe Gln Thr Gly Ser Ser Gly Ser Pro Ser Pro Val Pro Gly
            20                  25                  30
```

-continued

```
Ser Gln Asn Val Pro Ala Pro Ala Val Gln Thr Ile Ser Gln Tyr Ala
        35                  40                  45

Cys Gln Arg Arg Thr Thr Leu Asn Asn Tyr Asn Arg Val Phe Thr Asp
    50                  55                  60

Ala Phe Asp Val Leu Ala Glu Asn Tyr Glu Phe Arg Glu Asn Glu Glu
65                  70                  75                  80

Ser Ser Val Val Phe Arg Arg Ala Ala Ser Val Leu Lys Ser Leu Pro
                85                  90                  95

Phe Thr Ile Ile Ser Met Arg Asp Leu Glu Gly Ile Pro Cys Leu Glu
            100                 105                 110

Gly Lys Ala Lys Arg Ile Ile Glu Glu Ile Ile Glu Asp Gly Glu Ser
        115                 120                 125

Ser Glu Val Lys Ala Val Leu Asn Asp Glu Arg Tyr Lys Ala Phe Lys
    130                 135                 140

Leu Phe Thr Ser Val Phe Gly Val Gly Arg Lys Thr Ser Glu Lys Trp
145                 150                 155                 160

Phe Arg Met Gly Phe Arg Thr Leu Glu Lys Ile Arg Ser Asp Lys Ser
                165                 170                 175

Leu Lys Phe Thr His Met Gln Lys Ala Gly Phe Leu Tyr Tyr Glu Asp
            180                 185                 190

Leu Val Ser Arg Val Thr Arg Ala Glu Ala Glu Ala Val Ser Val Leu
        195                 200                 205

Val Lys Glu Ala Val Trp Ala Phe Leu Pro Asp Ala Phe Ile Thr Met
    210                 215                 220

Thr Gly Gly Phe Arg Leu Gly Lys Asn Ile Gly His Asp Val Asp Phe
225                 230                 235                 240

Leu Ile Thr Ser Ala Glu Ala Thr Glu Glu Glu Gln Gln Leu Leu
                245                 250                 255

His Lys Val Thr Asn Leu Trp Glu Lys Lys Gly Leu Leu Leu Tyr Cys
            260                 265                 270

Asp Leu Val Glu Ser Thr Phe Glu Lys Leu Lys Leu Pro Ser Arg Thr
        275                 280                 285

Val Asp Ala Leu Asp His Phe Gln Lys Cys Phe Leu Ile Leu Lys Leu
    290                 295                 300

His His Gln Arg Val Asp Ser Asp Lys Ala Ser Gln Gln Gly Gly Lys
305                 310                 315                 320

Asn Trp Lys Ala Ile Arg Val Asp Leu Val Met Cys Pro Tyr Glu Arg
                325                 330                 335

Arg Ala Phe Ala Leu Leu Gly Trp Thr Gly Ser Pro Gln Phe Asn Arg
            340                 345                 350

Asp Leu Arg Arg Tyr Ala Thr His Glu Arg Lys Met Ile Leu Asp Asn
        355                 360                 365

His Ala Leu Tyr Asp Lys Thr Lys Arg Ile Phe Leu Lys Ala Glu Ser
    370                 375                 380

Glu Glu Glu Ile Phe Ala His Leu Gly Leu Asp Tyr Ile Glu Pro Arg
385                 390                 395                 400

Glu Arg Asn Ala
```

<210> SEQ ID NO 50
<211> LENGTH: 18
<212> TYPE: DNA
<213> ORGANISM: ARTIFICIAL SEQUENCE
<220> FEATURE:
<223> OTHER INFORMATION: PRIMER

<400> SEQUENCE: 50
aaaaaaaaaa aaaagggg 18

<210> SEQ ID NO 51
<211> LENGTH: 12
<212> TYPE: DNA
<213> ORGANISM: ARTIFICIAL SEQUENCE
<220> FEATURE:
<223> OTHER INFORMATION: PRIMER

<400> SEQUENCE: 51
cagttaaaaa ct 12

<210> SEQ ID NO 52
<211> LENGTH: 11
<212> TYPE: DNA
<213> ORGANISM: ARTIFICIAL SEQUENCE
<220> FEATURE:
<223> OTHER INFORMATION: PRIMER

<400> SEQUENCE: 52
gagttaaaac t 11

<210> SEQ ID NO 53
<211> LENGTH: 10
<212> TYPE: DNA
<213> ORGANISM: ARTIFICIAL SEQUENCE
<220> FEATURE:
<223> OTHER INFORMATION: PRIMER

<400> SEQUENCE: 53
cagcaaggct 10

<210> SEQ ID NO 54
<211> LENGTH: 25
<212> TYPE: PRT
<213> ORGANISM: ARTIFICIAL SEQUENCE
<220> FEATURE:
<223> OTHER INFORMATION: affinity tag for purifying TdT variants

<400> SEQUENCE: 54

Met Ala Ser Ser His His His His His His Ser Ser Gly Ser Glu Asn
1 5 10 15

Leu Tyr Phe Gln Thr Gly Ser Ser Gly
20 25

<210> SEQ ID NO 55
<211> LENGTH: 403
<212> TYPE: PRT
<213> ORGANISM: ARTIFICIAL SEQUENCE
<220> FEATURE:
<223> OTHER INFORMATION: M57 (with affinity tag)

<400> SEQUENCE: 55

Met Ala Ser Ser His His His His His His Ser Ser Gly Ser Glu Asn
1 5 10 15

Leu Tyr Phe Gln Thr Gly Ser Ser Gly Ser Pro Ser Pro Val Pro Gly
20 25 30

Ser Gln Asn Ala Pro Ala Pro Val Val Lys Lys Ile Ser Gln Tyr Ala
35 40 45

Cys Gln Arg Arg Thr Thr Leu Asn Asn Tyr Asn Glu Leu Phe Thr Arg
50 55 60

Ala Leu Asp Ile Leu Ala Glu Asn Asp Glu Phe Arg Glu Asn Glu Glu

-continued

```
65                  70                  75                  80

Ser Arg Asp Ala Phe Arg Arg Ala Ser Ser Val Leu Lys Ser Leu Pro
                85                  90                  95

Phe Pro Ile Thr Ser Met Lys Asp Thr Glu Gly Ile Pro Cys Leu Gly
            100                 105                 110

Asp Lys Val Lys Arg Ile Ile Glu Glu Ile Ile Glu Asp Gly Glu Ser
        115                 120                 125

Ser Glu Val Lys Ala Val Leu Asn Asp Glu Arg Tyr Lys Ala Phe Lys
    130                 135                 140

Leu Phe Thr Ser Val Phe Gly Val Gly Arg Lys Thr Ala Glu Lys Trp
145                 150                 155                 160

Phe Arg Met Gly Phe Arg Thr Leu Glu Lys Ile Arg Ser Asp Lys Ser
                165                 170                 175

Leu Arg Phe Thr Gln Met Gln Lys Ala Gly Phe Leu Tyr Tyr Glu Asp
            180                 185                 190

Leu Val Ser Gly Val Thr Arg Ala Glu Ala Glu Ala Val Gly Val Leu
        195                 200                 205

Val Lys Glu Ala Val Trp Ala Phe Leu Pro Asp Ala Phe Val Thr Met
    210                 215                 220

Thr Gly Gly Phe Arg Leu Gly Lys Lys Ile Gly His Asp Val Asp Phe
225                 230                 235                 240

Leu Ile Thr Ser Pro Gly Ser Ala Glu Asp Glu Glu Gln Leu Leu Pro
                245                 250                 255

Lys Val Ile Asn Leu Trp Glu Lys Lys Gly Leu Leu Leu Tyr Tyr Asp
            260                 265                 270

Leu Val Glu Ser Thr Phe Glu Lys Phe Lys Leu Pro Ser Arg Gln Val
        275                 280                 285

Asp Thr Leu Asp His Phe Gln Lys Cys Phe Leu Ile Leu Lys Leu His
    290                 295                 300

His Gln Arg Val Asp Ser Ser Lys Ser Asn Gln Gln Glu Gly Lys Thr
305                 310                 315                 320

Trp Lys Ala Ile Arg Val Asp Leu Val Met Cys Pro Tyr Glu Asn Arg
                325                 330                 335

Ala Phe Ala Leu Leu Gly Trp Thr Gly Ser Pro Gln Phe Asn Arg Asp
            340                 345                 350

Leu Arg Arg Tyr Ala Thr His Glu Arg Lys Met Met Leu Asp Asn His
        355                 360                 365

Ala Leu Tyr Asp Lys Thr Lys Arg Val Phe Leu Glu Ala Glu Ser Glu
    370                 375                 380

Glu Glu Ile Phe Ala His Leu Gly Leu Asp Tyr Ile Glu Pro Trp Glu
385                 390                 395                 400

Arg Asn Ala
```